(12) United States Patent
Kiani et al.

(10) Patent No.: US 11,884,925 B2
(45) Date of Patent: Jan. 30, 2024

(54) SYNTHETIC IMMUNOMODULATION WITH A CRISPR SUPER-REPRESSOR IN VIVO

(71) Applicant: ARIZONA BOARD OF REGENTS ON BEHALF OF ARIZONA STATE UNIVERSITY, Scottsdale, AZ (US)

(72) Inventors: Samira Kiani, Scottsdale, AZ (US); Mo Reza Ebrahimkhani, Scottsdale, AZ (US); Farzaneh Moghadam, Tempe, AZ (US)

(73) Assignee: ARIZONA BOARD OF REGENTS ON BEHALF OF ARIZONA STATE UNIVERSITY, Scottsdale, AZ (US)

( * ) Notice: Subject to any disclaimer, the term of this patent is extended or adjusted under 35 U.S.C. 154(b) by 0 days.

(21) Appl. No.: 17/292,407

(22) PCT Filed: Nov. 7, 2019

(86) PCT No.: PCT/US2019/060285
§ 371 (c)(1),
(2) Date: May 7, 2021

(87) PCT Pub. No.: WO2020/097344
PCT Pub. Date: May 14, 2020

(65) Prior Publication Data
US 2021/0380990 A1     Dec. 9, 2021

Related U.S. Application Data

(60) Provisional application No. 62/899,584, filed on Sep. 12, 2019, provisional application No. 62/757,679, filed on Nov. 8, 2018.

(51) Int. Cl.
| *C12N 15/63* | (2006.01) |
| *C07K 14/47* | (2006.01) |
| *C12N 9/22* | (2006.01) |
| *C12N 15/11* | (2006.01) |
| *C12N 15/86* | (2006.01) |
| *A61K 48/00* | (2006.01) |

(52) U.S. Cl.
CPC ........ *C12N 15/635* (2013.01); *A61K 48/0008* (2013.01); *C07K 14/4703* (2013.01); *C12N 9/22* (2013.01); *C12N 15/11* (2013.01); *C12N 15/111* (2013.01); *C12N 15/86* (2013.01); *C07K 2319/85* (2013.01); *C12N 2310/16* (2013.01); *C12N 2310/20* (2017.05); *C12N 2310/3519* (2013.01); *C12N 2830/005* (2013.01)

(58) Field of Classification Search
CPC ............ C12N 2310/20; C12N 2310/16; C12N 15/635; C12N 15/86
See application file for complete search history.

(56) References Cited

U.S. PATENT DOCUMENTS

| 10,550,372 B2 | 2/2020 | Konermann et al. |
| 2003/0148986 A1* | 8/2003 | Arditi .................. A61P 9/10 |
| | | 514/44 R |
| 2014/0073648 A1 | 3/2014 | Zhou et al. |
| 2015/0071900 A1 | 3/2015 | Liu et al. |
| 2017/0008924 A1 | 1/2017 | Lee et al. |
| 2017/0240896 A1 | 8/2017 | Qian et al. |

FOREIGN PATENT DOCUMENTS

| WO | 1998010088 A1 | 3/1998 | |
| WO | WO-2016094872 A1 * | 6/2016 | ............... C12N 9/22 |
| WO | 2016/205613 A1 | 12/2016 | |
| WO | WO-2016205613 A1 * | 12/2016 | ............... A61P 31/12 |
| WO | 2017/068077 A1 | 4/2017 | |
| WO | 2018/212361 A1 | 11/2018 | |
| WO | 2019/005856 A1 | 1/2019 | |

OTHER PUBLICATIONS

Patnaik et al. Gene structure, cDNA characterization and RNAi-based functional analysis of a myeloid differentiation factor 88 homolog in Tenebrio molitor larvae exposed to Staphylococcus aureus infection. Developmental and Comparative Immunology, vol. 46, pp. 208-221, Apr. 19, 2014. (Year: 2014).*
Alberts B, Johnson A, Lewis J, et al. Molecular Biology of the Cell. 4th edition. New York: Garland Science; 2002. Glossary entry for "locus." Available from: https://www.ncbi.nlm.nih.gov/books/NBK21052/, printed as p. 1/1. (Year: 2002).*
Martinez-Lopez et al. MYD88 (L265P) somatic mutation in marginal zone B-cell lymphoma. The American Journal of Surgical Pathology, vol. 39, No. 5, pp. 644-651, May 2015. (Year: 2015).*
Ferreira et al. PPAR-gamma/IL-10 axis inhibits MyD88 expression and ameliorates murine polymicrobial sepsis. The Journal of Immunology, vol. 192, pp. 2357-2365, and p. 1/1 of Figure S1, 2014. (Year: 2014).*
Kumar et al. Insertion/deletion-activated frame-shift fluorescence protein is a sensitive reporter for genomic DNA editing. BMC Genomics, vol. 20: 609, Jul. 24, 2019, printed as pp. 1/10-10/10. (Year: 2019).*
Salcedo et al. MyD88 and its divergent toll in carcinogenesis. Trends in Immunology, vol. 34, No. 8, pp. 379-389, Aug. 2013. (Year: 2013).*
Cox et al. Therapeutic genome editing: prospects and challenges. Nature Medicine, vol. 21, No. 2, pp. 121-131, Feb. 2015. (Year: 2015).*
Adli, M. The CRISPR tool kit for genome editing and beyond. Nature Communications, vol. 9: 1911, 2018, printed as pp. 1-13. (Year: 2018).*
Kiani et al. Cas9 gRNA engineering for genome editing, activation and repression. Nature Methods, vol. 12, No. 11, pp. 1051-1054, pp. 1/2-2/2 of Online Methods, and pp. 1/34-34/34 of Supplementary Information, Sep. 7, 2015. (Year: 2015).*

(Continued)

*Primary Examiner* — Jennifer Dunston
(74) *Attorney, Agent, or Firm* — Quarles & Brady, LLP

(57) ABSTRACT

Provided herein are CRISPR-based synthetic repression systems as well as methods and compositions using the synthetic repression systems to treat septicemia, an adverse immune response in a subject and Waldenström macroglobulinemia.

11 Claims, 23 Drawing Sheets

Specification includes a Sequence Listing.

(56) References Cited

OTHER PUBLICATIONS

Platt et al., CRISPR-Cas9 knockin mice for genome editing and cancer modeling. Cell, vol. 159, pp. 440-455, Oct. 2014. (Year: 2014).*
Kosicki et al. Repair of double-strand breaks induced by CRISPR-Cas9 leads to large deletions and complex rearrangements. Nature Biotechnology, vol. 36, No. 8, pp. 765-771, and p. 1/1 of Online Methods, and pp. 1/10-10/10 of Supplementary Text and Figures, Jul. 31, 2018. (Year: 2018).*
Mondello et al. Panobinostat acts synergistically with ibrutinib in diffuse large B cell lymphoma cells with MyD88 L265P mutations. JCI Insight, vol. 2, No. 6, e90196, Mar. 23, 2017, printed as pp. 1-14, and pp. 1/14-14/14 of Supplemental Information. (Year: 2017).*
Boeke et al. The minimal repression domain of MBD2b overlaps with the methyl-CpG-binding domain and binds directly to Sin3A. The Journal of Biological Chemistry, vol. 275, No. 45, pp. 34963-34967, 2000. (Year: 2000).*
International Search Report issued for PCT/US2019/060285, dated Feb. 4, 2020.
Zhu, J., et al. The TLR9-MyD88 pathway is critical for adaptive immune responses to adeno-associated virus gene therapy vectors in mice. J Clin Invest 119, 2388-2398 (2009).
Anders, S. et al. Differential expression analysis for sequence count data. Genome biology 11, R106 (2010).
Bonizzi, G. et al. The two NF-kB activation pathways and their role in innate and adaptive immunity. Trends in immunology 25, 280-288 (2004).
Boutin, S. et al. Prevalence of serum IgG and neutralizing factors against adeno-associated virus (AAV) types 1, 2, 5, 6, 8, and 9 in the healthy population: implications for gene therapy using AAV vectors. Human gene therapy 21, 704-712 (2010).
Harvey, D.M. and Caskey, C. T. "Inducible control of gene expression: prospects for gene therapy." Current opinion in chemical biology 2.4 (1998): 512-518.
Charlesworth, C. T. et al. Identification of pre-existing adaptive immunity to Cas9 proteins in humans. BioRxiv, 243345 (2018).
Chen, S. et al. Efficient transduction of vascular endothelial cells with recombinant adeno-associated virus serotype 1 and 5 vectors. Human gene therapy 16, 235-247 (2005).
Chew, W. L. et al. A multifunctional AAV-CRISPR-Cas9 and its host response. Nature methods 13, 868 (2016).
Cho, S.-Y. et al. Biomarkers of sepsis. Infection & chemotherapy 46, 1-12 (2014).
Cook-Mills, J. M., et al. Vascular cell adhesion molecule-1 expression and signaling during disease: regulation by reactive oxygen species and antioxidants. Antioxidants & redox signaling 15, 1607-1638 (2011).
Dahlman, J. E. et al. "Orthogonal gene knockout and activation with a catalytically active Cas9 nuclease," Nature biotechnology 33, 1159 (2015).
Dandekar, A. et al. Toll-like receptor (TLR) signaling interacts with CREBH to modulate high-density lipoprotein (HDL) in response to bacterial endotoxin. Journal of Biological Chemistry 291, 23149-23158 (2016).
Ferdosi, S. R. et al. Multifunctional CRISPR/Cas9 with engineered immunosilenced human T cell epitopes. bioRxiv, 360198 (2018).
Ghosh, S., et al. NF-kB and Rel proteins: evolutionarily conserved mediators of immune responses. Annual review of immunology 16, 225-260 (1998).
Gossen, M. et al. "Tight control of gene expression in mammalian cells by tetracycline-responsive promoters." Proceedings of the National Academy of Sciences 89.12 (1992): 5547-5551.
Gossen, M. et al. "Transcriptional activation by tetracyclines in mammalian cells." Science 268.5218 (1995): 1766-1769.
Haft, D. H., et al. "A guild of 45 CRISPR-associated (Cas) protein families and multiple CRISPR/Cas subtypes exist in prokaryotic genomes." PLoS computational biology 1.6 (2005): e60.

Huang, X. et al. Targeting the TLR9-MyD88 pathway in the regulation of adaptive immune responses. Expert opinion on therapeutic targets 14, 787-796 (2010).
International Searching Authority. International Search Report and Written Opinion for application PCT/US2019/060285, dated Feb. 4, 2020.
Janssens, S. et al. A universal role for MyD88 in TLR/IL-1R-mediated signaling. Trends Biochem Sci 27, 474-482 (2002).
Kiani, S. et al. Cas9 gRNA engineering for genome editing, activation and repression. Nature methods 12, 1051 (2015).
Lee, K. M., et al. Isobavachalcone attenuates lipopolysaccharide-induced ICAM-1 expression in brain endothelial cells through blockade of toll-like receptor 4 signaling pathways. European journal of pharmacology 754, 11-18 (2015).
Li, Q. et al. NF-kB regulation in the immune system. Nature Reviews Immunology 2, 725 (2002).
Liao, H.-K. et al. In vivo target gene activation via CRISPR/Cas9-mediated trans-epigenetic modulation. Cell 171, 1495-1507. e1415 (2017).
Liao, H.-K. et al. Use of the CRISPR/Cas9 system as an intracellular defense against HIV-1 infection in human cells. Nature communications 6, 6413 (2015).
Lin, X., et al. Effect of TLR4/MyD88 signaling pathway on expression of IL-1beta and TNF-alpha in synovial fibroblasts from temporomandibular joint exposed to lipopolysaccharide. Mediators Inflamm 2015, 329405, doi:10.1155/2015/329405 (2015).
Liu, Y. et al. Directing cellular information flow via CRISPR signal conductors. Nature methods 13, 938 (2016).
Lu, Y. et al. Distinct immune responses to transgene products from rAAV1 and rAAV8 vectors. Proceedings of the National Academy of Sciences 106, 17158-17162 (2009).
Ma, X.-Y., et al. Early prevention of trauma-related infection/sepsis. Military Medical Research 3, 33 (2016).
Magari, S. R., et al. "Pharmacologic control of a humanized gene therapy system implanted into nude mice." The Journal of clinical investigation 100.11 (1997): 2865-2872.
Moreno, A. M. et al. In Situ Gene Therapy via AAV-CRISPR-Cas9-Mediated Targeted Gene Regulation. Mol Ther 26, 1818-1827, doi:10.1016/j.ymthe.2018.04.017 (2018).
Naso, M. F., et al. Adeno-associated virus (AAV) as a vector for gene therapy. BioDrugs 31, 317-334 (2017).
No, D. et al. "Ecdysone-inducible gene expression in mammalian cells and transgenic mice." Proceedings of the National Academy of Sciences 93.8 (1996): 3346-3351.
Park, G. S. et al. LPS Up-Regulates ICAM-1 Expression in Breast Cancer Cells by Stimulating a MyD88-BLT2-ERK-Linked Cascade, Which Promotes Adhesion to Monocytes. Mol Cells 38, 821-828, doi:10.14348/molcells.2015.0174 (2015).
Rogers, G. L. et al. Innate immune responses to AAV vectors. Frontiers in microbiology 2, 194 (2011).
Samulski, R. J. et al. AAV-mediated gene therapy for research and therapeutic purposes. Annual review of virology 1, 427-451 (2014).
Schnare, M. et al. Toll-like receptors control activation of adaptive immune responses. Nat Immunol 2, 947-950, doi:10.1038/ni712 (2001).
Senturk, S. et al. Rapid and tunable method to temporally control gene editing based on conditional Cas9 stabilization. Nature communications 8, 14370 (2017).
Sudres, M. et al. MyD88 signaling in B cells regulates the production of Th1-dependent antibodies to AAV. Mol Ther 20, 1571-1581, doi:10.1038/mt.2012.101 (2012).
Thakore, P. I. et al. RNA-guided transcriptional silencing in vivo with S. aureus CRISPR-Cas9 repressors. Nature communications 9 (2018).
Veron, P. et al. Major subsets of human dendritic cells are efficiently transduced by self-complementary adeno-associated virus vectors 1 and 2. J Virol 81, 5385-5394, doi:10.1128/JVI.02516-06 (2007).
Wang, Y., et al. "Positive and negative regulation of gene expression in eukaryotic cells with an inducible transcriptional regulator." Gene therapy 4.5 (1997): 432-441.
Wang, Y., et al. "Ligand-inducible and liver-specific target gene expression in transgenic mice." Nature biotechnology 15.3 (1997): 239-243.

(56) References Cited

OTHER PUBLICATIONS

Warner, N. et al. MyD88: a critical adaptor protein in innate immunity signal transduction. J Immunol 190, 3-4, doi:10.4049/jimmunol.1203103 (2013).

Yao, Z. et al. Blood-borne lipopolysaccharide is rapidly eliminated by liver sinusoidal endothelial cells via high-density lipoprotein. The Journal of Immunology 197, 2390-2399 (2016).

Yeo, N. C. et al. An enhanced CRISPR repressor for targeted mammalian gene regulation. Nature methods 15, 611 (2018).

Yu, G., et al. clusterProfiler: an R package for comparing biological themes among gene clusters. Omics: a journal of integrative biology 16, 284-287 (2012).

Yu, M. et al. MyD88-dependent interplay between myeloid and endothelial cells in the initiation and progression of obesity-associated inflammatory diseases. J Exp Med 211, 887-907, doi:10.1084/jem.20131314 (2014).

Zhang, H. et al. Sepsis induces hematopoietic stem cell exhaustion and myelosuppression through distinct contributions of TRIF and MYD88. Stem cell reports 6, 940-956 (2016).

Zheng, Y. et al. CRISPR interference-based specific and efficient gene inactivation in the brain. Nat Neurosci 21, 447-454, doi:10.1038/s41593-018-0077-5 (2018).

Zhou, H. et al. In vivo simultaneous transcriptional activation of multiple genes in the brain using CRISPR-dCas9-activator transgenic mice. Nat Neurosci 21, 440-446, doi:10.1038/s41593-017-0060-6 (2018).

Gais, et al: "Cutting Edge: Divergent Cell-Specific Functions of MyD88 for Inflammatory Responses and Organ Injury in Septic Peritonitis", The Journal of Immunology, vol. 188, No. 12, Jun. 15, 2012.

Kiani, "CRISPR-based transcriptional repression to perform immunomodulation in vivo Myd88 Lung Blood Bone Marrow", Nov. 1, 2020.

Moghadam, et al: "Synthetic immunomodulation with a CRISPR super-repressor in vivo", Nature Cell Biology, Nature Publishing Group UK, London, vol. 22, No. 9, Sep. 1, 2020.

Pineda, et al: "Engineered CRISPR Systems for Next Generation Gene Therapies", ACS Synthetic Biology, vol. 6, No. 9, Jun. 7, 2017.

Plant, et al: "MyD88-Dependent Signaling Affects the Development of Meningococcal Sepsis by Nonlipooligosaccharide Ligands", Infection and Immunity, vol. 74, No. 6, Jun. 1, 2006.

Samba-Mondonga, et al: "MyD88 Regulates the Expression of SMAD4 and the Iron Regulatory Hormone Hepcidin", Frontiers in Cell and Developmental Biology, vol. 6, Aug. 13, 2018.

European Search Report issued in corresponding EP Application No. 19881214, dated Jul. 15, 2022.

\* cited by examiner

```
                        SEQUENCE LISTING

<160> NUMBER OF SEQ ID NOS: 66

<210> SEQ ID NO 1
<211> LENGTH: 14
<212> TYPE: DNA
<213> ORGANISM: Artificial Sequence
<220> FEATURE:
<223> OTHER INFORMATION: synthetic

<400> SEQUENCE: 1
gcctagtcca tcca                                                   14

<210> SEQ ID NO 2
<211> LENGTH: 14
<212> TYPE: DNA
```

```
<213> ORGANISM: Artificial Sequence
<220> FEATURE:
<223> OTHER INFORMATION: synthetic

<400> SEQUENCE: 2
ccaccgatca aggt                                                         14

<210> SEQ ID NO 3
<211> LENGTH: 14
<212> TYPE: DNA
<213> ORGANISM: Artificial Sequence
<220> FEATURE:
<223> OTHER INFORMATION: synthetic

<400> SEQUENCE: 3
gcgagcgtac tgga                                                         14

<210> SEQ ID NO 4
<211> LENGTH: 14
<212> TYPE: DNA
<213> ORGANISM: Artificial Sequence
<220> FEATURE:
<223> OTHER INFORMATION: synthetic

<400> SEQUENCE: 4
gtggacggca ccgg                                                         14

<210> SEQ ID NO 5
<211> LENGTH: 14
<212> TYPE: DNA
<213> ORGANISM: Artificial Sequence
<220> FEATURE:
<223> OTHER INFORMATION: synthetic

<400> SEQUENCE: 5
agcttaggga taac                                                         14

<210> SEQ ID NO 6
<211> LENGTH: 14
<212> TYPE: DNA
<213> ORGANISM: Artificial Sequence
<220> FEATURE:
<223> OTHER INFORMATION: synthetic

<400> SEQUENCE: 6
ataaaagtcc ggtt                                                         14

<210> SEQ ID NO 7
<211> LENGTH: 14
<212> TYPE: DNA
<213> ORGANISM: Artificial Sequence
<220> FEATURE:
<223> OTHER INFORMATION: synthetic

<400> SEQUENCE: 7
tccggtaacc acca                                                         14

<210> SEQ ID NO 8
<211> LENGTH: 22
<212> TYPE: DNA
<213> ORGANISM: Artificial Sequence
<220> FEATURE:
<223> OTHER INFORMATION: synthetic

<400> SEQUENCE: 8
ggcaggaaga gcagcggcga gg                                                22
```

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9 gggggcgga tactgacccg                                                    20

<210> SEQ ID NO 10
<211> LENGTH: 22
<212> TYPE: DNA
<213> ORGANISM: Artificial Sequence
<220> FEATURE:
<223> OTHER INFORMATION: synthetic

<400> SEQUENCE: 10
ggatactgac ccgaggacgc cg                                                22

<210> SEQ ID NO 11
<211> LENGTH: 22
<212> TYPE: DNA
<213> ORGANISM: Artificial Sequence
<220> FEATURE:
<223> OTHER INFORMATION: synthetic

<400> SEQUENCE: 11
gggcgctggg ttcctggtga gt                                                22

<210> SEQ ID NO 12
<211> LENGTH: 20
<212> TYPE: DNA
<213> ORGANISM: Artificial Sequence
<220> FEATURE:
<223> OTHER INFORMATION: synthetic

<400> SEQUENCE: 12
ggttgcgggc gtcgcaggca                                                   20

<210> SEQ ID NO 13
<211> LENGTH: 21
<212> TYPE: DNA
<213> ORGANISM: Artificial Sequence
<220> FEATURE:
<223> OTHER INFORMATION: synthetic

<400> SEQUENCE: 13
ggcaccggcg tctgaggtct c                                                 21

<210> SEQ ID NO 14
<211> LENGTH: 23
<212> TYPE: DNA
<213> ORGANISM: Artificial Sequence
<220> FEATURE:
<223> OTHER INFORMATION: synthetic

<400> SEQUENCE: 14
ggcgacaggg agggatgcgc gcc                                               23

<210> SEQ ID NO 15
<211> LENGTH: 21
<212> TYPE: DNA
<213> ORGANISM: Artificial Sequence
<220> FEATURE:

```
<223> OTHER INFORMATION: synthetic

<400> SEQUENCE: 15
ggcgcgcctg ggtgtagttg t                                              21

<210> SEQ ID NO 16
<211> LENGTH: 23
<212> TYPE: DNA
<213> ORGANISM: Artificial Sequence
<220> FEATURE:
<223> OTHER INFORMATION: synthetic

<400> SEQUENCE: 16
ggaagtggct agctcagggc ttc                                            23

<210> SEQ ID NO 17
<211> LENGTH: 21
<212> TYPE: DNA
<213> ORGANISM: Artificial Sequence
<220> FEATURE:
<223> OTHER INFORMATION: synthetic

<400> SEQUENCE: 17
ggcagcgctt taagaactga a                                              21

<210> SEQ ID NO 18
<211> LENGTH: 23
<212> TYPE: DNA
<213> ORGANISM: Artificial Sequence
<220> FEATURE:
<223> OTHER INFORMATION: synthetic

<400> SEQUENCE: 18
ggactgaaga tctctctgca ctt                                            23

<210> SEQ ID NO 19
<211> LENGTH: 22
<212> TYPE: DNA
<213> ORGANISM: Artificial Sequence
<220> FEATURE:
<223> OTHER INFORMATION: synthetic

<400> SEQUENCE: 19
ggccatattt cttactctct cg                                             22

<210> SEQ ID NO 20
<211> LENGTH: 22
<212> TYPE: DNA
<213> ORGANISM: Artificial Sequence
<220> FEATURE:
<223> OTHER INFORMATION: synthetic

<400> SEQUENCE: 20
gcaggtagca aagtgacgcc ga                                             22

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
caaccactac ctgagcaccc                                                20
```

```
<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
gtccatgccg agagtgatcc                                              20

<210> SEQ ID NO 23
<211> LENGTH: 23
<212> TYPE: DNA
<213> ORGANISM: Artificial Sequence
<220> FEATURE:
<223> OTHER INFORMATION: synthetic

<400> SEQUENCE: 23
gtgaggatat actgaaggag ctg                                          23

<210> SEQ ID NO 24
<211> LENGTH: 21
<212> TYPE: DNA
<213> ORGANISM: Artificial Sequence
<220> FEATURE:
<223> OTHER INFORMATION: synthetic

<400> SEQUENCE: 24
ctgtaaaggc ttctcggact c                                            21

<210> SEQ ID NO 25
<211> LENGTH: 23
<212> TYPE: DNA
<213> ORGANISM: Artificial Sequence
<220> FEATURE:
<223> OTHER INFORMATION: synthetic

<400> SEQUENCE: 25
cctgacattc ccaaagacaa agc                                          23

<210> SEQ ID NO 26
<211> LENGTH: 22
<212> TYPE: DNA
<213> ORGANISM: Artificial Sequence
<220> FEATURE:
<223> OTHER INFORMATION: synthetic

<400> SEQUENCE: 26
tctctcagca cagcatatgc ac                                           22

<210> SEQ ID NO 27
<211> LENGTH: 20
<212> TYPE: DNA
<213> ORGANISM: Artificial Sequence
<220> FEATURE:
<223> OTHER INFORMATION: synthetic

<400> SEQUENCE: 27
gaccatggct gggattcacc                                              20

<210> SEQ ID NO 28
<211> LENGTH: 20
<212> TYPE: DNA
<213> ORGANISM: Artificial Sequence
<220> FEATURE:
<223> OTHER INFORMATION: synthetic
```

<400> SEQUENCE: 28
ccaagggagc ttcagggtca                                          20

<210> SEQ ID NO 29
<211> LENGTH: 25
<212> TYPE: DNA
<213> ORGANISM: Artificial Sequence
<220> FEATURE:
<223> OTHER INFORMATION: synthetic

<400> SEQUENCE: 29
ggactttgga ttcccgcagg agaag                                    25

<210> SEQ ID NO 30
<211> LENGTH: 25
<212> TYPE: DNA
<213> ORGANISM: Artificial Sequence
<220> FEATURE:
<223> OTHER INFORMATION: synthetic

<400> SEQUENCE: 30
gctgcatcag acagccttgc aggtc                                    25

<210> SEQ ID NO 31
<211> LENGTH: 20
<212> TYPE: DNA
<213> ORGANISM: Artificial Sequence
<220> FEATURE:
<223> OTHER INFORMATION: synthetic

<400> SEQUENCE: 31
caatttctca tgccgcacag                                          20

<210> SEQ ID NO 32
<211> LENGTH: 21
<212> TYPE: DNA
<213> ORGANISM: Artificial Sequence
<220> FEATURE:
<223> OTHER INFORMATION: synthetic

<400> SEQUENCE: 32
agctggaaga tcgaaagtcc g                                        21

<210> SEQ ID NO 33
<211> LENGTH: 18
<212> TYPE: DNA
<213> ORGANISM: Artificial Sequence
<220> FEATURE:
<223> OTHER INFORMATION: synthetic

<400> SEQUENCE: 33
aggctgcccc gactacgt                                            18

<210> SEQ ID NO 34
<211> LENGTH: 27
<212> TYPE: DNA
<213> ORGANISM: Artificial Sequence
<220> FEATURE:
<223> OTHER INFORMATION: synthetic

<400> SEQUENCE: 34
gactttctcc tggtatgaga tagcaaa                                  27

<210> SEQ ID NO 35
<211> LENGTH: 21

```
<212> TYPE: DNA
<213> ORGANISM: Artificial Sequence
<220> FEATURE:
<223> OTHER INFORMATION: synthetic

<400> SEQUENCE: 35
gctgcgtgaa cactatcctg g                                                    21

<210> SEQ ID NO 36
<211> LENGTH: 23
<212> TYPE: DNA
<213> ORGANISM: Artificial Sequence
<220> FEATURE:
<223> OTHER INFORMATION: synthetic

<400> SEQUENCE: 36
aggtcgtact tctccattct gta                                                  23

<210> SEQ ID NO 37
<211> LENGTH: 23
<212> TYPE: DNA
<213> ORGANISM: Artificial Sequence
<220> FEATURE:
<223> OTHER INFORMATION: synthetic

<400> SEQUENCE: 37
ggccgttctt agttggtgga gcg                                                  23

<210> SEQ ID NO 38
<211> LENGTH: 20
<212> TYPE: DNA
<213> ORGANISM: Artificial Sequence
<220> FEATURE:
<223> OTHER INFORMATION: synthetic

<400> SEQUENCE: 38
ctgaacgcca cttgtccctc                                                      20

<210> SEQ ID NO 39
<211> LENGTH: 17
<212> TYPE: DNA
<213> ORGANISM: Artificial Sequence
<220> FEATURE:
<223> OTHER INFORMATION: synthetic

<400> SEQUENCE: 39
tgcggctccc tgtgtgt                                                         17

<210> SEQ ID NO 40
<211> LENGTH: 23
<212> TYPE: DNA
<213> ORGANISM: Artificial Sequence
<220> FEATURE:
<223> OTHER INFORMATION: synthetic

<400> SEQUENCE: 40
tcttcctctg ttccttgggc tat                                                  23

<210> SEQ ID NO 41
<211> LENGTH: 20
<212> TYPE: DNA
<213> ORGANISM: Artificial Sequence
<220> FEATURE:
<223> OTHER INFORMATION: synthetic

<400> SEQUENCE: 41
```
gctcagtcat cagcaactcg                                                          20

<210> SEQ ID NO 42
<211> LENGTH: 18
<212> TYPE: DNA
<213> ORGANISM: Artificial Sequence
<220> FEATURE:
<223> OTHER INFORMATION: synthetic

<400> SEQUENCE: 42
tcacaggcga agtccatc                                                            18

<210> SEQ ID NO 43
<211> LENGTH: 19
<212> TYPE: DNA
<213> ORGANISM: Artificial Sequence
<220> FEATURE:
<223> OTHER INFORMATION: synthetic

<400> SEQUENCE: 43
gagagtcagc ggagttctc                                                           19

<210> SEQ ID NO 44
<211> LENGTH: 22
<212> TYPE: DNA
<213> ORGANISM: Artificial Sequence
<220> FEATURE:
<223> OTHER INFORMATION: synthetic

<400> SEQUENCE: 44
ctcacaggtc aaagtattgt tg                                                       22

<210> SEQ ID NO 45
<211> LENGTH: 20
<212> TYPE: DNA
<213> ORGANISM: Artificial Sequence
<220> FEATURE:
<223> OTHER INFORMATION: synthetic

<400> SEQUENCE: 45
tcgctcaggg tcacaagaaa                                                          20

<210> SEQ ID NO 46
<211> LENGTH: 22
<212> TYPE: DNA
<213> ORGANISM: Artificial Sequence
<220> FEATURE:
<223> OTHER INFORMATION: synthetic

<400> SEQUENCE: 46
catcagaggc aaggaggaaa ac                                                       22

<210> SEQ ID NO 47
<211> LENGTH: 20
<212> TYPE: DNA
<213> ORGANISM: Artificial Sequence
<220> FEATURE:
<223> OTHER INFORMATION: synthetic

<400> SEQUENCE: 47
gtggctgttg gagtcggtat                                                          20

<210> SEQ ID NO 48
<211> LENGTH: 20
<212> TYPE: DNA
<213> ORGANISM: Artificial Sequence -continued

```
<220> FEATURE:
<223> OTHER INFORMATION: synthetic

<400> SEQUENCE: 48
attcactccc caccctctct                                               20

<210> SEQ ID NO 49
<211> LENGTH: 20
<212> TYPE: DNA
<213> ORGANISM: Artificial Sequence
<220> FEATURE:
<223> OTHER INFORMATION: synthetic

<400> SEQUENCE: 49
aggtcaggca gaggaagtca                                               20

<210> SEQ ID NO 50
<211> LENGTH: 20
<212> TYPE: DNA
<213> ORGANISM: Artificial Sequence
<220> FEATURE:
<223> OTHER INFORMATION: synthetic

<400> SEQUENCE: 50
ctgcctcccg atacaacaat                                               20

<210> SEQ ID NO 51
<211> LENGTH: 20
<212> TYPE: DNA
<213> ORGANISM: Artificial Sequence
<220> FEATURE:
<223> OTHER INFORMATION: synthetic

<400> SEQUENCE: 51
aggtcaggca gaggaagtca                                               20

<210> SEQ ID NO 52
<211> LENGTH: 20
<212> TYPE: DNA
<213> ORGANISM: Artificial Sequence
<220> FEATURE:
<223> OTHER INFORMATION: synthetic

<400> SEQUENCE: 52
ctgcctcccg atacaacaat                                               20

<210> SEQ ID NO 53
<211> LENGTH: 20
<212> TYPE: DNA
<213> ORGANISM: Artificial Sequence
<220> FEATURE:
<223> OTHER INFORMATION: synthetic

<400> SEQUENCE: 53
accagcatcc ctagctcaga                                               20

<210> SEQ ID NO 54
<211> LENGTH: 20
<212> TYPE: DNA
<213> ORGANISM: Artificial Sequence
<220> FEATURE:
<223> OTHER INFORMATION: synthetic

<400> SEQUENCE: 54
tcctcaggca tctcctctgt                                               20
```

<210> SEQ ID NO 55
<211> LENGTH: 1634
<212> TYPE: DNA
<213> ORGANISM: Artificial Sequence
<220> FEATURE:
<223> OTHER INFORMATION: synthetic

<400> SEQUENCE: 55

| | | | | | |
|---|---|---|---|---|---|
| ccaccatggg | acctaagaaa | aagaggaagg | tggcggccgc | tgactacaag | gatgacgacg | 60 |
| ataaatctag | aatggcttct | aactttactc | agttcgttct | cgtcgacaat | ggcggaactg | 120 |
| gcgacgtgac | tgtcgcccca | agcaacttcg | ctaacgggat | cgctgaatgg | atcagctcta | 180 |
| actcgcgttc | acaggcttac | aaagtaacct | gtagcgttcg | tcagagctct | gcgcagaatc | 240 |
| gcaaatacac | catcaaagtc | gaggtgccta | aaggcgcctg | gcgttcgtac | ttaaatatgg | 300 |
| aactaaccat | tccaattttc | gccacgaatt | ccgactgcga | gcttattgtt | aaggcaatgc | 360 |
| aaggtctcct | aaaagatgga | aacccgattc | cctcagcaat | cgcagcaaac | tccggcatct | 420 |
| acgaggccag | ccccaagaag | aagaggaagg | tgagtggtgg | aggaagtggc | gggtcagggt | 480 |
| cgtccatgga | cgcgaaatca | cttacggcat | ggtcgagaac | actggttacg | ttcaaggacg | 540 |
| tgtttgtgga | ctttacacgt | gaggagtgga | aattgctgga | tactgcgcaa | caaattgtgt | 600 |
| atcgaaatgt | catgcttgag | aattacaaga | acctcgtcag | tctcggatac | cagttgacga | 660 |
| aaccggatgt | gatccttagg | ctcgaaaagg | gggaagaacc | ttggctggta | tcggaggtg | 720 |
| gttcgggtgg | ctctggatca | agcccaaaga | agaaacggaa | ggtggaagcc | tcagtgcagg | 780 |
| tgaaaagggt | gctggaaaaa | tcccccggca | aactcctcgt | gaagatgccc | ttccaggctt | 840 |
| cccctggcgg | aaaaggtgaa | gggggtggcg | caaccacatc | tgcccaggtc | atggtcatca | 900 |
| agcgacctgg | aagaaaaga | aaggccgagg | ctgaccctca | ggccattcca | agaaacggg | 960 |
| gacgcaagcc | agggtccgtg | gtcgcagctg | cagcagctga | ggctaagaaa | aaggcagtga | 1020 |
| aggaaagctc | catccgcagt | gtgcaggaga | ctgtcctgcc | catcaagaag | aggaagacta | 1080 |
| gggagaccgt | gtccatcgag | gtcaaagaag | tggtcaagcc | cctgctcgtg | tccaccctgg | 1140 |
| gcgaaaaatc | tggaaagggg | ctcaaaaacat | gcaagtcacc | tggacggaaa | agcaaggagt | 1200 |
| ctagtccaaa | ggggcgctca | agctccgctt | ctagtccccc | taaaaaggaa | caccatcacc | 1260 |
| atcaccatca | cgccgagtct | cctaaggctc | ctatgccact | gctcccacca | cctccaccac | 1320 |
| ctgagccaca | gtcaagcgaa | gaccccatca | gcccacccga | gcctcaggat | ctgtcctcta | 1380 |
| gtatttgcaa | agaggaaaag | atgcccgag | caggcagcct | ggagagtgat | ggctgtccaa | 1440 |
| aagaacccgc | caagacccag | cctatggtgg | cagccgctgc | aactaccacc | acaaccacaa | 1500 |
| ctaccacagt | ggccgaaaaa | tacaagcatc | gcggcgaggg | cgaacgaaag | gacattgtgt | 1560 |
| caagctccat | gcccagacct | aaccgggagg | aaccagtcga | tagtaggaca | cccgtgactg | 1620 |
| agagagtctc | atga | | | | | 1634 |

<210> SEQ ID NO 56
<211> LENGTH: 399
<212> TYPE: DNA
<213> ORGANISM: Artificial Sequence
<220> FEATURE:
<223> OTHER INFORMATION: synthetic

<400> SEQUENCE: 56

| | | | | | |
|---|---|---|---|---|---|
| gcggccgctg | actacaagga | tgacgacgat | aaatctagaa | tggcttctaa | ctttactcag | 60 |
| ttcgttctcg | tcgacaatgg | cggaactggc | gacgtgactg | tcgccccaag | caacttcgct | 120 |

```
aacgggatcg ctgaatggat cagctctaac tcgcgttcac aggcttacaa agtaacctgt    180
agcgttcgtc agagctctgc gcagaatcgc aaatacacca tcaaagtcga ggtgcctaaa    240
ggcgcctggc gttcgtactt aaatatggaa ctaaccattc caattttcgc cacgaattcc    300
gactgcgagc ttattgttaa ggcaatgcaa ggtctcctaa agatggaaa cccgattccc     360 tcagcaatcg cagcaaactc cggcatctac gaggccagc                           399
```

<210> SEQ ID NO 57
<211> LENGTH: 225
<212> TYPE: DNA
<213> ORGANISM: Artificial Sequence
<220> FEATURE:
<223> OTHER INFORMATION: synthetic

<400> SEQUENCE: 57

```
atggacgcga atcacttac ggcatggtcg agaacactgg ttacgttcaa ggacgtgttt      60
gtggacttta cacgtgagga gtggaaattg ctggatactg cgcaacaaat tgtgtatcga    120
aatgtcatgc ttgagaatta caagaacctc gtcagtctcg gataccagtt gacgaaaccg    180
gatgtgatcc ttaggctcga aaaggggaa gaaccttggc tggta                     225
```

<210> SEQ ID NO 58
<211> LENGTH: 891
<212> TYPE: DNA
<213> ORGANISM: Artificial Sequence
<220> FEATURE:
<223> OTHER INFORMATION: synthetic

<400> SEQUENCE: 58

```
agcccaaaga agaaacggaa ggtggaagcc tcagtgcagg tgaaaagggt gctggaaaaa     60
tcccccggca aactcctcgt gaagatgccc ttccaggctt cccctggcgg aaaaggtgaa    120
gggggtggcg caaccacatc tgcccaggtc atggtcatca agcgacctgg aaggaaaaga    180
aaggccgagg ctgaccctca ggccattcca agaaacggg gacgcaagcc agggtccgtg    240
gtcgcagctg cagcagctga ggctaagaaa aaggcagtga aggaaagctc catccgcagt    300
gtgcaggaga ctgtcctgcc catcaagaag aggaagacta gggagaccgt gtccatcgag    360
gtcaaagaag tggtcaagcc cctgctcgtg tccaccctgg gcgaaaaatc tggaaagggg    420
ctcaaaacat gcaagtcacc tggacggaaa agcaaggagt ctagtccaaa ggggcgctca    480
agctccgctt ctagtccccc taaaaaggaa caccatcacc atcaccatca cgccgagtct    540
cctaaggctc ctatgccact gctcccacca cctccaccac ctgagccaca gtcaagcgaa    600
gaccccatca gcccacccga gcctcaggat ctgtcctcta gtatttgcaa agaggaaaag    660
atgcccagag caggcagcct ggagagtgat ggctgtccaa agaacccgc caagacccag    720 cctatggtgg cagccgctgc aactaccacc acaaccacaa ctaccacagt ggccgaaaaa    780
tacaagcatc gcggcgaggg cgaacgaaag gacattgtgt caagctccat gcccagacct    840
aaccgggagg aaccagtcga tagtaggaca cccgtgactg agagagtctc a             891
```

<210> SEQ ID NO 59
<211> LENGTH: 1134
<212> TYPE: DNA
<213> ORGANISM: Artificial Sequence
<220> FEATURE:
<223> OTHER INFORMATION: synthetic

<400> SEQUENCE: 59

```
ccaccatggg acctaagaaa agaggaagg tggcggccgc tgactacaag gatgacgacg      60
ataaatctag aatggcttct aactttactc agttcgttct cgtcgacaat ggcggaactg     120
gcgacgtgac tgtcgcccca agcaacttcg ctaacgggat cgctgaatgg atcagctcta    180
actcgcgttc acaggcttac aaagtaacct gtagcgttcg tcagagctct gcgcagaatc    240
gcaaatacac catcaaagtc gaggtgccta aaggcgcctg gcgttcgtac ttaaatatgg    300
aactaaccat tccaattttc gccacgaatt ccgactgcga gcttattgtt aaggcaatgc    360
aaggtctcct aaaagatgga aacccgattc cctcagcaat cgcagcaaac tccggcatct    420
acgaggccag ccccaagaag aagaggaagg tgagtggtgg aggaagtggc gggtcagggt    480
cgtccagccc caagaaaaaa cggaaagtgg aggcatcaat gaaggaggga gaaaacaaca    540
aacccaggga gaaagtgaaa gggaataaga gaaaaagctc cttctctaac agtgcagacg    600
atatcaagtc caagaaaaag cgggagcagt ctaatgacat tgctaggggc ttcgagagag    660
gactggagcc agaaaaaatc attggggcaa ccgacagctg cggcgatctg atgtttctca    720
tgaaatggaa ggacacagat gaggccgacc tggtgctcgc caaagaagct aacgtgaagt    780
gtccccagat cgtcattgct ttttacgagg aaaggctcac ctggcacgca tatcctgagg    840
atgccgaaaa caaggagaag gaatcagcta agagcctcgg gaggtggttc gggtggctct    900
ggatcaatgg acgcgaaatc acttacggca tggtcgagaa cactggttac gttcaaggac    960
gtgtttgtgg actttacacg tgaggagtgg aaattgctgg atactgcgca acaaattgtg   1020
tatcgaaatg tcatgcttga gaattacaag aacctcgtca gtctcggata ccagttgacg   1080
aaaccggatg tgatccttag gctcgaaaag ggggaagaac cttggctggt atga         1134

<210> SEQ ID NO 60
<211> LENGTH: 390
<212> TYPE: DNA
<213> ORGANISM: Artificial Sequence
<220> FEATURE:
<223> OTHER INFORMATION: synthetic

<400> SEQUENCE: 60
agccccaaga aaaacggaa agtggaggca tcaatgaagg agggagaaaa caacaaaccc      60
agggagaaaa gtgaagggaa taagagaaaa agctccttct ctaacagtgc agacgatatc    120
aagtccaaga aaaagcggga gcagtctaat gacattgcta ggggcttcga gagaggactg    180
agccagaaaa aaatcattgg ggcaaccgac agctgcggcg atctgatgtt tctcatgaaa    240
tggaaggaca cagatgaggc cgacctggtg ctcgccaaag aagctaacgt gaagtgtccc    300
cagatcgtca ttgcttttta cgaggaaagg ctcacctggc acgcatatcc tgaggatgcc    360
gaaaacaagg agaaggaatc agctaagagc                                     390

<210> SEQ ID NO 61
<211> LENGTH: 2351
<212> TYPE: DNA
<213> ORGANISM: Artificial Sequence
<220> FEATURE:
<223> OTHER INFORMATION: synthetic

<400> SEQUENCE: 61
ccaccatggg acctaagaaa agaggaagg tggcggccgc tgactacaag gatgacgacg      60
ataaatctag aatggcttct aactttactc agttcgttct cgtcgacaat ggcggaactg    120
gcgacgtgac tgtcgcccca agcaacttcg ctaacgggat cgctgaatgg atcagctcta    180
actcgcgttc acaggcttac aaagtaacct gtagcgttcg tcagagctct gcgcagaatc    240
```

```
gcaaatacac catcaaagtc gaggtgccta aaggcgcctg gcgttcgtac ttaaatatgg    300
aactaaccat tccaattttc gccacgaatt ccgactgcga gcttattgtt aaggcaatgc    360
aaggtctcct aaaagatgga aacccgattc cctcagcaat cgcagcaaac tccggcatct    420
acgaggccag ccccaagaag aagaggaagg tgagtggtgg aggaagtggc gggtcagggt    480
cgtccagccc aaagaagaaa cggaaggtgg aagcctcagt gcaggtgaaa agggtgctgg    540
aaaaatcccc cggcaaactc ctcgtgaaga tgcccttcca ggcttcccct ggcggaaaag    600 gtgaagggg tggcgcaacc acatctgccc aggtcatggt catcaagcga cctggaagga    660
aaagaaaggc cgaggctgac cctcaggcca ttccaaagaa cgggacgc aagccagggt    720 ccgtggtcgc agctgcagca gctgaggcta agaaaaaggc agtgaaggaa agctccatcc    780
gcagtgtgca ggagactgtc ctgcccatca agaagaggaa gactagggag accgtgtcca    840
tcgaggtcaa agaagtggtc aagcccctgc tcgtgtccac cctgggcgaa aaatctggaa    900
aggggctcaa aacatgcaag tcacctggac ggaaaagcaa ggagtctagt ccaaaggggc    960
gctcaagctc cgcttctagt cccctaaaa aggaacacca tcaccatcac catcacgccg    1020
agtctcctaa ggctcctatg ccactgctcc caccacctcc accacctgag ccacagtcaa    1080
gcgaagaccc catcagccca cccgagcctc aggatctgtc ctctagtatt tgcaaagagg    1140
aaaagatgcc cagagcaggc agcctggaga gtgatggctg tccaaaagaa cccgccaaga    1200
cccagcctat ggtggcagcc gctgcaacta ccaccacaac cacaactacc acagtggccg    1260
aaaaatacaa gcatcgcggc gagggcgaac gaaaggacat tgtgtcaagc tccatgccca    1320
gacctaaccg ggaggaacca gtcgatagta ggacacccgt gactgagaga gtctcatcgg    1380
gaggtggttc gggtggctct ggatcaatgg acgcgaaatc acttacgca tggtcgagaa    1440 cactggttac gttcaaggac gtgtttgtgg actttacacg tgaggagtgg aaattgctgg    1500
atactgcgca acaaattgtg tatcgaaatg tcatgcttga gaattacaag aacctcgtca    1560
gtctcggata ccagttgacg aaaccggatg tgatccttag gctcgaaaag ggggaagaac    1620
cttggctggt atcgggaggt ggttcgggtg gctctggatc atccccaaa agaaacgca    1680 aggtgaggca tctgctcgct atctcggtaa cactgtcgat ctgtcatcat tcgatttccg    1740
cactggcaag atgatgcctt ctaaactgca gaagaacaaa cagaggctga gaaatgaccc    1800
actcaaccag aataagggaa aacccgatct gaacaccaca ctccctatcc ggcagacagc    1860
tagtattttc aagcagcctg tgactaaagt caccaaccac ccatccaata aggtgaaatc    1920
tgacccacag aggatgaatg agcagcccag acagctgttt tgggaaaagc gcctgcaggg    1980
tctctctgca agtgatgtga cagagcagat cattaagact atggaactgc aaaaggact     2040 ccagggagtg ggacctgggt ctaacgacga gactctgctc tcagctgtcg caagcgcact    2100
gcataccagc tccgcaccca tcacaggaca ggtgagtgcc gctgtcgaga gaacccagc    2160 cgtgtggctc aatacttcac agcccctctg caaggcttc atcgtcaccg acgaggatat    2220
tcggaagcag gaggaacgcg tgcagcaggt ccgaaaaatc ctggaagacg ctctcatggc    2280
agatattctg agcagagcag ccgacaccga ggaaatggat attgagatgg actccgggga    2340
tgaagcctga a                                                        2351
```

<210> SEQ ID NO 62
<211> LENGTH: 633
<212> TYPE: DNA
<213> ORGANISM: Artificial Sequence
<220> FEATURE:

<223> OTHER INFORMATION: synthetic

<400> SEQUENCE: 62

| aggcatctgc tcgctatctc ggtaacactg tcgatctgtc atcattcgat ttccgcactg | 60 |
| gcaagatgat gccttctaaa ctgcagaaga acaaacagag gctgagaaat gacccactca | 120 |
| accagaataa gggaaaaccc gatctgaaca ccacactccc tatccggcag acagctagta | 180 |
| ttttcaagca gcctgtgact aaagtcacca accacccatc caataaggtg aaatctgacc | 240 |
| cacagaggat gaatgagcag cccagacagc tgttttggga aaagcgcctg cagggtctct | 300 |
| ctgcaagtga tgtgacagag cagatcatta agactatgga actgccaaaa ggactccagg | 360 |
| gagtgggacc tgggtctaac gacgagactc tgctctcagc tgtcgcaagc gcactgcata | 420 |
| ccagctccgc acccatcaca ggacaggtga gtgccgctgt cgagaagaac ccagccgtgt | 480 |
| ggctgaatac ttcacagccc ctctgcaagg cttttcatcgt caccgacgag gatattcgga | 540 |
| agcaggagga acgcgtgcag caggtccgaa aaatcctgga agacgctctc atggcagata | 600 |
| ttctgagcag agcagccgac accgaggaaa tgg | 633 |

<210> SEQ ID NO 63
<211> LENGTH: 1595
<212> TYPE: DNA
<213> ORGANISM: Artificial Sequence
<220> FEATURE:
<223> OTHER INFORMATION: synthetic

<400> SEQUENCE: 63

| ccaccatggg acctaagaaa aagaggaagg tggcggccgc tgactacaag gatgacgacg | 60 |
| ataaatctag aatggcttct aactttactc agttcgttct cgtcgacaat ggcggaactg | 120 |
| gcgacgtgac tgtcgcccca agcaacttcg ctaacgggat cgctgaatgg atcagctcta | 180 |
| actcgcgttc acaggcttac aaagtaacct gtagcgttcg tcagagctct gcgcagaatc | 240 |
| gcaaatacac catcaaagtc gaggtgccta aaggcgcctg gcgttcgtac ttaaatatgg | 300 |
| aactaaccat tccaattttc gccacgaatt ccgactgcga gcttattgtt aaggcaatgc | 360 |
| aaggtctcct aaaagatgga aacccgattc cctcagcaat cgcagcaaac tccggcatct | 420 |
| acgaggccag ccccaagaag aagaggaagg tgagtggtgg aggaagtggc gggtcagggt | 480 |
| cgtcctcccc caaaaagaaa cgcaaggtgg aggcatctgc tcgctatctc ggtaacactg | 540 |
| tcgatctgtc atcattcgat ttccgcactg gcaagatgat gccttctaaa ctgcagaaga | 600 |
| acaaacagag gctgagaaat gacccactca accagaataa gggaaaaccc gatctgaaca | 660 |
| ccacactccc tatccggcag acagctagta ttttcaagca gcctgtgact aaagtcacca | 720 |
| accacccatc caataaggtg aaatctgacc cacagaggat gaatgagcag cccagacagc | 780 |
| tgttttggga aaagcgcctg cagggtctct ctgcaagtga tgtgacagag cagatcatta | 840 |
| agactatgga actgccaaaa ggactccagg gagtgggacc tgggtctaac gacgagactc | 900 |
| tgctctcagc tgtcgcaagc gcactgcata ccagctccgc acccatcaca ggacaggtga | 960 |
| gtgccgctgt cgagaagaac ccagccgtgt ggctgaatac ttcacagccc ctctgcaagg | 1020 |
| cttttcatcgt caccgacgag gatattcgga agcaggagga acgcgtgcag caggtccgaa | 1080 |
| aaatcctgga agacgctctc atggcagata ttctgagcag agcagccgac accgaggaaa | 1140 |
| tggatattga gatggactcc gggatgaag cctcggagg tggttcgggt ggctctggat | 1200 |
| caagcccca gaaaaacgg aaagtggagg catcaatgaa ggagggagaa acaacaaac | 1260 |
| ccagggagaa aagtgaaggg aataagagaa aaagctcctt ctctaacagt gcagacgata | 1320 |

| | |
|---|---|
| tcaagtccaa gaaaaagcgg gagcagtcta atgacattgc tagggcttc gagagaggac | 1380 |
| tggagccaga aaaaatcatt ggggcaaccg acagctgcgg cgatctgatg tttctcatga | 1440 |
| aatggaagga cacagatgag gccgacctgg tgctcgccaa agaagctaac gtgaagtgtc | 1500 |
| cccagatcgt cattgctttt tacgaggaaa ggctcacctg gcacgcatat cctgaggatg | 1560 |
| ccgaaaacaa ggagaaggaa tcagctaaga gctga | 1595 |

<210> SEQ ID NO 64
<211> LENGTH: 6159
<212> TYPE: DNA
<213> ORGANISM: Artificial Sequence
<220> FEATURE:
<223> OTHER INFORMATION: synthetic

<400> SEQUENCE: 64

| | |
|---|---|
| cctgcaggca gctgcgcgct cgctcgctca ctgaggccgc ccgggcgtcg ggcgaccttt | 60 |
| ggtcgcccgg cctcagtgag cgagcgagcg cgcagagagg gagtggccaa ctccatcact | 120 |
| aggggttcct gcggccgcac gcgttgatat caactttgta tagaaaagtt ttcccatgat | 180 |
| tccttcatat ttgcatatac gatacaaggc tgttagagag ataattggaa ttaatttgac | 240 |
| tgtaaacaca agatattag tacaaaatac gtgacgtaga aagtaataat ttcttgggta | 300 |
| gtttgcagtt ttaaaattat gttttaaaat ggactatcat atgcttaccg taacttgaaa | 360 |
| gtatttcgat ttcttggctt tatatatctt gtggaaagga cgaaacacct gcgggtcctg | 420 |
| cactgtttta gagctaggcc aacatgagga tcacccatgt ctgcagggcc tagcaagtta | 480 |
| aaataaggct agtccgttat caacttggcc aacatgagga tcacccatgt ctgcagggcc | 540 |
| aagtggcacc gagtcggtgc ttttttttgaa ttctgatgcg gtattttctc cttacgcatc | 600 |
| tgtgcggtat ttcacaccgc atacgtcaaa gcaaccatag tacgcgccct gtatttccca | 660 |
| tgattccttc atatttgcat atacgataca aggctgttag agataatt ggaattaatt | 720 |
| tgactgtaaa cacaaagata ttagtacaaa atacgtgacg tagaaagtaa taatttcttg | 780 |
| ggtagtttgc agttttaaaa ttatgtttta aaatggacta tcatatgctt accgtaactt | 840 |
| gaaagtattt cgatttcttg gctttatata tcttgtggaa aggacgaaac accgaagctt | 900 |
| cgggagggtt ttagagctag gccaacatga ggatcaccca tgtctgcagg gcctagcaag | 960 |
| ttaaaataag gctagtccgt tatcaacttg gccaacatga ggatcaccca tgtctgcagg | 1020 |
| gccaagtggc accgagtcgg tgcttttttt gaattctgat gcggtatttt ctccttacgc | 1080 |
| atctgtgcgg tatttcacac cgcatacgtc aaagcaacca tagtacgcgc cctgtagcgg | 1140 |
| acccaagttt gtacaaaaaa gcaggctagg ctccggtgcc cgtcagtggg cagagcgcac | 1200 |
| atcgcccaca gtccccgaga gttgggggg aggggtcggc aattgaaccg gtgcctagag | 1260 |
| aaggtggcgc ggggtaaact gggaaagtga tgtcgtgtac tggctccgcc ttttttccga | 1320 |
| gggtggggga gaaccgtata taagtgcagt agtcgccgtg aacgttcttt ttcgcaacgg | 1380 |
| gtttgccgcc agaacacagc ttaagcttgg taccgagctc ggatccacta gtaacggccg | 1440 |
| ccagtgtgct ggaattctgc agatatccat cacactggcg gccgctcgag catgcatcta | 1500 |
| gaggacaact ttgtatacaa aagttgaggc tggatcccgg tacctcgac acctgctgac | 1560 |
| aggtccacca tgggacctaa gaaaaagagg aaggtggcgg ccgctgacta caaggatgac | 1620 |
| gacgataaat ctagaatggc ttctaacttt actcagttcg ttctcgtcga caatggcgga | 1680 |
| actggcgacg tgactgtcgc cccaagcaac ttcgctaacg gatcgctga atggatcagc | 1740 |

```
tctaactcgc gttcacaggc ttacaaagta acctgtagcg ttcgtcagag ctctgcgcag   1800
aatcgcaaat acaccatcaa agtcgaggtg cctaaaggcg cctggcgttc gtacttaaat   1860
atggaactaa ccattccaat tttcgccacg aattccgact gcgagcttat tgttaaggca   1920
atgcaaagtc tcctaaaaga tggaaacccg attccctcag caatcgcagc aaactccggc   1980
atctacgagg ccagccccaa gaagaagagg aaggtgagtg gtggaggaag tggcgggtca   2040
gggtcgagcc ccaagaaaaa acggaaagtg gaggcatcaa tgaaggaggg agaaaacaac   2100
aaacccaggg agaaaagtga agggaataag agaaaaagct ccttctctaa cagtgcagac   2160
gatatcaagt ccaagaaaaa gcgggagcag tctaatgaca ttgctagggg cttcgagaga   2220
ggactggagc cagaaaaaat cattggggca accgacagct gcggcgatct gatgtttctc   2280
atgaaatgga aggacacaga tgaggccgac ctggtgctcg ccaaagaagc taacgtgaag   2340
tgtccccaga tcgtcattgc ttttacgag gaaaggctca cctggcacgc atatcctgag   2400
gatgccgaaa acaaggagaa ggaatcagct aagagctcgg gaggtggttc gggtggctct   2460
ggatcaatgg acgcgaaatc acttacgca tggtcgagaa cactggttac gttcaaggac   2520
gtgtttgtgg actttacacg tgaggagtgg aaattgctgg atactgcgca acaaattgtg   2580
tatcgaaatg tcatgcttga gaattacaag aacctcgtca gtctcggata ccagttgacg   2640
aaaccggatg tgatccttag gctcgaaaag ggggaagaac cttggctggt atagaagaat   2700
tcgatcccgc ttcagtgcag gtgaattcta ccacccagct taagcttggt accgagctcg   2760
gatccactag taacggccgc cagtgtgctg gaattctgca gatatccatc acactggcgg   2820
ccgctcgagc atgcatctag aggtacccag cttcttgta caaagtggta agcttgcctc   2880
gagcagcgct gctcgagaga tctacggtg gcatccctgt gaccctcc cagtgcctct   2940 cctggccctg gaagttgcca ctccagtgcc caccagcctt gtcctaataa aattaagttg   3000
catcattttg tctgactagg tgtccttcta taatattatg gggtggaggg gggtggtatg   3060
gagcaagggg caagttggga agacaacctg tagggcctgc ggggtctatt gggaaccaag   3120
ctggagtgca gtggcacaat cttggctcac tgcaatctcc gcctcctggg ttcaagcgat   3180
tctcctgcct cagcctcccg agttgttggg attccaggca tgcatgacca ggctcagcta   3240
atttttgttt ttttggtaga acggggtttt caccatattg gccaggctgg tctccaactc   3300
ctaatctcag gtgatctacc caccttggcc tcccaaattg ctgggattac aggcgtgaac   3360
cactgctccc ttccctgtcc ttctgatttt gtaggtaacc acgtgcggac cgagcggccg   3420 caggaaccc tagtgatgga gttggccact ccctctctgc gcgctcgctc gctcactgag   3480
gccgggcgac caaaggtcgc ccgacgcccg ggctttgccc gggcggcctc agtgagcgag   3540
cgagcgcgca gctgcctgca ggggcgcctg atgcggtatt ttctccttac gcatctgtgc   3600
ggtatttcac accgcatacg tcaaagcaac catagtacgc gccctgtagc ggcgcattaa   3660
gcgcggcggt gtggtggtt acgcgcagcg tgaccgctac acttgccagc gccctagcgc   3720
ccgctccttt cgctttcttc ccttcctttc tcgccacgtt cgccggcttt ccccgtcaag   3780
ctctaaatcg ggggctccct ttagggttcc gatttagtgc tttacggcac ctcgacccca   3840
aaaaacttga tttgggtgat ggttcacgta gtgggccatc gccctgatag acggtttttc   3900
gccctttgac gttggagtcc acgttcttta atagtggact cttgttccaa actggaacaa   3960
cactcaaccc tatctcgggc tattctttg atttataagg gattttgccg atttcggcct   4020
attggttaaa aaatgagctg atttaacaaa aatttaacgc gaattttaac aaaatattaa   4080
cgtttacaat tttatggtgc actctcagta caatctgctc tgatgccgca tagttaagcc   4140
```

```
agccccgaca cccgccaaca cccgctgacg cgccctgacg ggcttgtctg ctcccggcat    4200
ccgcttacag acaagctgtg accgtctccg ggagctgcat gtgtcagagg ttttcaccgt    4260
catcaccgaa acgcgcgaga cgaaagggcc tcgtgatacg cctattttta taggttaatg    4320
tcatgataat aatggtttct tagacgtcag gtggcacttt tcggggaaat gtgcgcggaa    4380
cccctatttg tttatttttc taaatacatt caaatatgta tccgctcatg agacaataac    4440
cctgataaat gcttcaataa tattgaaaaa ggaagagtat gagtattcaa catttccgtg    4500
tcgcccttat tcccttttt gcggcatttt gccttcctgt ttttgctcac ccagaaacgc     4560
tggtgaaagt aaaagatgct gaagatcagt tgggtgcacg agtgggttac atcgaactgg    4620
atctcaacag cggtaagatc cttgagagtt ttcgccccga agaacgtttt ccaatgatga    4680
gcacttttaa agttctgcta tgtggcgcgg tattatcccg tattgacgcc gggcaagagc    4740
aactcggtcg ccgcatacac tattctcaga atgacttggt tgagtactca ccagtcacag    4800
aaaagcatct tacggatggc atgacagtaa gagaattatg cagtgctgcc ataaccatga    4860
gtgataacac tgcggccaac ttacttctga acgatcgg aggaccgaag gagctaaccg      4920
cttttttgca caacatgggg gatcatgtaa ctcgccttga tcgttgggaa ccggagctga    4980
atgaagccat accaaacgac gagcgtgaca ccacgatgcc tgtagcaatg gcaacaacgt    5040
tgcgcaaact attaactggc gaactactta ctctagcttc ccggcaacaa ttaatagact    5100
ggatggaggc ggataaagtt gcaggaccac ttctgcgctc ggcccttccg gctggctggt    5160
ttattgctga taaatctgga gccggtgagc gtgggtctcg cggtatcatt gcagcactgg    5220
ggccagatgg taagccctcc cgtatcgtag ttatctacac gacggggagt caggcaacta    5280
tggatgaacg aaatagacag atcgctgaga taggtgcctc actgattaag cattggtaac    5340
tgtcagacca agtttactca tatatacttt agattgattt aaaacttcat ttttaattta    5400
aaaggatcta ggtgaagatc ctttttgata atctcatgac caaaatccct taacgtgagt    5460
tttcgttcca ctgagcgtca gaccccgtag aaaagatcaa aggatcttct tgagatcctt    5520
tttttctgcg cgtaatctgc tgcttgcaaa caaaaaaacc accgctacca gcggtggttt    5580
gtttgccgga tcaagagcta ccaactcttt ttccgaaggt aactggcttc agcagagcgc    5640
agataccaaa tactgtcctt ctagtgtagc cgtagttagg ccaccacttc aagaactctg    5700
tagcaccgcc tacatacctc gctctgctaa tcctgttacc agtggctgct gccagtggcg    5760
ataagtcgtg tcttaccggg ttggactcaa gacgatagtt accggataag gcgcagcggt    5820
cgggctgaac ggggggttcg tgcacacagc ccagcttgga gcgaacgacc tacaccgaac    5880
tgagatacct acagcgtgag ctatgagaaa gcgccacgct tcccgaaggg agaaaggcgg    5940
acaggtatcc ggtaagcggc agggtcgaa caggagagcg cacgagggag cttccagggg    6000
gaaacgcctg gtatctttat agtcctgtcg gtttcgcca cctctgactt gagcgtcgat     6060
ttttgtgatg ctcgtcaggg gggcggagcc tatgaaaaa cgccagcaac gcggcctttt     6120
tacggttcct ggccttttgc tggccttttg ctcacatgt                           6159
```

<210> SEQ ID NO 65
<211> LENGTH: 6158
<212> TYPE: DNA
<213> ORGANISM: Artificial Sequence
<220> FEATURE:
<223> OTHER INFORMATION: synthetic

<400> SEQUENCE: 65

```
cctgcaggca gctgcgcgct cgctcgctca ctgaggccgc ccgggcgtcg ggcgaccttt    60
ggtcgcccgg cctcagtgag cgagcgagcg cgcagagagg gagtggccaa ctccatcact   120
aggggttcct gcggccgcac gcgttgatat caactttgta tagaaaagtt ttcccatgat   180
tccttcatat ttgcatatac gatacaaggc tgttagagag ataattgaaa ttaatttgac   240
tgtaaacaca aagatattag tacaaaatac gtgacgtaga aagtaataat ttcttgggta   300
gtttgcagtt ttaaaattat gttttaaaat ggactatcat atgcttaccg taacttgaaa   360
gtatttcgat ttcttggctt tatatatctt gtggaaagga cgaaacacca taaaagtccg   420
gttgttttag agctaggcca acatgaggat cacccatgtc tgcagggcct agcaagttaa   480
aataaggcta gtccgttatc aacttggcca acatgaggat cacccatgtc tgcagggcca   540
agtggcaccg agtcggtgct ttttttgaat tctgatgcgg tattttctcc ttacgcatct   600
gtgcggtatt tcacaccgca tacgtcaaag caaccatagt acgcgcctg tatttcccat    660 gattccttca tatttgcata tacgatacaa ggctgttaga gagataattg gaattaattt   720
gactgtaaac acaagatat  tagtacaaaa tacgtgacgt agaaagtaat aatttcttgg   780
gtagtttgca gttttaaaat tatgttttaa aatggactat catatgctta ccgtaacttg   840
aaagtatttc gatttcttgg ctttatatat cttgtggaaa ggacgaaaca cctccggtaa   900
ccaccagttt tagagctagg ccaacatgag gatcacccat gtctgcaggg cctagcaagt   960
taaaataagg ctagtccgtt atcaacttgg ccaacatgag gatcacccat gtctgcaggg  1020
ccaagtggca ccgagtcggt gcttttttg aattctgatg cggtattttc tccttacgca   1080
tctgtgcggt atttcacacc gcatacgtca agcaaccat agtacgcgcc ctgtagcgga   1140
cccaagtttg tacaaaaaag caggctaggc tccggtgccc gtcagtgggc agagcgcaca  1200
tcgcccacag tccccgagaa gttgggggga gggtcggca attgaaccgg tgcctagaga   1260
aggtggcgcg gggtaaactg gaaagtgat gtcgtgtact ggctccgcct ttttcccgag    1320
ggtgggggag aaccgtatat aagtgcagta gtcgccgtga acgttctttt tcgcaacggg   1380
tttgccgcca gaacacagct taagcttggt accgagctcg gatccactag taacggccgc   1440
cagtgtgctg gaattctgca gatatccatc acactggcgg ccgctcgagc atgcatctag  1500
aggacaactt tgtatacaaa agttgaggct ggatcccggt accctcgaca cctgctgaca  1560
ggtccaccat gggacctaag aaaaagagga aggtggcggc cgctgactac aaggatgacg   1620
acgataaatc tagaatggct tctaaacttta ctcagttcgt tctcgtcgac aatggcggaa  1680
ctggcgacgt gactgtcgcc caagcaact tcgctaacgg gatcgctgaa tggatcagct    1740
ctaactcgcg ttcacaggct tacaaagtaa cctgtagcgt tcgtcagagc tctgcgcaga  1800
atcgcaaata caccatcaaa gtcgaggtgc ctaaaggcgc ctggcgttcg tacttaaata  1860
tggaactaac cattccaatt ttcgccacga attccgactg cgagcttatt gttaaggcaa   1920
tgcaaagtct cctaaaagat ggaaacccga ttccctcagc aatcgcagca actccggca    1980 tctacgaggc cagccccaag aagaagagga aggtgagtgg tggaggaagt ggcgggtcag  2040
ggtcgagccc caagaaaaaa cggaaagtgg aggcatcaat gaaggaggga gaaaacaaca  2100
aacccaggga gaaagtgaa gggaataaga gaaaagctc cttctctaac agtgcagacg    2160
atatcaagtc caagaaaaag cgggagcagt ctaatgacat tgctagggc ttcgagagag    2220 gactggagcc agaaaaaatc attgggggcaa ccgacagctg cggcgatctg atgtttctca  2280
tgaaatggaa ggacacagat gaggccgacc tggtgctcgc caaagaagct aacgtgaagt  2340
gtccccagat cgtcattgct ttttacgagg aaaggctcac ctggcacgca tatcctgagg  2400
```

```
atgccgaaaa caaggagaag gaatcagcta agagctcggg aggtggttcg ggtggctctg    2460
gatcaatgga cgcgaaatca cttacggcat ggtcgagaac actggttacg ttcaaggacg    2520
tgtttgtgga ctttacacgt gaggagtgga aattgctgga tactgcgcaa caaattgtgt    2580
atcgaaatgt catgcttgag aattacaaga acctcgtcag tctcggatac cagttgacga    2640
aaccggatgt gatccttagg ctcgaaaagg gggaagaacc ttggctggta tagaagaatt    2700
cgatcccgct tcagtgcagg tgaattctac cacccagctt aagcttggta ccgagctcgg    2760
atccactagt aacggccgcc agtgtgctgg aattctgcag atatccatca cactggcggc    2820
cgctcgagca tgcatctaga ggtacccagc tttcttgtac aaagtggtaa gcttgcctcg    2880
agcagcgctg ctcgagagat ctacgggtgg catccctgtg acccctcccc agtgcctctc    2940
ctggccctgg aagttgccac tccagtgccc accagccttg tcctaataaa attaagttgc    3000
atcattttgt ctgactaggt gtccttctat aatattatgg ggtggagggg ggtggtatgg    3060
agcaaggggc aagttgggaa gacaacctgt agggcctgcg gggtctattg ggaaccaagc    3120
tggagtgcag tggcacaatc ttggctcact gcaatctccg cctcctgggt tcaagcgatt    3180
ctcctgcctc agcctcccga gttgttggga ttccaggcat gcatgaccag gctcagctaa    3240
tttttgtttt tttggtagag acggggtttc accatattgg ccaggctggt ctccaactcc    3300
taatctcagg tgatctaccc accttggcct cccaaattgc tgggattaca ggcgtgaacc    3360
actgctccct tccctgtcct tctgattttg taggtaacca cgtgcggacc gagcggccgc    3420
aggaacccct agtgatggag ttggccactc cctctctgcg cgctcgctcg ctcactgagg    3480
ccgggcgacc aaaggtcgcc cgacgcccgg gctttgcccg ggcggcctca gtgagcgagc    3540
gagcgcgcag ctgcctgcag gggcgcctga tgcggtattt tctccttacg catctgtgcg    3600
gtatttcaca ccgcatacgt caaagcaacc atagtacgcg ccctgtagcg cgcattaag    3660 cgcggcgggt gtggtggtta cgcgcagcgt gaccgctaca cttgccagcg ccctagcgcc    3720
cgctcctttc gctttcttcc cttcctttct cgccacgttc gccggctttc cccgtcaagc    3780
tctaaatcgg gggctccctt tagggttccg atttagtgct ttacggcacc tcgaccccaa    3840
aaaacttgat ttgggtgatg gttcacgtag tgggccatcg ccctgataga cggtttttcg    3900
ccctttgacg ttggagtcca cgttctttaa tagtggactc ttgttccaaa ctggaacaac    3960
actcaaccct atctcgggct attcttttga tttataaggg attttgccga tttcggccta    4020
ttggttaaaa aatgagctga tttaacaaaa atttaacgcg aattttaaca aaatattaac    4080
gtttacaatt ttatggtgca ctctcagtac aatctgctct gatgccgcat agttaagcca    4140
gccccgacac ccgccaacac ccgctgacgc gccctgacgg gcttgtctgc tcccggcatc    4200
cgcttacaga caagctgtga ccgtctccgg gagctgcatg tgtcagaggt tttcaccgtc    4260
atcaccgaaa cgcgcgagac gaaagggcct cgtgatacgc ctatttttat aggttaatgt    4320
catgataata atggtttctt agacgtcagg tggcactttt cggggaaatg tgcgcggaac    4380
ccctatttgt ttatttttct aaatacattc aaatatgtat ccgctcatga caataaccc    4440 ctgataaatg cttcaataat attgaaaaag gaagagtatg agtattcaac atttccgtgt    4500
cgcccttatt ccctttttg cggcattttg ccttcctgtt tttgctcacc cagaaacgct    4560
ggtgaaagta aaagatgctg aagatcagtt gggtgcacga gtgggttaca tcgaactgga    4620
tctcaacagc ggtaagatcc ttgagagttt tcgccccgaa gaacgttttc caatgatgag    4680
cacttttaaa gttctgctat gtggcgcggt attatcccgt attgacgccg ggcaagagca    4740
```

```
actcggtcgc cgcatacact attctcagaa tgacttggtt gagtactcac cagtcacaga    4800
aaagcatctt acggatggca tgacagtaag agaattatgc agtgctgcca taaccatgag    4860
tgataacact gcggccaact tacttctgac aacgatcgga ggaccgaagg agctaaccgc    4920
tttttttgcac aacatggggg atcatgtaac tcgccttgat cgttgggaac cggagctgaa    4980
tgaagccata ccaaacgacg agcgtgacac cacgatgcct gtagcaatgg caacaacgtt    5040
gcgcaaacta ttaactggcg aactacttac tctagcttcc cggcaacaat taatagactg    5100
gatggaggcg gataaagttg caggaccact tctgcgctcg gcccttccgg ctggctggtt    5160
tattgctgat aaatctggag ccggtgagcg tgggtctcgc ggtatcattg cagcactggg    5220
gccagatggt aagccctccc gtatcgtagt tatctacacg acggggagtc aggcaactat    5280
ggatgaacga aatagacaga tcgctgagat aggtgcctca ctgattaagc attggtaact    5340
gtcagaccaa gtttactcat atatacttta gattgattta aaacttcatt tttaatttaa    5400
aaggatctag gtgaagatcc ttttttgataa tctcatgacc aaaatccctt aacgtgagtt    5460
ttcgttccac tgagcgtcag accccgtaga aaagatcaaa ggatcttctt gagatccttt    5520
ttttctgcgc gtaatctgct gcttgcaaac aaaaaaacca ccgctaccag cggtggtttg    5580
tttgccggat caagagctac caactctttt tccgaaggta actggcttca gcagagcgca    5640
gataccaaat actgtccttc tagtgtagcc gtagttaggc caccacttca gaactctgt     5700
agcaccgcct acatacctcg ctctgctaat cctgttacca gtggctgctg ccagtggcga    5760
taagtcgtgt cttaccgggt tggactcaag acgatagtta ccggataagg cgcagcggtc    5820
gggctgaacg gggggttcgt gcacacagcc cagcttggag cgaacgacct acaccgaact    5880
gagataccta cagcgtgagc tatgagaaag cgccacgctt cccgaaggga gaaaggcgga    5940
caggtatccg gtaagcggca gggtcggaac aggagagcgc acgagggagc ttccaggggg    6000
aaacgcctgg tatctttata gtcctgtcgg gtttcgccac ctctgacttg agcgtcgatt    6060
tttgtgatgc tcgtcagggg ggcggagcct atggaaaaac gccagcaacg cggccttttt    6120
acggttcctg gccttttgct ggccttttgc tcacatgt                            6158
```

<210> SEQ ID NO 66
<211> LENGTH: 7499
<212> TYPE: DNA
<213> ORGANISM: Artificial Sequence
<220> FEATURE:
<223> OTHER INFORMATION: synthetic

<400> SEQUENCE: 66

```
cctgcaggca gctgcgcgct cgctcgctca ctgaggccgc ccgggcaaag cccgggcgtc      60
gggcgacctt tggtcgcccg gcctcagtga gcgagcgagc gcgcagagag ggagtggcca    120
actccatcac taggggttcc tgcggcctct agaaatgtag tcttatgcaa tactcttgta    180
gtcttgcaac atggtaacga tgagttagca acatgcctta caaggagaga aaaagcaccg    240
tgcatgccga ttggtggaag taaggtggta cgatcgtgcc ttattaggaa ggcaacagac    300
gggtctgaca tggattggac gaaccactga attgccgcat tgcagagata ttgtatttaa    360
gtgcctagct cgatacataa aaccggtgcc accatgtacc catacgatgt tccagattac    420
gcttcgccga agaaaagcg caaggtcgaa gcgtccgaca agaagtacag catcggcctg    480
gacatcggca ccaactctgt gggctgggcc gtgatcaccg acgagtacaa ggtgcccagc    540
aagaaattca aggtgctggg caacaccgac cggcacagca tcaagaagaa cctgatcgga    600
gccctgctgt tcgacagcgg cgaaacagcc gaggccaccc ggctgaagag aaccgccaga    660
```

```
agaagataca ccagacggaa gaaccggatc tgctatctgc aagagatctt cagcaacgag      720
atggccaagg tggacgacag cttcttccac agactggaag agtccttcct ggtggaagag      780
gataagaagc acgagcggca ccccatcttc ggcaacatcg tggacgaggt ggcctaccac      840
gagaagtacc ccaccatcta ccacctgaga aagaaactgg tggacagcac cgacaaggcc      900
gacctgcggc tgatctatct ggccctggcc cacatgatca agttccgggg ccacttcctg      960
atcgagggcg acctgaaccc cgacaacagc gacgtggaca gctgttcat ccagctggtg      1020 cagacctaca accagctgtt cgaggaaaac cccatcaacg ccagcggcgt ggacgccaag      1080
gccatcctgt ctgccagact gagcaagagc agacggctgg aaaatctgat cgcccagctg      1140
cccggcgaga agaagaatgg cctgttcggc aacctgattg ccctgagcct gggcctgacc      1200
cccaacttca gagcaacttt cgacctggcc gaggatgcca actgcagct gagcaaggac      1260 acctacgacg acgacctgga caacctgctg gcccagatcg gcgaccagta cgccgacctg      1320
tttctggccg ccaagaacct gtccgacgcc atcctgctga cgacatcct gagagtgaac      1380 accgagatca ccaaggcccc cctgagcgcc tctatgatca agagatacga cgagcaccac      1440
caggacctga ccctgctgaa agctctcgtg cggcagcagc tgcctgagaa gtacaaagag      1500
attttcttcg accagagcaa gaacggctac gccggctaca ttgacggcgg agccagccag      1560
gaagagttct acaagttcat caagcccatc ctggaaaaga tggacggcac cgaggaactg      1620
ctcgtgaagc tgaacagaga ggacctgctg cggaagcagc ggaccttcga caacggcagc      1680
atcccccacc agatccacct gggagagctg cacgccattc tgcggcggca ggaagatttt      1740
tacccattcc tgaaggacaa ccgggaaaag atcgagaaga tcctgacctt ccgcatcccc      1800
tactacgtgg gccctctggc caggggaaac agcagattcg cctggatgac cagaaagagc      1860
gaggaaacca tcacccctg aacttcgag gaagtggtgg acaagggcgc ttccgcccag      1920
agcttcatcg agcggatgac caacttcgat aagaacctgc ccaacgagaa ggtgctgccc      1980
aagcacagcc tgctgtacga gtacttcacc gtgtataacg agctgaccaa agtgaaatac      2040
gtgaccgagg gaatgagaaa gcccgccttc ctgagcggcg agcagaaaaa ggccatcgtg      2100
gacctgctgt tcaagaccaa ccggaaagtg accgtgaagc agctgaaaga ggactacttc      2160
aagaaaatcg agtgcttcga ctccgtggaa atctccggcg tggaagatcg gttcaacgcc      2220
tccctgggca cataccacga tctgctgaaa attatcaagg acaaggactt cctggacaat      2280
gaggaaaacg aggacattct ggaagatatc gtgctgaccc tgacactgtt tgaggacaga      2340
gagatgatcg aggaacggct gaaaacctat gcccacctgt tcgacgacaa agtgatgaag      2400
cagctgaagc ggcggagata caccggctgg ggcaggctga gccggaagct gatcaacggc      2460
atccgggaca gcagtccgg caagacaatc ctggatttcc tgaagtccga cggcttcgcc      2520
aacagaaact tcatgcagct gatccacgac gacagcctga cctttaaaga ggacatccag      2580
aaagcccagg tgtccggcca gggcgatagc ctgcacgagc acattgccaa tctggccggc      2640
agccccgcca ttaagaaggg catcctgcag acagtgaagg tggtggacga gctcgtgaaa      2700
gtgatgggcc ggcacaagcc cgagaacatc gtgatcgaaa tggccagaga gaaccagacc      2760
acccagaagg gacagaagaa cagccgcgag agaatgaagc ggatcgaaga gggcatcaaa      2820
gagctgggca gccagatcct gaaagaacac cccgtggaaa acacccagct gcagaacgag      2880
aagctgtacc tgtactacct gcagaatggg cgggatatgt acgtggacca ggaactggac      2940
atcaaccggc tgtccgacta cgatgtggac catatcgtgc ctcagagctt tctgaaggac      3000
```

```
gactccatcg acaacaaggt gctgaccaga agcgacaaga accggggcaa gagcgacaac    3060
gtgccctccg aagaggtcgt gaagaagatg aagaactact ggcggcagct gctgaacgcc    3120
aagctgatta cccagagaaa gttcgacaat ctgaccaagg ccgagagagg cggcctgagc    3180
gaactggata aggccggctt catcaagaga cagctggtgg aaacccggca gatcacaaag    3240
cacgtggcac agatcctgga ctcccggatg aacactaagt acgacgagaa tgacaagctg    3300
atccgggaag tgaaagtgat caccctgaag tccaagctgg tgtccgattt ccggaaggat    3360
ttccagtttt acaaagtgcg cgagatcaac aactaccacc acgcccacga cgcctacctg    3420
aacgccgtcg tgggaaccgc cctgatcaaa agtaccccta agctggaaag cgagttcgtg    3480
tacgcgact acaaggtgta cgacgtgcgg aagatgatcg ccaagagcga gcaggaaatc    3540
ggcaaggcta ccgccaagta cttcttctac agcaacatca tgaactttt caagaccgag    3600
attaccctgg ccaacggcga gatccggaag cggcctctga tcgagacaaa cggcgaaacc    3660
ggggagatcg tgtgggataa gggccgggat tttgccaccg tgcggaaagt gctgagcatg    3720
ccccaagtga atatcgtgaa aaagaccgag gtgcagacag gcggcttcag caaagagtct    3780
atcctgccca gaggaacag cgataagctg atcgccagaa agaaggactg gacccctaag    3840
aagtacggcg gcttcgacag ccccaccgtg gcctattctg tgctggtggt ggccaaagtg    3900
gaaaagggca gtccaagaa actgaagagt gtgaaagagc tgctggggat caccatcatg    3960
gaaagaagca gcttcgagaa gaatcccatc gactttctgg aagccaaggg ctacaaagaa    4020
gtgaaaaagg acctgatcat caagctgcct aagtactccc tgttcgagct ggaaaacggc    4080
cggaagagaa tgctggcctc tgccggcgaa ctgcagaagg aaacgaact ggccctgccc    4140
tccaaatatg tgaacttcct gtacctggcc agccactatg agaagctgaa gggctccccc    4200
gaggataatg agcagaaaca gctgtttgtg aacagcaca agcactacct ggacgagatc    4260
atcgagcaga tcagcgagtt ctccaagaga gtgatcctgg ccgacgctaa tctggacaaa    4320
gtgctgtccg cctacaacaa gcaccgggat aagcccatca gagagcaggc cgagaatatc    4380
atccacctgt ttaccctgac caatctggga gcccctgccg ccttcaagta ctttgacacc    4440
accatcgacc ggaagaggta caccagcacc aaagaggtgc tggacgccac cctgatccac    4500
cagagcatca ccggcctgta cgagacacgg atcgacctgt ctcagctggg aggcgacagc    4560
cccaagaaga agaaaggt ggaggccagc taagaattca gcggcgcgcc ttcccaaaac    4620
ccaccaaact aagtaactgc tacttctctc agcaacacca agatcaatga agaggcaag    4680
gtgggtcttc gagaagacct gcttaataaa agatctttat tttcattaga tctgtgtgtt    4740
ggttttttgt gtggcggccg caggaacccc tagtgatgga gttggccact ccctctctgc    4800
gcgctcgctc gctcactgag gccgggcgac caaaggtcgc ccgacgcccg gctttgccc    4860
gggcggcctc agtgagcgag cgagcgcgca gctgcctgca ggggcgcctg atgcggtatt    4920
ttctccttac gcatctgtgc ggtatttcac accgcatacg tcaaagcaac catagtacgc    4980
gccctgtagc ggcgcattaa gcgcggcggg tgtggtggtt acgcgcagcg tgaccgctac    5040
acttgccagc gccctagcgc ccgctccttt cgctttcttc ccttcctttc tcgccacgtt    5100
cgccggcttt ccccgtcaag ctctaaatcg ggggctccct ttagggttcc gatttagtgc    5160
tttacggcac ctcgacccca aaaaacttga tttgggtgat ggttcacgta gtgggccatc    5220
gccctgatag acggtttttc gccctttgac gttggagtcc acgttcttta atagtggact    5280
cttgttccaa actggaacaa cactcaaccc tatctcgggc tattcttttg atttataagg    5340
gattttgccg atttcggcct attggttaaa aaatgagctg atttaacaaa aatttaacgc    5400
```

-continued

```
gaattttaac aaaatattaa cgtttacaat tttatggtgc actctcagta caatctgctc    5460
tgatgccgca tagttaagcc agccccgaca cccgccaaca cccgctgacg cgccctgacg    5520
ggcttgtctg ctcccggcat ccgcttacag acaagctgtg accgtctccg ggagctgcat    5580
gtgtcagagg ttttcaccgt catcaccgaa acgcgcgaga cgaaagggcc tcgtgatacg    5640
cctatttta taggttaatg tcatgataat aatggtttct tagacgtcag gtggcacttt    5700
tcggggaaat gtgcgcggaa cccctatttg tttatttttc taaatacatt caaatatgta    5760
tccgctcatg agacaataac cctgataaat gcttcaataa tattgaaaaa ggaagagtat    5820
gagtattcaa catttccgtg tcgcccttat tcccttttt gcggcatttt gccttcctgt    5880
ttttgctcac ccagaaacgc tggtgaaagt aaaagatgct gaagatcagt tgggtgcacg    5940
agtgggttac atcgaactgg atctcaacag cggtaagatc cttgagagtt ttcgccccga    6000
agaacgtttt ccaatgatga gcacttttaa agttctgcta tgtggcgcgg tattatcccg    6060
tattgacgcc gggcaagagc aactcggtcg ccgcatacac tattctcaga atgacttggt    6120
tgagtactca ccagtcacag aaaagcatct tacggatggc atgacagtaa gagaattatg    6180
cagtgctgcc ataaccatga gtgataacac tgcggccaac ttacttctga caacgatcgg    6240
aggaccgaag gagctaaccg cttttttgca caacatgggg gatcatgtaa ctcgccttga    6300
tcgttgggaa ccggagctga atgaagccat accaaacgac gagcgtgaca ccacgatgcc    6360
tgtagcaatg gcaacaacgt tgcgcaaact attaactggc gaactactta ctctagcttc    6420
ccggcaacaa ttaatagact ggatggaggc ggataaagtt gcaggaccac ttctgcgctc    6480
ggcccttccg gctggctggt ttattgctga taaatctgga gccggtgagc gtggaagccg    6540
cggtatcatt gcagcactgg ggccagatgg taagccctcc cgtatcgtag ttatctacac    6600
gacggggagt caggcaacta tggatgaacg aaatagacag atcgctgaga taggtgcctc    6660
actgattaag cattggtaac tgtcagacca agtttactca tatatacttt agattgattt    6720
aaaacttcat ttttaattta aaaggatcta ggtgaagatc ctttttgata atctcatgac    6780
caaaatccct taacgtgagt tttcgttcca ctgagcgtca gaccccgtag aaaagatcaa    6840
aggatcttct tgagatcctt ttttttctgcg cgtaatctgc tgcttgcaaa caaaaaaacc    6900
accgctacca gcggtggttt gtttgccgga tcaagagcta ccaactcttt ttccgaaggt    6960
aactggcttc agcagagcgc agataccaaa tactgtcctt ctagtgtagc cgtagttagg    7020
ccaccacttc aagaactctg tagcaccgcc tacatacctc gctctgctaa tcctgttacc    7080
agtggctgct gccagtggcg ataagtcgtg tcttaccggg ttggactcaa gacgatagtt    7140
accggataag gcgcagcggt cgggctgaac ggggggttcg tgcacacagc ccagcttgga    7200
gcgaacgacc tacaccgaac tgagatacct acagcgtgag ctatgagaaa gcgccacgct    7260
tcccgaaggg agaaaggcgg acaggtatcc ggtaagcggc agggtcggaa caggagagcg    7320
cacgagggag cttccagggg gaaacgcctg gtatctttat agtcctgtcg gtttcgcca    7380
cctctgactt gagcgtcgat ttttgtgatg ctcgtcaggg gggcggagcc tatggaaaaa    7440
cgccagcaac gcggcctttt tacggttcct ggccttttgc tggccttttg ctcacatgt    7499
```

SYNTHETIC IMMUNOMODULATION WITH A CRISPR SUPER-REPRESSOR IN VIVO

CROSS-REFERENCE TO RELATED APPLICATIONS

This application is a national stage filing under 35 U.S.C. § 371 of International Application No. PCT/US2019/060285, filed Nov. 7, 2019, which claims priority to U.S. Provisional Application No. 62/757,679, filed Nov. 8, 2018, and U.S. Provisional Application No. 62/899,584, filed Sep. 12, 2019, each of which is incorporated herein in its entirety.

STATEMENT REGARDING FEDERALLY SPONSORED RESEARCH

This invention was made with government support under R01 EB024562 awarded by the National Institutes of Health and HR0011-16-23657 awarded by DARPA. The government has certain rights in the invention.

REFERENCE TO A SEQUENCE LISTING SUBMITTED VIA EFS-WEB

The content of the ASCII text file of the sequence listing named "112624_01135_ST25.txt" which is 48.4 kb in size was created on Nov. 7, 2019 and electronically submitted via EFS-Web herewith the application is incorporated herein by reference in its entirety.

BACKGROUND

Compared to the common gene delivery methods, adeno-associated viral (AAV) vectors possess a broad potential for therapeutic gene delivery due to their remarkable capacity to target a variety of tissue types at high efficiency. AAV vectors are currently the prevalent type of DNA viruses used in clinic. Long-term and stable expression of the transgene achieved with AAV is necessary for the treatment of chronic diseases. However, it has been shown that AAV vectors or the delivered transgenes evoke an adaptive immune response, which leads to the production of antibodies and cytotoxic T cell response against cells expressing viral capsids or the transgenes. Subsequently, this adaptive host immune response compromises the effective expression of the transgene and have posed a major challenge in AAV-mediated gene therapy in vivo.

In parallel, the Clustered, Regulatory Interspaced, Short Palindromic Repeats (CRISPR)-Cas9 system is providing unprecedented opportunities for gene therapies through facilitating gene editing and gene modulation. Although extremely promising, Cas9 protein from *Streptococcus Pyogenes* (Sp-Cas9), the most common form of CRISPR studied so far, faces a number of challenges for clinical translation including potential immune response and genomic specificity. Recent studies on human samples hint to pre-existing humoral and cellular immune response against Sp-Cas9 in a subset of patients tested, raising the notion that Cas9 protein can also elicit cellular and humoral immune response in new patients. Moreover, it has been demonstrated that temporal limitation of Cas9 expression inside the cells is beneficial towards reducing the off-target activity of CRISPR in the genome. All together, these pieces of evidence suggest that strategies to modulate adverse consequences of CRISPR and its delivery vehicle, including AAV virus, on demand will be of great importance for the safety of clinical translation.

SUMMARY OF THE INVENTION

In a first aspect, provided herein is a synthetic repression system for repressing myeloid differentiation primary response 88 (MyD88) expression in vivo comprising a single amplicon comprising: (a) a guide RNA (gRNA) comprising (i) a guide sequence complementary to a portion of MyD88 and (ii) an aptamer target site specific for an RNA binding protein; (b) a nucleotide sequence encoding the aptamer RNA binding protein fused to one or more repression domain; and (c) a nucleotide sequence encoding a multifunctional Cas nuclease; wherein the single amplicon is packaged in a vector for DNA-based viral delivery. In some embodiments the gRNA guide sequence is 14 nucleotides in length. In some embodiments, the gRNA guide sequence targets within 100 base pairs (bp) upstream of TATA box region of MyD88. In some embodiments, gRNA guide sequence is selected from the group consisting of SEQ ID NOs:1-4. In some embodiments, the aptamer target site is an MS2 aptamer target site and the RNA binding protein is bacteriophage MS2 coat protein. In some embodiments, the gRNA comprises the MS2 aptamer target site and the guide sequence is 14 nucleotides in length.

In some embodiments, the repression domain is selected from the group consisting of a Kruppel associated box (KRAB) domain, methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), and heterochromatin protein 1 (HP1A). In some embodiments, the nucleotide of (b) encodes MS2 fused to at least two repression domains. In some embodiments, the nucleotide sequence encoding MS2 fused to a repression domain comprises a sequence selected from the group consisting of SEQ ID NOs:55, 59, 61, and 63.

In some embodiments, the system comprises a nucleotide sequence encoding a multifunctional Cas nuclease fused to the aptamer RNA binding protein and a repression domain. In some embodiments, the Cas nuclease is an *S. aureus* Cas9 nuclease or an *S. pyogenes* Cas9 nuclease. In some embodiments, the vector is an AAV2/1 delivery vector.

In a second aspect, provided herein is a pharmaceutical composition comprising the synthetic repression system described herein and a pharmaceutically acceptable delivery vehicle.

In a third aspect, provided herein is a method of treating a subject with septicemia comprising administering to the subject with septicemia a therapeutically effective amount of a composition comprising the synthetic repression system described herein. In some embodiments, levels of immune related markers Icam-1, Tnfα, Ncf, Il6, Ifn-α, Ifn-β, Ifn-γ, and Stat4 are reduced in the subject following administration. In some embodiments, the method additionally comprises the step of monitoring the level of at least one immune related marker selected from the group consisting of Icam-1, Tnfα, Ncf, Il6, Ifn-α, Ifn-β, Ifn-γ, and Stat4 and administering to the subject additional doses of the synthetic repression system composition until the level of the at least one immune related marker is reduced. In some embodiments, serum lactate is reduced in the subject following administration.

In a fourth aspect, provided herein is a method of preventing an adverse immune response in a subject comprising administering to the subject a therapeutically effective amount of a composition comprising the synthetic repression system described herein prior to or concurrently with administration of an AAV vector based gene therapy to the subject, wherein the level of an immune related marker selected from the group consisting of Icam-1, Tnfα, Ncf, Il6, Ifn-α, Ifn-β, Ifn-γ, and Stat4 is reduced in the subject relative to subject who received the AAV vector based gene therapy but did not receive the therapeutic synthetic repression system composition. In some embodiments, the subject previously received at least one AAV vector based gene therapy. In some embodiments, the method additionally comprises the step of monitoring the level of at least one immune related marker selected from the group consisting of Icam-1, Tnfα, Ncf, Il6, Ifn-α, Ifn-β, Ifn-γ, and Stat4 and administering to the subject additional doses of the synthetic repression system composition until the level of the at least one immune related marker is reduced.

In a fifth aspect, provided herein is a method of treating Waldenström macroglobulinemia in a subject in need thereof comprising administering to a subject with Waldenström macroglobulinemia a therapeutically effective amount of a composition comprising the synthetic repression system described herein. In some embodiments, the method additionally comprises administering to the subject a composition comprising a gRNA configured to cleave MyD88 at L265 locus and a homology directed repair template encoding a portion of wild-type MyD88 at the L265 locus, whereby levels of endogenous L265P mutant MyD88 are reduced in the subject.

BRIEF DESCRIPTION OF DRAWINGS

(FIG. 1A) Top: Schematic representation of the gRNA binding sites targeted to the promoter of Myd88 locus; Bottom: Mouse Neuroblastoma (N2A) cell lines were transfected with MyD88 gRNA pairs or mock gRNA control together with Cas9 nuclease and either MS2-KRAB or MS2-HP1aKRAB cassettes. 72 hours post-transfection cells were treated with Lipopolysaccharides (*E. coli* LPS, serotype 0111:B4) at a concentration of 10 μg/ml to induce Myd88 expression. (FIG. 1B) qRT-PCR analysis of Myd88 expression mRNA level post LPS treatment. Fold changes were quantified relative to the expression level of cells receiving non-targeting Mockg RNA (N=4 independent transfections). (FIG. 1C) Schematic of experiments involving retro-orbital injection of AAV-MyD88 or Mock repressors to Cas9 nuclease transgenic mice. (FIG. 1D) qRT-PCR analysis of Myd88 expression level in lung, blood, and bone marrow of Cas9 transgenic mice 3 weeks post retro-orbital injections of 1E+12 GC of AAV/Myd88 or AAV/Mock vectors carrying MS2-HP1a-KRAB or MS2-KRAB (N=4-5 for injected groups and N=2 for Not Injected group). Fold changes are relative to universal control (FIGS. 1E and 1F) Fold-change in the expression level of Icam-1 (FIG. 1E), and Tnfα (FIG. 1F) mRNAs relative to the universal control. (N=4-5 for injected groups and N=2 for Not Injected group). Universal control is the level of the desired transcript in the blood sample collected from a not injected mouse, which did not receive any AAV injection. **P<0.01 and *P<0.05 indicate statistical significance measured by Students' t-test. (FIG. 1G) Volcano plot showing significance versus expression of differentially expressed genes between bone marrow samples collected from mice treated with Myd88-Ms2-HP1aKRAB versus Myd88-MS2-KRAB. Points above the dotted line represent genes significantly (adj. p-value <0.05) up and down regulated. Highly downregulated genes in the presence of MS2-HP1aKRAB are a family of immunoglobulin heavy and light chains. (FIG. 1H) Analysis of anti-AAV1 IgG2A antibody measured by ELISA, reveals AAV1 specific antibody is markedly repressed upon Myd88 pre-treatment. **P<0.01 and *P<0.05 indicate statistical significance measured by Students' t-test.

(FIG. 2A) Schematic of the experiments to assess the protective effect of CRISPR mediated MyD88 repression in septicemia. 1E+12 GC of AAV vectors were injected to Cas9 expressing mice via retro-orbital injection and approx. 3 weeks later they were treated i.p. with LPS (5 mg/kg). At 6 hours post LPS injection, the mice were sacrificed. (FIGS. 2B-2D) Endogenous repression of inflammatory genes. qRT-PCR analysis of in vivo Myd88 (FIG. 2B), Tnfα (FIG. 2C), and Icam-1 (FIG. 2D) expression relative to the universal control following LPS injection (N=5-6 for injected groups and N=2 for Not Injected group). (FIG. 2E) Measurement of a panel of inflammatory cytokines in plasma and lung using multiplex-ELISA assay; values are displayed in the heat maps as log base 10 of the measured concentration. (FIG. 2F) Circulating L-lactate in plasma samples collected from mice 6 hours post LPS injection (N=4). (FIG. 2G) qRT-PCR analysis of in vivo Myd88 expression in liver samples 6 hours post LPS injection. Fold change expression levels were quantified relative to the universal control (N=4-6 for Injected groups and N=2 for Not Injected group). (FIG. 2H) Plasma concentration of Cholesterol, HDL, LDL and ALT (N=3-4). "Universal control" is the level of the transcript of interest in the blood sample collected from a Not Injected mouse, which did not receive any AAV injection. Note for 2B-D and 2C, data of "Not Injected" mouse are also reported in FIG. 1D-F. **P<0.01 and *P<0.05 indicate statistical significance measured by Students' t-test.

(FIG. 3A) Schematic of aptamer-mediated recruitment of repressor domains to CRISPR complex. (FIG. 3B) mRNA expression of targeted genes following aptamer-mediated recruitment of repressor domains to CRISPR complex in HEK293FT cells. Fold changes were quantified relative to dCas9 only control group. N=3 independent transfections.

(FIG. 5A) Scatter plot comparing expression of genes (Fragments Per Kilobase of transcript per Million mapped reads FPKM) in two replicates of bone marrows from Myd88-MS2-HP1aKRAB versus Myd88-MS2-KRAB. Myd88, Il1b, Icam1, Tnfα and l16 are highlighted in red and the most down regulated genes in Myd88-Ms2-HP1a-KRAB groups as compared to MyD88-MS2-KRAB are highlighted in Cyan. (FIG. 5B) GO enrichment Histogram comparing bone marrow samples collected from mice treated with AAV-Myd88-MS2-HP1aKrab versus AAV-Myd88-MS2-Krab. The top 20 significantly enriched terms in the GO enrichment analysis are displayed. * demonstrates padj value <0.05 and significance. Note that pathways such as defense response to bacteria, which are associated with Myd88 signaling are mostly down regulated when HP1aKRAB was used. (FIG. 5C) Reactome Enrichment bar graph displaying the top 20 enriched genes in the Reactome database comparing in the BM samples of Myd88-MS2-HP1aKRAB versus Myd88-MS2-KRAB. * demonstrate significances padj value of <0.05 and significance.

(FIG. 8A) Schematic representation of the gRNA binding sites targeted to the promoter of Myd88 locus. (FIG. 8B) N2A cells were transfected with indicated gRNAs and other components of CRISPR machinery including MS2-HP1aKRAB cassette. Levels of Myd88 repression were analyzed via qRT-PCR 3 days after transfections (N=2). Fold changes are relative to the group that did not receive any gRNA (No Guide). (FIG. 8C) qRT-PCR analysis of in vivo Myd88 expression 3 weeks post retroorbital injection of AAV. Gene expression fold-change was quantified relative to the universal control (N=4-6 for Injected groups and N=2 for Not Injected group). Universal control is the level of the desired transcript in a blood sample collected from a not injected Cas9 transgenic mouse. Note for (FIG. 8C) AAV-Mock-MS2-HP1aKRAB and AAV-Myd88set1-MS2-HP1aKRAB data are also reported in FIG. 1D. *P<0.05; significant (FIG. 10A) Schematic representation of the gRNA binding sites targeted to the promoter of Cxcr4 locus. (FIG. 10B) Raw 264.7 cells were transduced with AAV-CXCR4 along with AAV-Cas9. Expression levels of Cxcr4 mRNA was analyzed using qRT-PCR 5 days post transduction. Fold changes were quantified relative to the expression level of cells receiving the same dosage of AAV-Mock. (N=2). (FIG. 10C) qRT-PCR analysis of in vivo Cxcr4 expression in lung samples 3 weeks post AAV injections to Cas9 transgenic mice. Fold change expression levels were quantified relative to mice receiving the same dosage of AAV-Mock. (N=4) *P<0.05; significant.

INCORPORATION BY REFERENCE

Figures 1A, 1B, 1C, 1D, 1E, 1F, 1G, 1H:
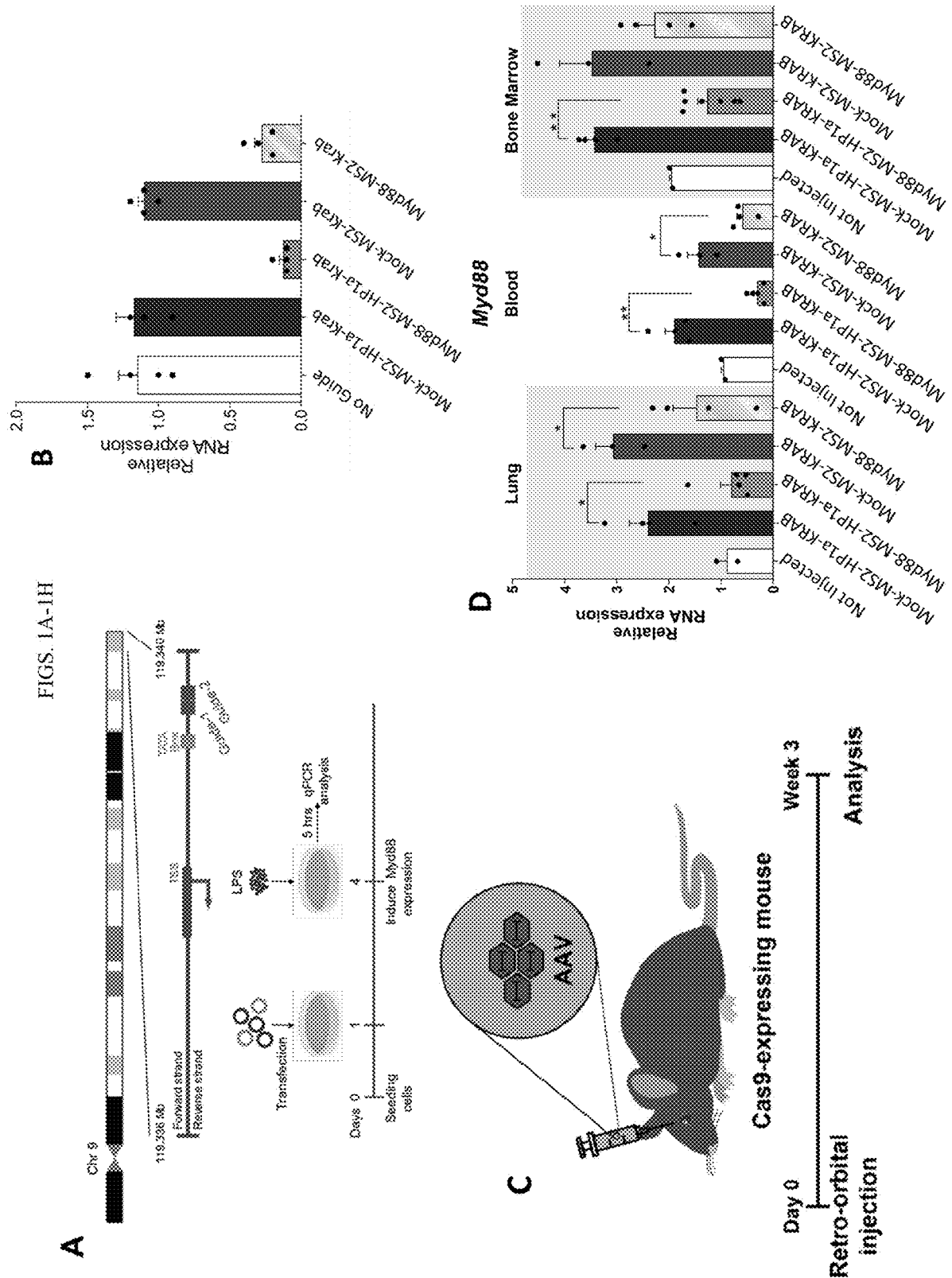
FIGS. 1A-1H show CRISPR-based targeted Myd88 repression in vitro and in vivo demonstrates efficacy in modulating host response against AAV-based gene therapies.
Figures 1A, 1B, 1C, 1D, 1E, 1F, 1G, 1H:
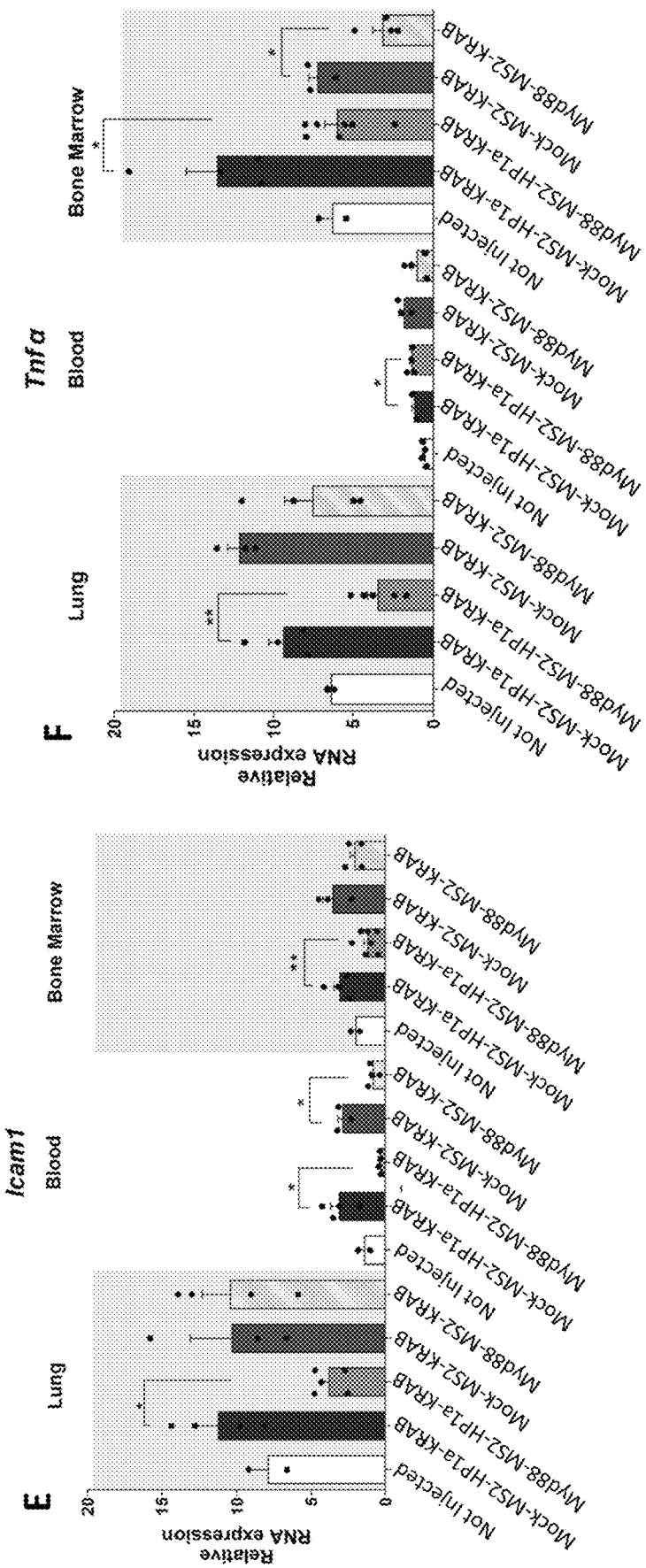
Figures 1A, 1B, 1C, 1D, 1E, 1F, 1G, 1H:
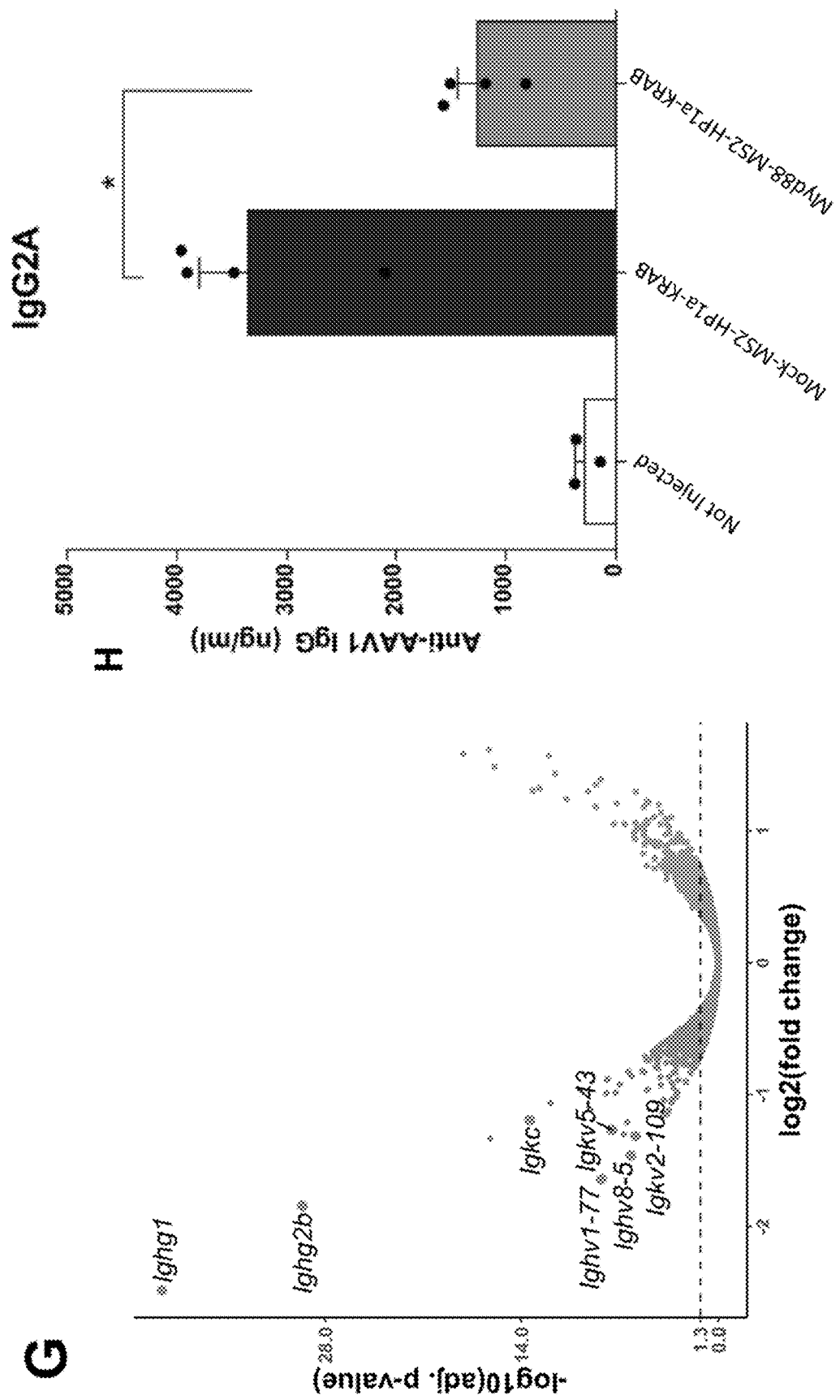

All publications, patents, and patent applications mentioned in this specification are herein incorporated by reference to the same extent as if each individual publication, patent, and patent application was specifically and individually indicated to be incorporated by reference.

DETAILED DESCRIPTION OF THE INVENTION

The present disclosure describes compositions and methods for repressing expression of myeloid differentiation primary response 88 (MyD88) in vivo. The use of the compositions and methods described herein is beneficial for treating or preventing the immune response associated with administration of adeno-associated viral vectors and CRISPR gene editing constructs. Further, the compositions and methods described herein are useful in treating or preventing the aberrant immune response associated with septicemia.

The CRISPR synthetic repressor systems provided herein are configured to inhibit transcription of MyD88. MyD88 is a key node in innate and adaptive immune responses, acting as an essential adaptor molecule for a number of signaling pathways, including Toll-like receptor (TLR) and Interleukin (IL)-1 family signal transduction. Developed using multifunctional Cas nucleases and gRNA aptamers, the synthetic repressor systems modulate endogenous MyD88 levels in vivo and contribute to immunomodulation of the innate and adaptive immune response of the target cell. For example, by introducing into the target cell a multifunctional Cas nuclease along with (i) a gRNA-MS2 aptamer binding target complex complementary to MyD88 and (ii) a repression domain linked to MS2, the synthetic repressor system reduces transcription of MyD88 and downregulates signaling pathways associated with MyD88 function and implicated in the cellular immune response against foreign substances, such as bacteria and viruses.

Accordingly, in some aspects provided herein is a synthetic repression system for modulating in vivo expression of MyD88. In certain embodiments, the system comprises (a) a guide RNA (gRNA) including (i) a guide sequence of 15 or less nucleotides (nt) in length that is complementary to at least a portion of the MyD88 gene and (ii) an aptamer target site specific for an RNA binding protein, (b) a nucleotide sequence encoding the aptamer RNA binding protein fused to a repression domain, and (c) a nucleotide sequence encoding a multifunctional Cas nuclease. In some embodiments, the gRNA nucleotide, the repression domain nucleotide, and the Cas nuclease nucleotide comprise a single amplicon. In certain embodiments, the single amplicon is packaged in a vector for DNA-based viral delivery.

In preferred embodiments, the CRISPR-based synthetic repression system is a single amplicon that can be packaged for in vivo delivery into a mammalian cell using a delivery vector such as an exosome, virus, viral particle, virus-like particle, or nanoparticle. In certain embodiments, provided herein is a synthetic regulatory system comprising, in a single amplicon, a multifunctional Cas nuclease, which is in some cases fused to a repression domain, and a gRNA comprising a guide sequence of 14 nucleotides in length, wherein the synthetic regulatory system modulates cleavage and/or transcription in a mammalian cell.

As used herein, a "guide RNA" (gRNA) refers to a nucleotide sequence including a guide sequence that is complementary to at least a portion of a target gene and a scaffold sequence providing secondary structure and a primary sequence (e.g., tracrRNA) to recruit the Cas nuclease to the target gene. In some embodiments, the gRNA includes secondary structural elements, such as, but not limited to, a hairpin loop, a tetraloop, a stemloop, and combinations thereof. Variations of the gRNA sequence and structure are known in the art. One of skill in the art will recognized the variability tolerance of the gRNA sequence applicable to Cas9 mediated repression that is suitable for the disclosed synthetic repression system. A gRNA target gene also comprises a Protospacer Adjacent Motif (PAM) located immediately downstream from the target site of the target gene. Examples of PAM sequence are known (see, e.g., Shah et al., RNA Biology 10 (5): 891-899, 2013). In some embodiments, the PAM sequence is dependent upon the species of Cas nuclease used in the architecture.

In some embodiments, the guide sequence of the gRNA that is complementary to at least a portion of the target gene is a sequence of about 20 nucleotides (nt). In some embodiments, the guide sequence of the gRNA that is complementary to at least a portion of the target gene is a truncated guide sequence of 15 or less nucleotides (nt). In some embodiments, the gRNA includes a 15-nt guide sequence, a 14-nt guide sequence, or a 13-nt guide sequence. Without being bound by any particular mechanism, theory, or mode of action, the synthetic repression system described herein exploits the ablation of Cas nuclease activity upon binding of the nuclease to a gRNA with 14-nt guide sequence rather than a 20-nt guide sequence. By recruiting the Cas complex to the target site of the target gene but inhibiting the nuclease activity, the Cas complex will not cleave the target gene but will inhibit and repress expression of the target gene. Additional recruitment of repression domains to the stalled Cas complex will augment the repression of the target gene.

In certain embodiments, the gRNA is configured to target one or more endogenous genes. By way of example, endogenous genes targeted for repression can include, without limitation, growth factors, cytokines, genes involved in homology directed repair, genes involved in non-homologous end joining (NHEJ), metabolic enzymes, cell cycle progression enzymes, and genes involved in the pathways of wound healing and tissue repair. In a preferred embodiment, the endogenous gene is MyD88. In some embodiments, the gRNA is configured to target within 200 base pairs (bp) upstream or downstream of the transcription start site of MyD88. In some embodiments, the gRNA is configured to target within 100 bp upstream of the TATA box region in the MyD88 gene. In some embodiments, the guide sequence of the gRNA is selected from the group consisting of SEQ ID NOs:1-4.

To improve gene repression effectiveness and scalability of the system, guide RNAs (gRNAs) are in some cases engineered to comprise a hairpin aptamer target site specific for an RNA binding protein. In some cases, the aptamer target site is appended to the tetraloop and stem loop of a gRNA. RNA recognition motifs are known in the art, such as, but not limited to, the MS2 binding motif, the COM binding motif, or the PP7 binding motif to which certain proteins, MS2 coat protein, COM, or PP7, respectively, bind. In some cases, the aptamer target site is capable of binding to the dimerized MS2 bacteriophage coat proteins. PP7 is the RNA-binding coat protein of the bacteriophage *Pseudomonas*. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously.

In some embodiments, the gRNA is expressed under the control of a RNA Pol II promoter or an RNA Pol III promoter. Examples of pol III promoters include, but are not limited to, U6 and H1 promoters. Examples of pol II promoters include, but are not limited to, the retroviral Rous sarcoma virus (RSV) LTR promoter (optionally with the RSV enhancer), the cytomegalovirus (CMV) promoter (optionally with the CMV enhancer), the SV40 promoter, the dihydrofolate reductase promoter, the β-actin promoter, the phosphoglycerol kinase (PGK) promoter, and the EF1α promoter. In some cases, CRISPR-responsive promoters are used. As used herein, the term "CRISPR-responsive promoter" encompasses eukaryotic promoters as well as synthetic gene regulatory devices and circuits for regulated gene expression. In some embodiments, a CRISPR-responsive promoter comprises a RNA Pol II promoter or an RNA Pol III promoter. The CRISPR-responsive promoter can be a CRISPR-repressible promoter (CRP) or a CRISPR-activatable promoter (CAP).

Standard Pol III promoters, such as U6 and H1, which have been used to express gRNAs and short hairpin RNAs (shRNA), do not allow spatial or temporal control of downstream genes. Spatial limitation of CRISPR gRNAs have several important benefits, particularly with regards to human therapeutics: 1) limiting gRNA expression to tissue/cell type of interest, which eliminates the concern that delivery tools distribute the CRISPR coding cassette systematically; 2) avoiding germline mutations by eliminating concern over CRISPR activity in germ cells; 3) differential gene editing/modulation in neighboring or cross-talking cells: gRNA regulation by distinct cell type-specific promoters enables scientists to modulate the expression of different set of genes in distinct cell types. Accordingly, in certain embodiments, the CRISPR-based genetic circuit is configured to drive expression of a guide RNA (gRNA) using a cell type-specific promoter. In some cases, a CRISPR-based genetic circuit is configured to comprise an endogenous or cell type-specific promoter in place of a synthetic promoter. For example, a synthetic RNA Pol II or Pol III promoter can be swapped with a cell type- or context-specific promoter and interfaced with intracellular signaling, enabling multi-step sensing and modulation of cellular behavior. In some cases, a transcriptional repression cascade comprises two, three, or four interconnected CRISPR transcriptional repression circuits (NAND logic gates).

A promoter, generally, is a region of nucleic acid that initiates transcription of a nucleic acid encoding a product. A promoter may be located upstream (e.g., 0 bp to −100 bp, −30 bp, −75 bp, or −90 bp) from the transcriptional start site of a nucleic acid encoding a product, or a transcription start site may be located within a promoter. A promoter may have a length of 100-1000 nucleotide base pairs, or 50-2000 nucleotide base pairs. In some embodiments, promoters have a length of at least 2 kilobases (e.g., 2-5 kb, 2-4 kb, or 2-3 kb).

In certain embodiments, gRNA expression from RNA pol II promoters can be modulated using Csy4 endoribonuclease-mediated cleavage. In some cases, multiple gRNAs are placed in tandem from a single coding region processed by Csy4. In some cases, high ON/OFF ratios are achieved by using a modified U6-driven 14-nt gRNA cassette, where 20-nt gRNA target sites are inserted within both the U6 promoter site and body of the gRNA. This structure forms a second generation kill switch which enables full destruction of the 14-nt gRNA cassette upon expression of 20-nt gRNAs in vitro, in vivo, and ex vivo. In some cases, such kill switches are expressed in vivo in, for example, in tissues that are frequent targets in gene therapy and are tolerogenic immune environments. Additional embodiments of Cas-mediated kill switches suitable for use in the synthetic repressor systems described herein are described in PCT Publication No. WO 2019/005856, which is incorporated herein by reference in its entirety.

In some cases, the RNA binding protein (e.g., MS2, COM, or PCP) specific for the aptamer target site incorporated in the gRNA is fused to a repression domain such as, for example, a Kruppel associated box (KRAB) domain. Other suitable repression domains are known in the art including, but not limited to, methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), and heterochromatin protein 1 (HP1A). In some embodiments, the RNA binding protein is fused to KRAB and at least one additional repression domain. In some embodiments, the RNA binding protein MS2 is fused to KRAB and at least one additional repression domain. In some embodiments, MS2 is fused to KRAB and HP1A. In some embodiments, MS2 is fused to KRAB and MECP2. In some embodiments, MS2 is fused to MECP2, KRAB, and MBD2B. In some embodiments, MS2 is fused to MBD2B and HP1A. In some embodiments, the RNA binding protein—repression domain fusion is encoded from an engineered nucleic acid.

In some embodiments, the RNA binding protein and at least one repression domain are fused to a multifunctional Cas nuclease. In some embodiments, multifunctional Cas nuclease is encoded from an engineered nucleic acid. For example, in certain embodiments, transcriptional modifiers are fused to a multifunctional Cas nuclease to enable site-specific transcriptional modifications. Various strategies can be used to engineer such fusion molecules. In some cases, transcriptional modulators are directly fused to a multifunctional Cas nuclease. In other cases, the modulator is fused to another RNA binding protein such as MS2 bacteriophage coat protein in order to recruit the modulator to the Cas/gRNA/DNA complex.

In some cases, the multifunctional Cas nuclease is fused to a repression domain. In other cases, repression is achieved without the use of any repression domain but, rather, through Cas nuclease-mediated steric hindrance. The repression domain can comprise an RNA binding protein (e.g., MS2) fused to a repression domain such as, for example, a Kruppel associated box (KRAB) domain. Other suitable repression domains are described herein.

The components of synthetic repression systems described herein are preferably provided in a single amplicon. In some cases, however, the components may be in the form of two or more polynucleotide sequences. In such cases, a synthetic repression system can comprise introducing into a single cell three cassettes comprising components of a CRISPR-based synthetic repression system, where the first cassette comprises a nucleotide sequence encoding a polypeptide of a multifunctional Cas9 nuclease, a second cassette comprises the gRNA construct, and a third cassette encodes the RNA binding protein-repression domain fusion. In some embodiments, the synthetic repression system comprises introducing into a single cell two cassettes comprising components of a CRISPR-based synthetic repression system, where the first cassette comprises a nucleotide encoding a polypeptide of a multifunctional Cas9 nuclease fused to a repression domain and the second cassette comprises the gRNA construct. In some embodiments, one or more of the cassettes may be under the control of an inducible promoter. In some cases, it will be advantageous to fuse a multifunctional Cas9 nuclease to a reporter polypeptide or other polypeptide of interest (e.g., a therapeutic protein). The reporter polypeptide may be a fluorescent polypeptide such as near infrared fluorescent protein (iRFP) (to monitor Cas9 protein dynamics).

In some cases, an activator of the inducible promoter is provided by a cassette comprising the safety construct, such as those described in PCT Publication No. WO 2019/005856, which is incorporated herein by reference in its entirety. Activators can mediate or promote recruitment of polymerase machinery to the CRISPR-Cas complex. The activator can be a zinc-finger protein fused to an activation domain such as a VP16 transcription activation domain or VP64 transcription activation domain. In certain embodiments, orthogonally acting protein-binding RNA aptamers such as MS2 are used for aptamer-mediated recruitment of an activator to the CRISPR-Cas complex. For example, an MS2-VPR fusion protein can be used to aid CRISPR-CAS/14-nt gRNA-mediated gene activation by means of aptamer-mediated recruitment of an activator to the CRISPR-Cas complex. In the presence of an inducer, a safety 20-nt gRNA is expressed, resulting in destruction of the 14-nt gRNA cassette. The synthetic regulatory circuit can be an engineered polynucleotide.

As used herein, the terms "engineered nucleic acid" and "engineered polynucleotide" are used interchangeably and refer to a nucleic acid that has been designed and made using known in vitro techniques in the art. In some embodiments, an engineered polynucleotide, also referred to as a circuit herein, is a nucleic acid that is not isolated from the genome of an organism. In some embodiments, the engineered polynucleotide is introduced to a cell, plurality of cells, an organ or an organism to perform diverse functions (e.g., differentiation of cells, as sensors within cells, program a cell to act as a sensor, and delivery of selective cell-based therapies).

In some embodiments, the engineered polynucleotide comprises one or more promoters, such as an inducible promoter, constitutive promoter, or a tissue-specific or cell type-specific promoter. Inducible promoters allow regulation of gene expression and can be regulated by exogenously supplied compounds, environmental factors such as temperature, or the presence of a specific physiological state, e.g., acute phase, a particular differentiation state of the cell, or in replicating cells only. In some cases, the cell type specific promoter is a germ cell-specific promoter such as, for example, aphosphoglycerate kinase 2 (Pgk2) promoter. Inducible promoters and inducible systems are known and available from a variety of commercial sources, including, without limitation, Invitrogen, Clontech, and Ariad. Many other systems have been described and can be readily selected by one of skill in the art. Examples of inducible promoters regulated by exogenously supplied promoters include the zinc-inducible sheep metallothionine (MT) promoter, the dexamethasone (Dex)-inducible mouse mammary tumor virus (MMTV) promoter, the T7 polymerase promoter system [WO 98/10088]; the ecdysone insect promoter [No et al, Proc. Natl. Acad. Sci. USA, 93:3346-3351 (1996)], the tetracycline-repressible system [Gossen et al, Proc. Natl. Acad. Sci. USA, 89:5547-5551 (1992)], the tetracycline-inducible system [Gossen et al, Science, 268: 1766-1769 (1995), see also Harvey et al, Curr. Opin. Chem. Biol., 2:512-518 (1998)], the RU486-inducible system [Wang et al, Nat. Biotech., 15:239-243 (1997) and Wang et al, Gene Ther., 4:432-441 (1997)] and the rapamycin-inducible system [Magari et al, J. Clin. Invest., 100:2865-2872 (1997)]. Still other types of inducible promoters which may be useful in this context are those which are regulated by a specific physiological state, e.g., temperature, acute phase, a particular differentiation state of the cell, or in replicating cells only. Non-limiting examples of control elements include promoters, activators, repressor elements, insulators, silencers, response elements, introns, enhancers, transcriptional start sites, termination signals, linkers and poly(A) tails. Any combination of such control elements is contemplated herein (e.g., a promoter and an enhancer).

In some embodiments, the promoter is a lung specific promoter. Suitable lung specific promoters are known in the art and include, but are not limited to an albumin promoter and a human alpha-1 anti-trypsin promoter. In some embodiments, the promoter is a blood specific promoter. In some embodiments, the promoter is a bone marrow specific promoter. In some embodiments, the promoter is a macrophage specific promoter, such as CD11B. In some embodiments the promoter is a B cell specific promoter, such as CD19. In some embodiments, the promoter is a dendritic cell specific promoter, such as CD11C. In some embodiments, the promoter is a T cell specific promoter, such as CD4 and CD8.

CRISPR systems belong to different classes, with different repeat patterns, sets of genes, and species ranges. A CRISPR enzyme is typically a type I or III CRISPR enzyme. The CRISPR system is derived advantageously from a type II CRISPR system. The type II CRISPR enzyme may be any Cas enzyme. The terms "Cas" and "CRISPR-associated Cas" are used interchangeably herein. The Cas enzyme can be any naturally-occurring nuclease as well as any chimeras, mutants, homologs, or orthologs. In some embodiments, one or more elements of a CRISPR system is derived from a particular organism comprising an endogenous CRISPR system, such as Streptococcus pyogenes (SP) CRISPR systems or Staphylococcus aureus (SA) CRISPR systems. The CRISPR system is a type II CRISPR system and the Cas enzyme is Cas9 or a catalytically inactive Cas9 (dCas9). Other non-limiting examples of Cas proteins include Cas1, Cas1B, Cas2, Cas3, Cas4, Cas5, Cash, Cas7, Cas8, Cas9 (also known as Csn1 and Csx12), Cas10, Csy1, Csy2, Csy3, Cse1, Cse2, Csc1, Csc2, Csa5, Csn2, Csm2, Csm3, Csm4, Csm5, Csm6, Cmr1, Cmr3, Cmr4, Cmr5, Cmr6, Csb1, Csb2, Csb3, Csx17, Csx14, Csx10, Csx16, CsaX, Csx3, Csx1, Csx15, Csf1, Csf2, Csf3, Csf4, homologues thereof, or modified versions thereof. A comprehensive review of the Cas protein family is presented in Haft et al. (2005) Computational Biology, PLoS Comput. Biol. 1:e60. At least 41 CRISPR-associated (Cas) gene families have been described to date.

It will be understood that the CRISPR-Cas system as described herein is non-naturally occurring in a cell, i.e. engineered or exogenous to the cell. The CRISPR-Cas system as referred to herein has been introduced in a cell. Methods for introducing the CRISPR-Cas system in a cell are known in the art, and are further described herein elsewhere. The cell comprising the CRISPR-Cas system, or having the CRISPR-Cas system introduced, according to the invention comprises or is capable of expressing the individual components of the CRISPR-Cas system to establish a functional CRISPR complex, capable of modifying (such as cleaving) a target DNA sequence. Accordingly, as referred to herein, the cell comprising the CRISPR-Cas system can be a cell comprising the individual components of the CRISPR-Cas system to establish a functional CRISPR complex, capable of modifying (such as cleaving) a target DNA sequence. Alternatively, as referred to herein, and preferably, the cell comprising the CRISPR-Cas system can be a cell comprising one or more nucleic acid molecule encoding the individual components of the CRISPR-Cas system, which can be expressed in the cell to establish a functional CRISPR complex, capable of modifying (such as cleaving) a target DNA sequence.

In some embodiments, a synthetic CRISPR-based repression system as described herein may be introduced into a biological system (e.g., a virus, prokaryotic or eukaryotic cell, zygote, embryo, plant, or animal, e.g., non-human animal). A prokaryotic cell may be a bacterial cell. A eukaryotic cell may be, e.g., a fungal (e.g., yeast), invertebrate (e.g., insect, worm), plant, vertebrate (e.g., mammalian, avian) cell. A mammalian cell may be, e.g., a mouse, rat, non-human primate, or human cell. A cell may be of any type, tissue layer, tissue, or organ of origin. In some embodiments a cell may be, e.g., an immune system cell such as a lymphocyte or macrophage, a fibroblast, a muscle cell, a fat cell, an epithelial cell, or an endothelial cell. A cell may be a member of a cell line, which may be an immortalized mammalian cell line capable of proliferating indefinitely in culture.

To achieve endogenous repression of multiple genes, repression domains are included in multiple gRNAs. In some cases, the gRNAs further comprise one or more aptamers such as MS2, COM, or PP7 to which certain proteins (MS2 coat protein, COM, or PCP, respectively) bind. The repression domain is fused to the aptamer binding protein and, thus, will be recruited to the Cas9/gRNA complex to achieve repression of transcription of endogenous genes. PP7 is the RNA-binding coat protein of the bacteriophage Pseudomonas. Like MS2, it binds a specific RNA sequence and secondary structure. The PP7 RNA-recognition motif is distinct from that of MS2. Consequently, PP7 and MS2 can be multiplexed to mediate distinct effects at different genomic loci simultaneously.

In some cases, SMASh or another degradation/destabilization domain is fused to Cas9 nuclease or other protein fusion described herein. In general, destabilizing domains are small protein domains that are unstable and degraded in the absence of ligand, but whose stability is rescued by binding to a high-affinity cell-permeable ligand. Genetic fusion of a destabilizing domain to a protein of interest results in degradation of the entire fusion. Addition of a ligand for the destabilizing domain protects the fusion from degradation and, in this manner, adds ligand-dependent stability to a protein of interest.

In some cases, a viral or plasmid vector system is employed for delivery of a synthetic CRISPR-based repression system described herein. Preferably, the vector is a viral vector, such as a lenti- or baculo- or preferably adeno-viral/adeno-associated viral vectors, but other means of delivery are known (such as yeast systems, microvesicles, gene guns/means of attaching vectors to gold nanoparticles) and are provided. In some embodiments, one or more of the viral or plasmid vectors may be delivered via liposomes, nanoparticles, exosomes, microvesicles, or a gene-gun. In certain preferred embodiments, CRISPR-based repression system or components thereof (e.g., gRNAs) are packaged for delivery to a cell in one or more viral delivery vectors. Suitable viral delivery vectors include, without limitation, adeno-viral/adeno-associated viral (AAV) vectors, lentiviral vectors, and Herpes Simplex Virus 1 (HSV-1) vectors. For example, a synthetic CRISPR-based repression system can be introduced into one or more Herpes simplex amplicon vectors.

In some embodiments, the synthetic CRISPR-based repression system is introduced into one or more AAV vectors. In some embodiments, the AAV vector is a AAV2/1 vector. As used herein, "AAV2/1 vector" refers to a recombinant adeno-associated viral vector including AAV2 inverted terminal repeats and AAV1 Rep and Cap genes. Other suitable AAV vectors are known in the art, such as, but not limited to AAV1.

Viral vectors and viral particles are commonly used viral delivery platforms for gene therapy. Therefore, for faster clinical translation, CRISPR-based genetic circuits described herein can be constructed using embedded kill switches and incorporated into Herpes simplex amplicon vectors. Preferably, a single carrier vector is used to achieve transfection of all synthetic genetic components to target cells. Without being bound to any particular theory or mode of action, it is believed that the ability to control CRISPR functionality, by adding only cleaving 20-nt gRNAs, provide an ideal safety kill switch mechanism due to the small DNA footprint of gRNA and limited pay load capacity of viral particles. In some cases, a Herpes simplex viral (HSV) delivery system is used for delivery of engineered polynucleotides. In other cases, non-viral particles can be used for delivery. For example, controlled spatial transfection and/or destruction of CRISPR genetic circuits is achieved by assembling and packaging of all CRISPR-based genetic circuit elements in HSV-1 amplicon vectors having large payload capacity (150 kb) and capable of infecting multiple target cells.

In another aspect, provided herein is a co-virus strategy, where the method comprises introducing into a single cell two AAV vectors. The first vector carries (i) a nucleotide sequence encoding a fusion polypeptide of a Cas9 nuclease, and (ii) a gRNA configured for gene modulation as described herein. In some cases, the Cas9 nuclease is fused to a reporter polypeptide. The reporter polypeptide may be a fluorescent polypeptide such as near infrared fluorescent protein (iRFP) (to monitor Cas9 protein dynamics). The second vector is the "safety vector" and carries a 20-nt controllable gRNA as described in PCT Publication No. WO 2019/005856, which is incorporated herein by reference in its entirety. To ensure that expression of the Cas9-iRFP fusion polypeptide carried by the first virus occurs only in cells into which both AAV vectorss are introduced, expression of the fusion polypeptide is under the control of an inducible promoter. In some cases, an activator of the inducible promoter is carried by the safety virus. Activators can mediate or promote recruitment of the Pol II machinery to the CRISPR-Cas complex. The activator can be a zinc-finger protein fused to an activation domain such as a VP16 transcription activation domain or VP64 transcription activation domain. In certain embodiments, orthogonally acting protein-binding RNA aptamers such as MS2 are used for aptamer-mediated recruitment of an activator to the CRISPR-Cas complex. For example, the second virus (safety virus) can carry an MS2-VPR fusion protein that aids in CRISPR-CAS and 14-nt gRNA-mediated gene activation by means of aptamer-mediated recruitment of an activator to the CRISPR-Cas complex. In the presence of an inducer, the safety 20-nt gRNA is expressed, resulting in destruction of the 14-nt gRNA cassette.

Applications of the CRISPR-based genetic circuits described herein include, without limitation, in vivo CRISPR-based precision gene therapies for treating chronic and acute conditions in a variety of cell types; a platform of CRISPR cell classifiers can be applied to various cells, tissues, or organs for various therapeutic and/or preventative applications; and in vivo interrogation of endogenous genes using CRISPR activators and repressors, including CRISPR-mediated endogenous gene activation. By way of example, therapeutic applications include, without limitation, treating septicemia in subject, preventing or treating an immune response in a subject, and treating Waldenström macroglobulinemia.

In certain aspects, provided herein are methods for treating septicemia, methods for treating or preventing an immune response in a subject, and methods for treating Waldenström macroglobulinemia. The methods of treatment or prevention described herein include administration to a subject in need thereof a pharmaceutical composition comprising a therapeutically effective amount of the CRISPR-based synthetic repression system described herein or the polynucleotides and vectors encoding the CRISPR-based synthetic repression system described herein. As used herein, the term "pharmaceutical composition" refers to a chemical or biological composition suitable for administration to a mammal. Such compositions typically include the active agent and a pharmaceutically acceptable carrier. As used herein the term "pharmaceutically acceptable carrier" includes saline, solvents, dispersion media, coatings, antibacterial and antifungal agents, isotonic and absorption delaying agents, and the like, compatible with pharmaceutical administration. Supplementary active compounds can also be incorporated into the compositions. Examples of compositions appropriate for such therapeutic applications include preparations for parenteral, subcutaneous, transdermal, intradermal, intramuscular, intracoronarial, intramyocardial, intraperitoneal, intravenous or intraarterial (e.g., injectable), or intratracheal administration, such as sterile suspensions, emulsions, and aerosols. In some cases, pharmaceutical compositions appropriate for therapeutic applications may be in admixture with one or more pharmaceutically acceptable excipients, diluents, or carriers such as sterile water, physiological saline, glucose or the like. For example, compositions of the CRISPR-based synthetic repression system described herein can be administered to a subject as a pharmaceutical composition comprising a carrier solution.

Formulations may be designed or intended for oral, rectal, nasal, systemic, topical or transmucosal (including buccal, sublingual, ocular, vaginal and rectal) and parenteral (including subcutaneous, intramuscular, intravenous, intraarterial, intradermal, intraperitoneal, intrathecal, intraocular and epidural) administration. In general, aqueous and non-aqueous liquid or cream formulations are delivered by a parenteral, oral or topical route. In other embodiments, the compositions may be present as an aqueous or a non-aqueous liquid formulation or a solid formulation suitable for administration by any route, e.g., oral, topical, buccal, sublingual, parenteral, aerosol, a depot such as a subcutaneous depot or an intraperitoneal or intramuscular depot. In some cases, pharmaceutical compositions are lyophilized. In other cases, pharmaceutical compositions as provided herein contain auxiliary substances such as wetting or emulsifying agents, pH buffering agents, gelling or viscosity enhancing additives, preservatives, flavoring agents, colors, and the like, depending upon the route of administration and the preparation desired. The pharmaceutical compositions may be formulated according to conventional pharmaceutical practice (see, e.g., Remington: *The Science and Practice of Pharmacy,* 20th edition, 2000, ed. A. R. Gennaro, Lippincott Williams & Wilkins, Philadelphia, and *Encyclopedia of Pharmaceutical Technology*, eds. J. Swarbrick and J. C. Boylan, 1988-1999, Marcel Dekker, New York). For intravenous administration, suitable carriers include physiological saline, bacteriostatic water, Cremophor EL® (BASF, Parsippany, N.J., USA) or phosphate buffered saline (PBS). In all cases, a composition for parenteral administration must be sterile and should be formulated for ease of injectability. The composition should be stable under the conditions of manufacture and storage, and must be shielded from contamination by microorganisms such as bacteria and fungi.

In some embodiments, solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity, such as sodium chloride or dextrose. The pH can be adjusted with acids or bases, such as hydrochloric acid or sodium hydroxide. The preparation can be enclosed in ampoules, disposable syringes or multiple-dose vials made of glass or plastic. For convenience of the patient or treating physician, the dosing formulation can be provided in a kit containing all necessary equipment (e.g., vials of drug, vials of diluent, syringes and needles) for a course of treatment (e.g., 7 days of treatment).

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle, which contains a basic dispersion medium and the required other ingredients from those enumerated above. In the case of sterile powders for the preparation of sterile injectable solutions, typical methods of preparation include vacuum drying and freeze drying, which can yield a powder of the active ingredient plus any additional desired ingredient from a previously sterile-filtered solution thereof.

The preferred route may vary with, for example, the subject's pathological condition or age or the subject's response to therapy or that is appropriate to the circumstances. The formulations can also be administered by two or more routes, where the delivery methods are essentially simultaneous or they may be essentially sequential with little or no temporal overlap in the times at which the composition is administered to the subject.

Suitable regimes for initial administration and further doses or for sequential administrations also are variable, may include an initial administration followed by subsequent administrations, but nonetheless, may be ascertained by the skilled artisan from this disclosure, the documents cited herein, and the knowledge in the art.

In some embodiments, compositions of the CRISPR-based synthetic repression system described herein are administered to a subject in need thereof using an infusion, topical application, surgical transplantation, or implantation. In an exemplary embodiments, administration is systemic. In such cases, compositions of the CRISPR-based synthetic repression system described herein can be provided to a subject in need thereof in a pharmaceutical composition adapted for intravenous administration to subjects. Typically, compositions for intravenous administration are solutions in sterile isotonic aqueous buffer. The use of such buffers and diluents is well known in the art. Where necessary, the composition may also include a local anesthetic to ameliorate any pain at the site of the injection. Generally, the ingredients are supplied either separately or mixed together in unit dosage form, for example, as a cryopreserved concentrate in a hermetically sealed container such as an ampoule indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration. In some cases, compositions of the CRISPR-based synthetic repression system described herein are lyophilized prior to administration.

In one embodiment, compositions of the CRISPR-based synthetic repression system described herein are administered intravenously. For example, an agent of the present technology may be administered via rapid intravenous bolus injection. In some embodiments, the agent of the present technology is administered as a constant-rate intravenous infusion.

The agent of the present technology may also be administered orally, topically, intranasally, intramuscularly, subcutaneously, or transdermally. In one embodiment, transdermal administration is by iontophoresis, in which the charged composition is delivered across the skin by an electric current.

Other routes of administration include intracranio-ventricular, intracerebroventricularly or intrathecally. Intracerebroventricularly refers to administration into the ventricular system of the brain. Intrathecally refers to administration into the space under the arachnoid membrane of the spinal cord. Thus, in some embodiments, intracerebroventricular or intrathecal administration is used for those diseases and conditions which affect the organs or tissues of the central nervous system.

For systemic, intracerebroventricular, intrathecal, topical, intranasal, subcutaneous, or transdermal administration, formulations of the agents of the present technology may utilize conventional diluents, carriers, or excipients etc., such as those known in the art to deliver the agents of the present technology. For example, the formulations may comprise one or more of the following: a stabilizer, a surfactant, such as a nonionic surfactant, and optionally a salt and/or a buffering agent. The agents of the present technology may be delivered in the form of an aqueous solution, or in a lyophilized form.

Therapeutically effective amounts of compositions of the CRISPR-based synthetic repression system described herein are administered to a subject in need thereof. An effective dose or amount is an amount sufficient to effect a beneficial or desired clinical result. With regard to methods of the present invention, the effective dose or amount, which can be administered in one or more administrations, is the amount of compositions of the CRISPR-based synthetic repression system described herein sufficient to elicit a therapeutic effect in a subject to whom the agent is administered. The dosage ranges described herein are exemplary and are not intended to be limiting. Dosage, toxicity, and therapeutic efficacy of the agents of the present technology can be determined by standard pharmaceutical procedures in cell cultures or experimental animals, e.g., for determining the LD50 (the dose lethal to 50% of the population) and the ED50 (the dose therapeutically effective in 50% of the population). The dose ratio between toxic and therapeutic effects is the therapeutic index and it can be expressed as the ratio LD50/ED50.

The data obtained from the cell culture assays and animal studies can be used in formulating a range of dosage for use in humans. The dosage of such compounds lies preferably within a range of circulating concentrations that include the ED50 with little or no toxicity. The dosage may vary within this range depending upon the dosage form employed and the route of administration utilized. For any agent of the present technology used in the methods described herein, the therapeutically effective dose can be estimated initially from cell culture assays. A dose can be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Typically, an effective amount of the compositions of the CRISPR-based synthetic repression system described herein, sufficient for achieving a therapeutic or prophylactic effect, ranges from about $1\times10^9$ genome copies (GC)/kilogram (kg) body weight to about $1\times10^{14}$ GC/kg body weight. In some embodiments, the dosage ranges will be from about $1\times10^9$ GC/kg body weight per day to about $1\times10^{14}$ GC/kg body weight per day. For example dosages between about $1\times10^9$ GC/kg body weight to about $1\times10^{14}$ GC/kg body weight can be administered every day, every two days or every three days or within the range of $1\times10^9$ GC/kg body weight to about $1\times10^{14}$ GC/kg body weight every week, every two weeks or every three weeks. In one embodiment, a single dosage of the agent of the present technology ranges from $1\times10^9$ GC/kg body weight to about $1\times10^{14}$ GC/kg body weight. An exemplary treatment regimen entails administration once per day or once a week. In therapeutic applications, a relatively high dosage at relatively short intervals is sometimes required until progression of the disease is reduced or terminated, or until the subject shows partial or complete amelioration of symptoms of disease. Thereafter, the patient can be administered a prophylactic regimen. The schedule of doses is optimized to maintain the therapeutic concentration at the target tissue, such as by single daily or weekly administration, but also including continuous administration (e.g., parenteral infusion or transdermal application).

The skilled artisan will appreciate that certain factors may influence the dosage and timing required to effectively treat a subject, including but not limited to, the severity of the disease or disorder, previous treatments, the general health and/or age of the subject, and the presence of other diseases. Moreover, treatment of a subject with a therapeutically effective amount of the therapeutic compositions described herein can include a single treatment or a series of treatments.

In some aspects, provided herein are methods for treating septicemia in a subject. Methods of treating septicemia include administering to a subject with or at risk for septicemia a therapeutically effective amount of the compositions of the CRISPR-based synthetic repression system described herein and specific for repression of MyD88. Due to its role in innate and adaptive immunity, repression of MyD88 will result in reduction of the aberrant immune response associated with septicemia. A subject treated with the compositions described herein may have a reduction in the levels of immune related markers Icam-1, Tnfα, Ncf, and Il6, Ifn-α, Ifn-β, Ifn-γ, and Stat4 as compared to the level of the immune related marker prior to treatment. In some embodiments, the levels of immune related markers Icam-1, Tnfα, Ncf, and Il6, Ifn-α, Ifn-β, Ifn-γ, and Stat4 are compared to an internal or external control or reference standard. A subject treated with the compositions described herein may have a reduction in the levels of lung and blood serum cytokines as compared to the level of the cytokines prior to treatment. A subject treated with the compositions described herein may have a reduction in serum lactate levels as compared to the level measured prior to treatment.

In some aspects, provided herein are methods for treating or preventing an adverse immune response in a subject receiving an adeno-associated viral vector gene therapy or a CRISPR-based gene therapy. Methods of preventing an adverse immune response in a subject include administering to a subject a therapeutically effective amount of the compositions of the CRISPR-based synthetic repression system described herein and specific for repression of MyD88 prior to administration of an AAV vector therapy to the subject. The compositions described herein may be administrated prior to or at the same time as the AAV vector therapy. In some embodiments, the subject has received or will receive multiple courses of an AAV vector therapy treatment and the compositions described herein are administrated prior to, immediately after or concurrently with the AAV vector treatment. A subject treated with the compositions described herein may have a reduction in the levels of immune related markers Icam-1, Tnfα, Ncf, Il6, Ifn-α, Ifn-β, Ifn-γ, and Stat4 as compared to the level of the immune related markers observed in a subject who received the AAV vector therapy but not the compositions of the CRISPR-based synthetic repression system described herein and specific for repression of MyD88. A subject treated with the compositions described herein may have a reduction in the levels of lung and blood serum cytokines as compared to the level of the immune related markers observed in a subject who received the AAV vector therapy but not the compositions of the CRISPR-based synthetic repression system described herein and specific for repression of MyD88.

In some embodiments, the methods of treatment include monitoring the level of at least one immune related marker selected from the group consisting of Icam-1, Tnfα, Ncf, Il6, Ifn-α, Ifn-β, Ifn-γ, and Stat4 and re-administering the compositions of the CRISPR-based synthetic repression system described herein and specific for repression of MyD88 to the subject until the level of the at least one marker decreases or returns to the level prior to the subject receiving the AAV vector therapy or prior to the subject having septicemia.

In some aspects, provided herein are methods for the treatment of Waldenström macroglobulinemia. Waldenström macroglobulinemia is a type of non-Hodgkin lymphoma characterized by unchecked lymphocyte proliferation and macroglobulin production. Myd88 mutation L265P supports malignant growth through NF-κB signaling and its inhibition is associated with decreased survival of cancer cells. Methods for treating Waldenström macroglobulinemia in a subject include administering to a subject in need thereof the compositions of the CRISPR-based synthetic repression system described herein and specific for repression of MyD88. In some embodiments, the CRISPR-based synthetic repression system described herein represses endogenous, mutant MyD88 expression and is designed to use homology directed repair (HDR) to correct the L265P mutation. In some embodiments, the composition additionally includes gRNA specific for Cas nuclease cleavage near the L265 locus of MyD88 and includes an HDR template encoding the correct wild-type sequence at the L265 locus.

So that the compositions, methods, and systems provided herein may more readily be understood, certain terms are defined:

As used in this specification and the appended claims, the singular forms "a," "an," and "the" include plural references unless the context clearly dictates otherwise. Any reference to "or" herein is intended to encompass "and/or" unless otherwise stated.

The terms "comprising", "comprises" and "comprised of" as used herein are synonymous with "including", "includes" or "containing", "contains", and are inclusive or open-ended and do not exclude additional, non-recited members, elements, or method steps. The phraseology and terminology used herein is for the purpose of description and should not be regarded as limiting. The use of "including," "comprising," "having," "containing," "involving," and variations thereof, is meant to encompass the items listed thereafter and additional items. Use of ordinal terms such as "first," "second," "third," etc., in the claims to modify a claim element does not by itself connote any priority, precedence, or order of one claim element over another or the temporal order in which acts of a method are performed. Ordinal terms are used merely as labels to distinguish one claim element having a certain name from another element having a same name (but for use of the ordinal term), to distinguish the claim elements.

As used herein, the terms "synthetic" and "engineered" are used interchangeably and refer to the aspect of having been manipulated by the hand of man.

As used herein, "modifying" ("modify") one or more target nucleic acid sequences refers to changing all or a portion of a (one or more) target nucleic acid sequence and includes the cleavage, introduction (insertion), replacement, and/or deletion (removal) of all or a portion of a target nucleic acid sequence. All or a portion of a target nucleic acid sequence can be completely or partially modified using the methods provided herein. For example, modifying a target nucleic acid sequence includes replacing all or a portion of a target nucleic acid sequence with one or more nucleotides (e.g., an exogenous nucleic acid sequence) or removing or deleting all or a portion (e.g., one or more nucleotides) of a target nucleic acid sequence. Modifying the one or more target nucleic acid sequences also includes introducing or inserting one or more nucleotides (e.g., an exogenous sequence) into (within) one or more target nucleic acid sequences.

Unless otherwise defined, all terms used in this disclosure, including technical and scientific terms, have the meaning as commonly understood by one of ordinary skill in the art to which this invention belongs.

Although this description refers to certain aspects or embodiments, such aspects or embodiments are illustrative and non-exhaustive in nature. Having reviewed the present disclosure, persons of ordinary skill in the art will readily recognize and appreciate that numerous other possible variations or alternative configurations or aspects are possible and were contemplated within the scope of the present disclosure.

Example 1

The embodiments described here demonstrate use of a CRISPR-based synthetic repression system to repress endogenous MyD88 expression in vitro and in vivo.

The embodiment described here employs the notion of CRISPR Multifunctionality, reported previously (see Dahlman, J. E. et al. "Orthogonal gene knockout and activation with a catalytically active Cas9 nuclease," *Nature biotechnology* 33, 1159 (2015), and Kiani, S. et al. "Cas9 gRNA engineering for genome editing, activation and repression," *Nature methods* 12, 1051 (2015), each of which is incorporated herein by reference). The ability to switch between nuclease-dependent and -independent functions of a single Cas9 protein, offers exciting possibilities to combine gene editing with epigenetic manipulations. Inventors previously reported that truncation of guide RNA (gRNA) from 5' end, enables the application of a nuclease competent Cas9 protein for transcriptional modulation of genes. Liao et al. recently demonstrated the utility of this system in vivo for transcriptional activation of genes. (Liao, H.-K. et al. "In vivo target gene activation via CRISPR/Cas9-mediated trans-epigenetic modulation," *Cell* 171, 1495-1507. e1415 (2017)). However, the wider utility of this concept for transcriptional repression or simultaneous DNA cleavage/transcriptional modulation and in clinically relevant conditions remain to be examined. This disclosure describes technologies that exploit this notion in the context of safety and controllability of CRISPR-based in vivo therapies.

Myeloid differentiation primary response 88 (MyD88) is a key node in innate and adaptive immune responses, acting as an essential adaptor molecule for a number of signaling pathways, including Toll-like receptor (TLR) and Interleukin (IL)-1 family signal transduction. Given the central role of MyD88 signaling in innate and adaptive immunity, the inventors set out to determine whether the inventors can achieve synthetic immunomodulation through regulation of endogenous Myd88 levels in vivo.

Figures 3A, 3B:
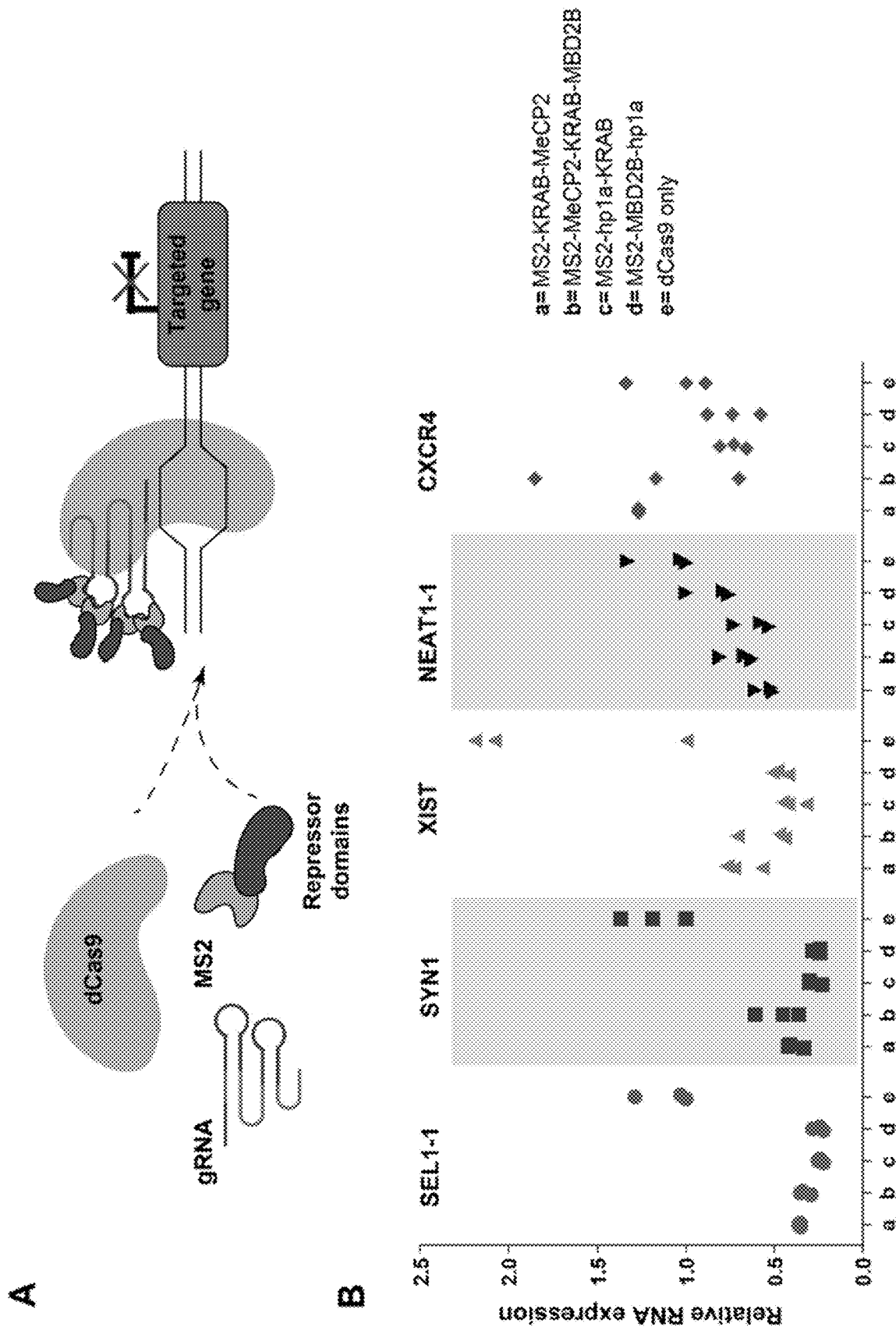
FIGS. 3A-3B show aptamer-mediated CRISPR repression in vitro.

The inventors previously reported enhanced CRISPR-based transcriptional repressors in vitro developed by direct fusion of a set of modulators to catalytically dead Cas9 protein (MeCP2, MBD2 or HP1a). The inventors first devised an experiment to determine the repression domains from our previously reported candidates that can lead to efficient transcriptional repression when fused to the MS2 coat protein (referred here to as MS2) and recruited to the CRISPR complex by gRNA aptamer binding (FIG. 3A). Quantitative real time polymerase chain reaction (qRT-PCR) analysis of a set of target genes in Human Embryonic Kidney 293 (HEK293FT) cells established that the MS2-HP1aKRAB [heterochromatin protein 1(HP1a)-Krüppel associated box (KRAB)] enabled efficient repression across the genes the inventors tested (FIG. 3B).

To translate these finding in vivo, the inventors set out to utilize nuclease competent Streptococcus Pyogenes (Sp)-Cas9 protein and truncated 14nt gRNAs for transcriptional repression of Myd88 in vivo. The inventors first examined MS2-HP1aKRAB-mediated repression of endogenous mouse Myd88 level in vitro and compared the efficiency with commonly used KRAB-based transcriptional repression. The inventors rationally designed two 14nt gRNAs that target within 100 bp upstream of the TATA box region in the endogenous mouse Myd88 locus or used a previously reported non-targeting mock gRNA as a control (FIG. 1A). qRT-PCR for Myd88 demonstrates the in vitro functionality of the gRNAs and superiority of MS2-HP1aKRAB in repression of endogenous Myd88 (FIG. 1B).

Figure 4:
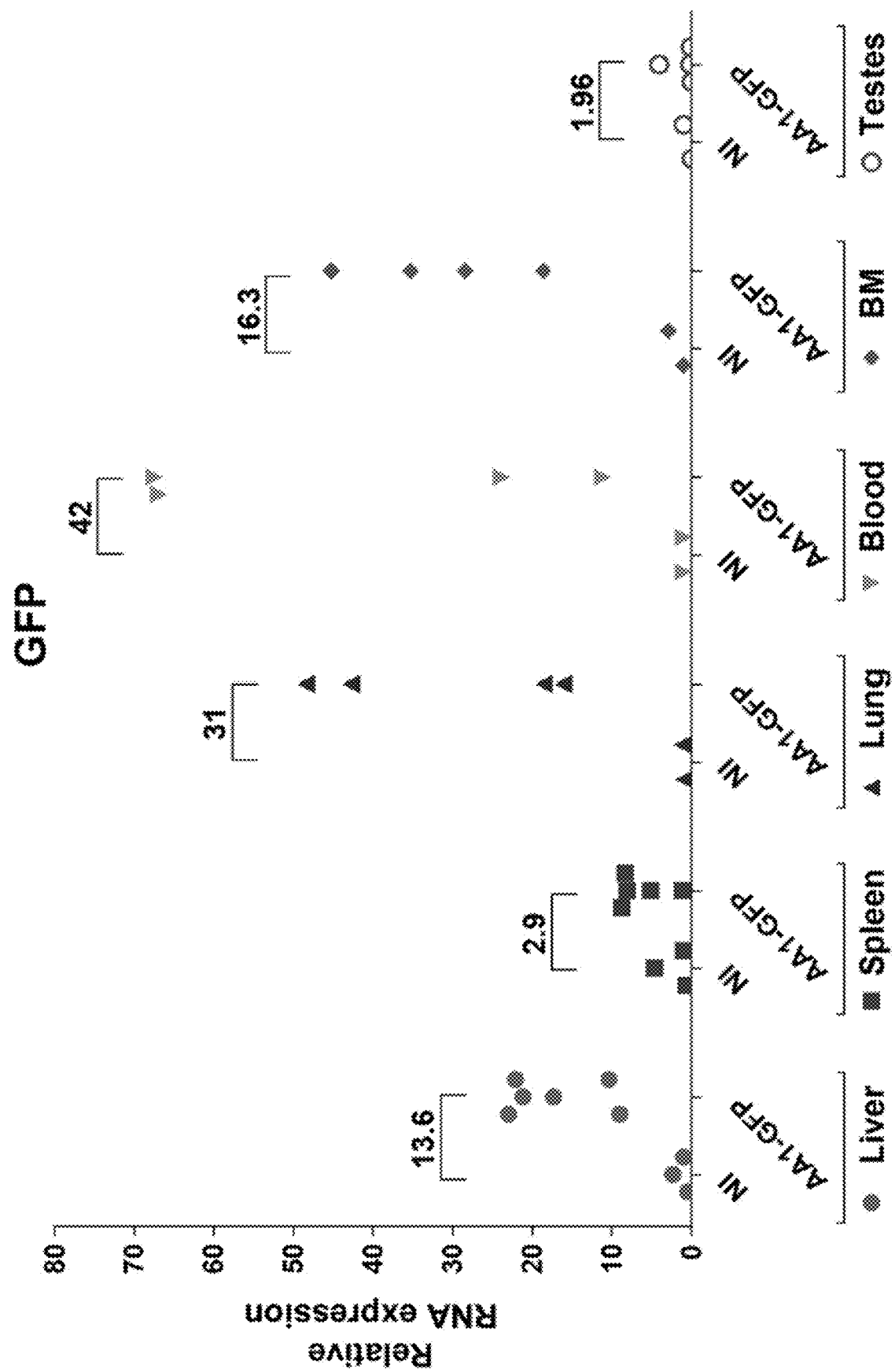
FIG. 4 shows in vivo analysis of AAV2/1 tropism towards different tissues. AAV2/1-GFP was delivered to C57BL/6 mice via retro-orbital injection. GFP expression was assessed in different tissues by qRT-PCR. Average fold change expression levels are indicated above each group and are quantified relative to not injected mice (N=3 for not injected group and N=4-6 for AAV-GFP group).

To test these repressors in vivo, the inventors pursued delivery through packaging gRNAs and MS2-repression cassettes within Adeno-Associated Virus (AAV) vectors. AAV serotypes have been used to deliver CRISPR in vivo, the most common serotype being AAV9, which has high affinity to numerous parenchymal cell populations. Here, the inventors employed AAV2/1, which is a recombinant AAV vector consisting of AAV2 inverted terminal repeats, and AAV1 Rep and Cap genes. AAV1 has been shown to be effective in transduction of components of the immune system and non-parenchymal cells such as dendritic cells, and endothelial cells. Moreover, AAV1 capsid can induce MyD88 signaling as part of the pathways of immunity against AAVs in the host. Our assessment of AAV2/1 tissue affinity revealed the highest expression in blood, lung and bone marrow (FIG. 4). Subsequently, the inventors performed systemic delivery of AAV/Myd88 gRNA or control AAV/Mock gRNA with MS2-HP1aKRAB or MS2-KRAB cassettes to Cas9 nuclease transgenic mice (FIG. 1C). To test whether CRISPR mediated transcriptional repression of Myd88 can create physiologically relevant effect on the immune response against AAV, the inventors specifically chose Cas9-expressing mice as they enable us to eliminate potential confounding effects associated with delivery of Cas9. Three weeks after injections, blood, lung, and bone marrow were harvested and Myd88 expression was assessed by qRT-PCR (FIG. 1D). Compared to uninjected controls, AAV vector delivery led to an increase in Myd88 across different tissues the inventors tested. Treatment with CRISPR to repress endogenous Myd88 with HP1aKRAB led to a significant reduction in the level of Myd88 in blood (~84%), lung (~75%) and bone marrow (~63%) as compared to the mock gRNA treated group, in agreement with high affinity of AAV2/1 for these tissues. Administration of the KRAB domain alone led to a less pronounced repression of Myd88 in lung (~52%), blood (~59%) and bone marrow (~34%), with slightly higher variation among the animals tested (FIG. 1D and Table 1).

TABLE 1

Repression levels of Myd88, Icam-1, and Tnfa were assessed by qRT-PCR in lung, blood, and bone marrow 3 weeks post retro-orbital injection of AAV. Gene expression fold-change was quantified relative to the universal control. The repression levels are reported as percentage of fold change of AAV-Myd88 group divided by the fold change of AAV-Mock group for each gene.

|  |  | Lung Mean of repression (%) ± STD | Blood Mean of repression (%) ± STD | Bone Marrow Mean of repression (%) ± STD |
|---|---|---|---|---|
| Myd88-HP1a-KRAB | Myd88 | 75% ± 0.389 | 84% ± 0.124 | 63% ± 0.227 |
|  | Icam-1 | 74% ± 0.1 | 88% ± 0.05 | 61% ± 0.24 |
|  | Tnfa | 63% ± 0.19 | 58% ± 0.09 | 57% ± 0.18 |
| Myd88-KRAB | Myd88 | 52% ± 0.7 | 59% ± 0.185 | 34% ± 0.276 |
|  | Icam-1 | NC ± 0.35 | 70% ± 0.29 | 41% ± 0.21 |
|  | Tnfa | 37% ± 0.46 | 45% ± 0.57 | 56% ± 0.19 |

NC = No Change

To assess the potency of repression in altering the downstream gene regulatory network, the inventors evaluated the levels of tumor necrosis factor-α (TNF-α) and intercellular adhesion molecule-1 (ICAM-1), two signaling elements directly modulated by the MyD88 signaling pathway. Myd88 targeting with MS2-HP1a-KRAB led to a significant reduction in Icam-1 and TNFα expression across multiple tissues, whereas targeting with MS2-KRAB did not lead to a similar consistent effect (FIGS. 1E-1F and Table 1).

Figures 5A, 5B, 5C:
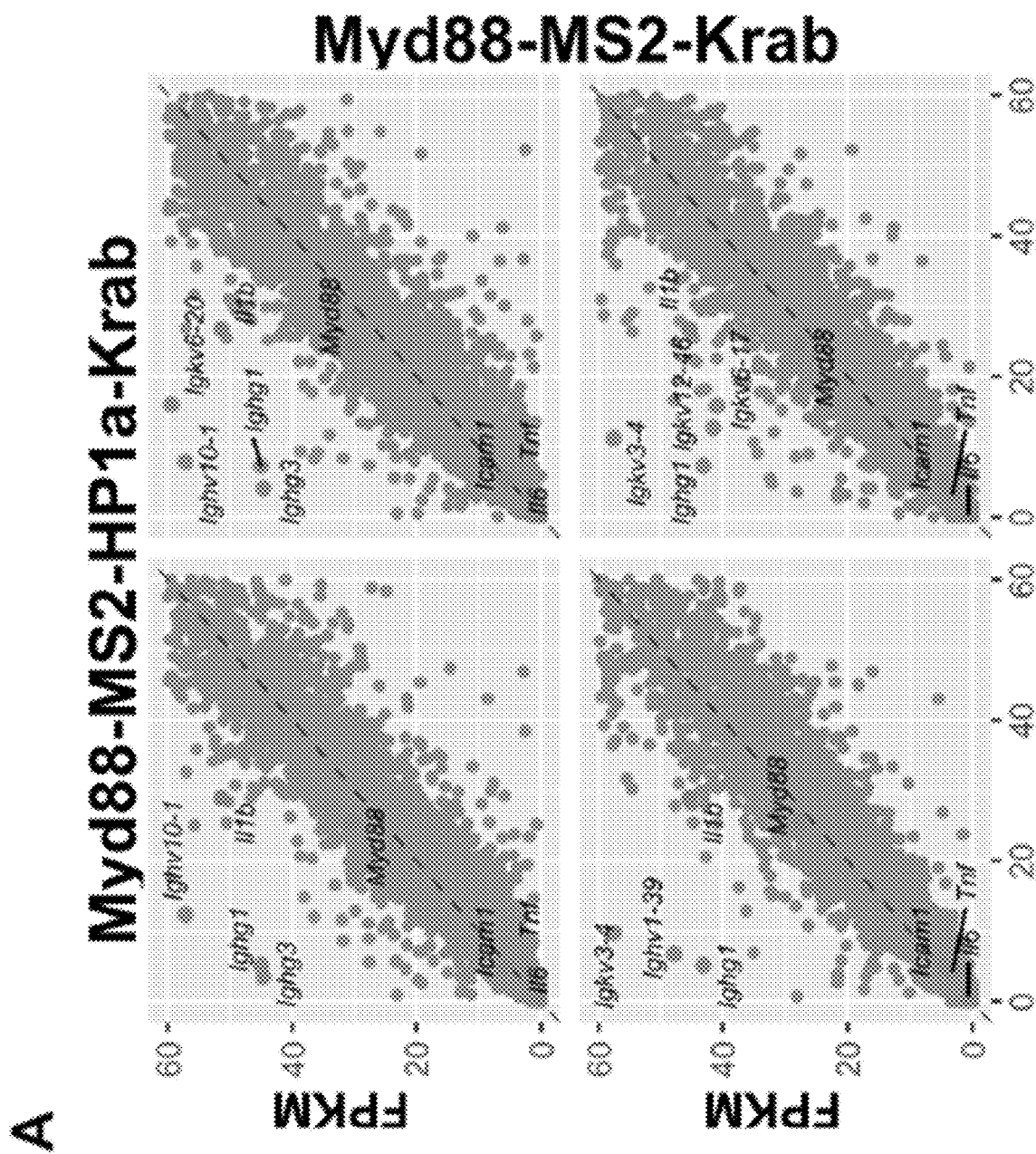
FIGS. 5A-5C show RNA-seq analyses of bone marrow samples collected from mice treated with AAV-Myd88-MS2-HP1aKrab versus AAV-Myd88-MS2-Krab.
Figures 5A, 5B, 5C:
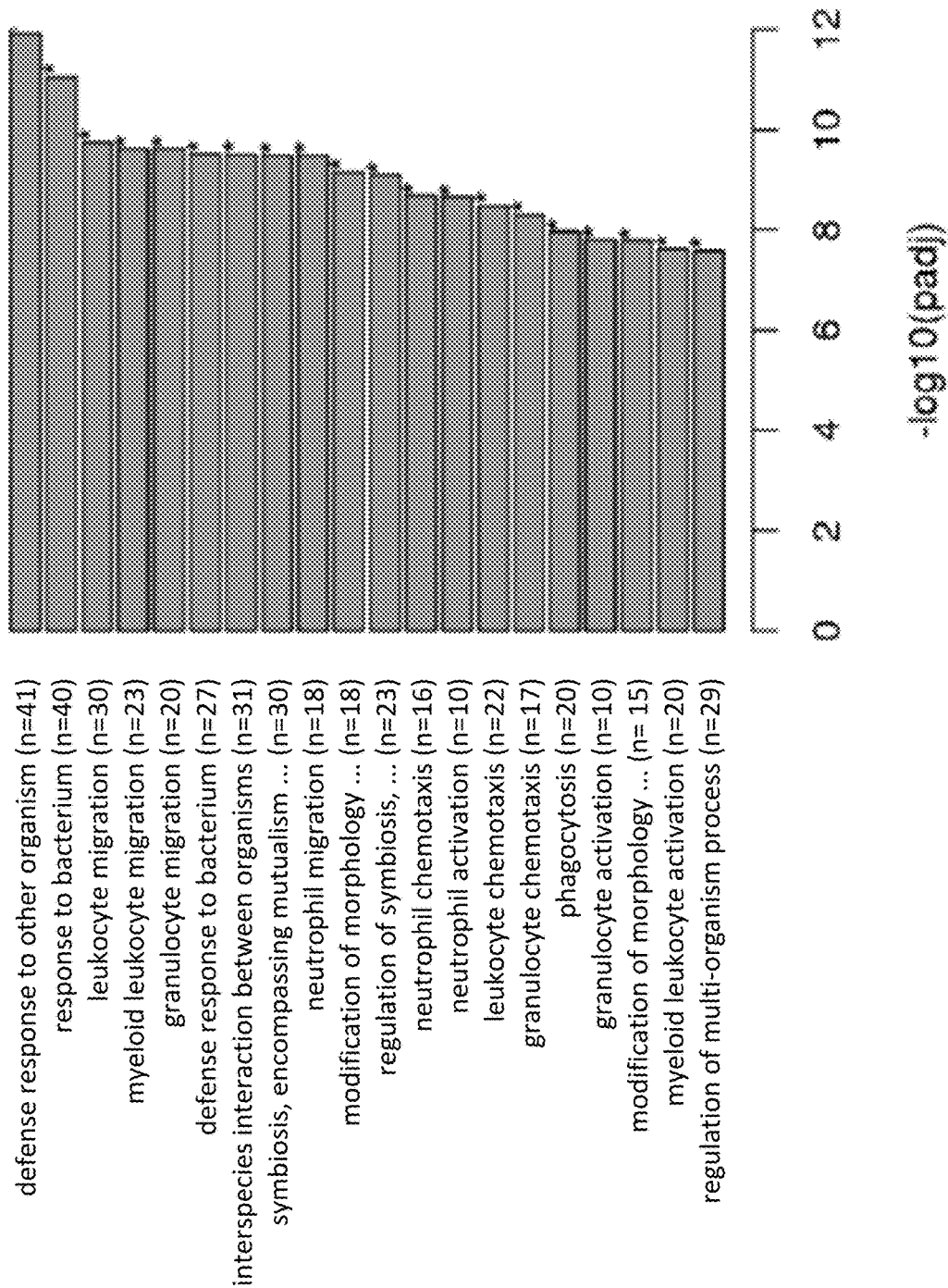
Figures 5A, 5B, 5C:
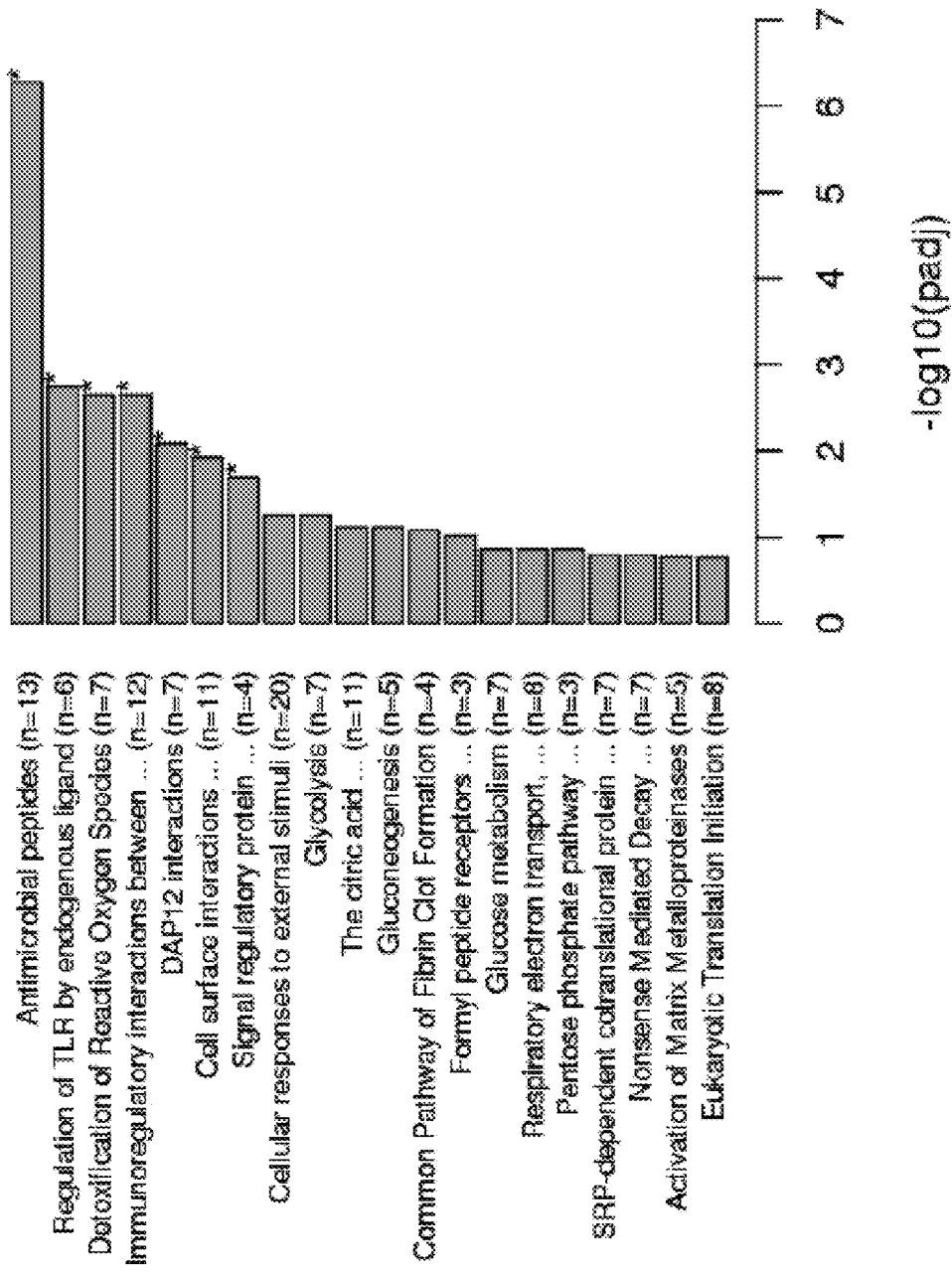
Figure 6:
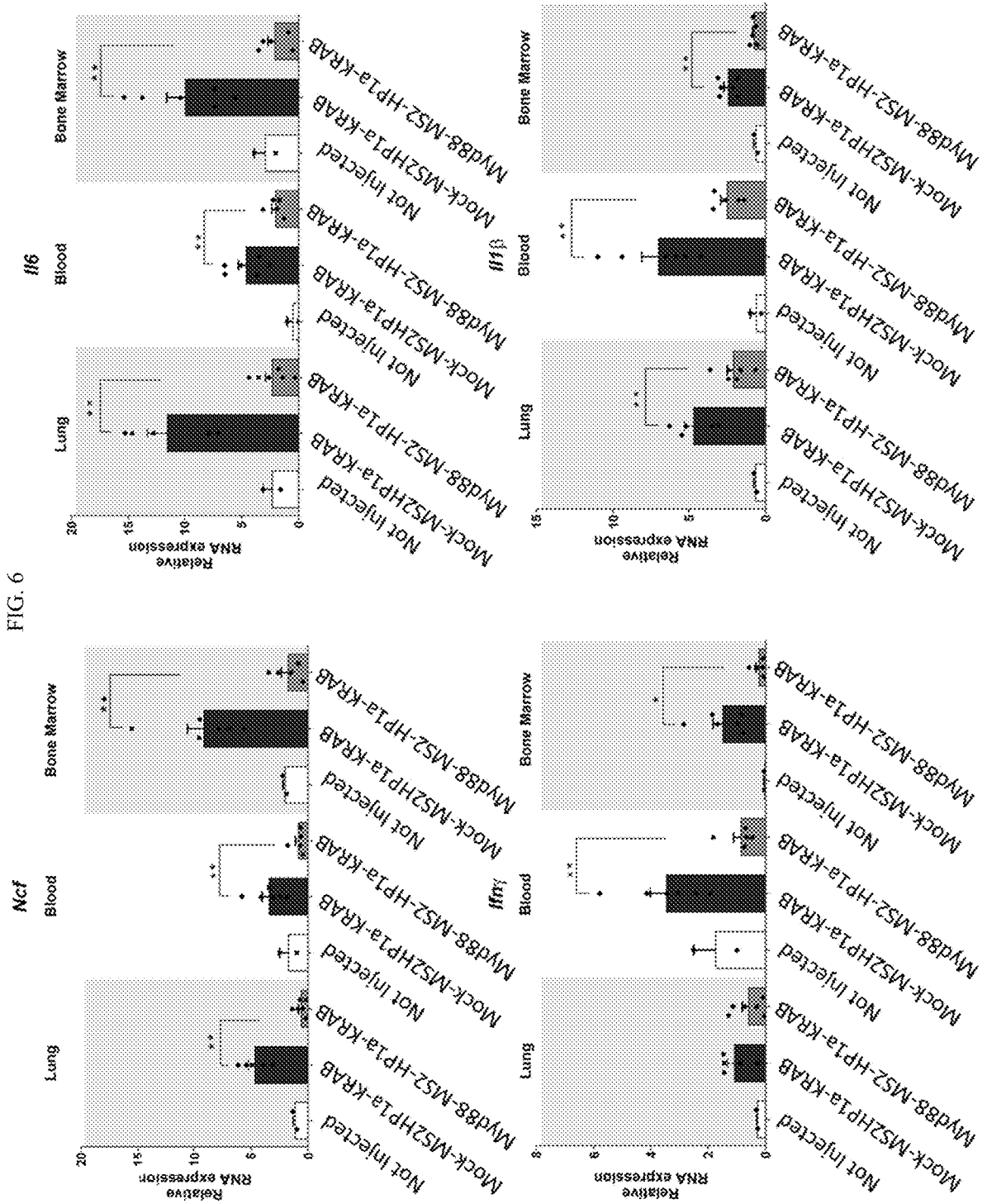
FIG. 6 shows analysis of a set of immune-related transcripts following LPS injury. qRT-PCR analysis of Ncf, Il6, Ifnγ, and Il1β mRNA expression in Lung, Blood, and Bone marrow quantified relative to the universal control following LPS injection (N=5-6 for injected groups and N=2 for Not Injected group). Universal control is the level of the desired transcript in a blood sample collected from a not injected Cas9 transgenic mouse. *P<0.05; significant
Figure 7:
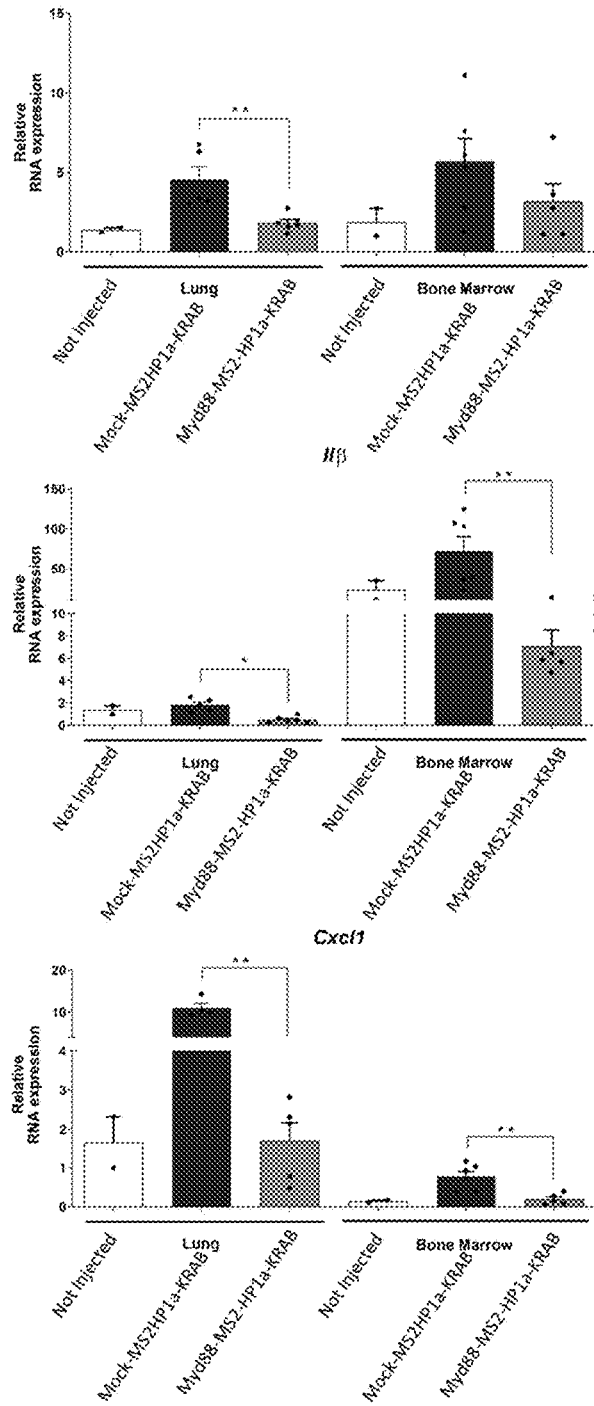
FIG. 7 shows an assessment of the level of a panel of immune related genes in lung and bone marrow following LPS injection. qRT-PCR analysis of in vivo CD68 (Marcrophage marker), Infα, Infβ, CD4, Cxcl1, and Stat4 relative to the universal control following LPS injection in lung and bone marrow. (N=5-6 for injected groups and N=2 for Not Injected group). "Universal control" is the level of the transcript of interest in a blood sample collected from a not injected Cas9 transgenic mouse. *P<0.05; significant
Figure 7:
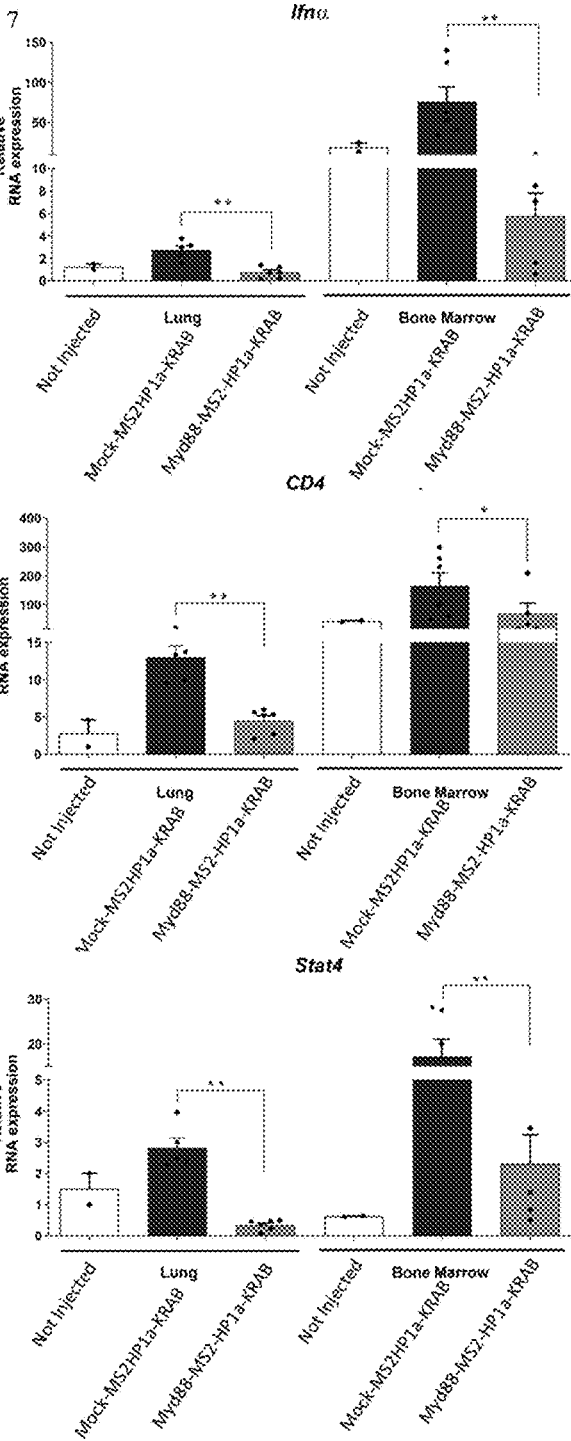

To perform a systemic assessment of the repression efficiency of MS2-HP1aKRAB system as compared to MS2-KRAB, the inventors performed next generation RNA sequencing on the bone marrow of mice treated with these constructs. MS2-HP1aKRAB treated mice expressed lower MyD88 levels compared to MS2-KRAB treated ones (FIG. 5A), which is accompanied with changes in downstream signaling pathways such as Il1β. Of note, GO Enrichment analysis revealed that Myd88-MS2-HP1aKRAB treated mice had significant downregulation of signaling pathways implicated in the immune and defense response against foreign organisms and bacteria, which are pathways associated with Myd88 function (FIG. 5B). Similarly, Reactome database revealed the TLR pathway as one of the highly significant pathways that are downregulated in the presence of MS2-HP1aKRAB (FIG. 5C). This evidence suggests that modulation of Myd88 and its downstream immune pathways is most effective with the MS2-HP1a KRAB repressor in vivo.

Interestingly, volcano plotting of differentially expressed genes revealed the constant region of heavy chain of immunoglobulin G1 and G2(Ighg1 and Ighg2b) and other immunoglobulin related heavy and light chain genes as most down-regulated with HP1a KRAB relative to KRAB (FIG. 1G).

Prior studies demonstrate that viral DNA stimulates TLR (i.e., TLR9), which in turn activates MyD88 and initiates downstream signaling events leading to adaptive immunity, and antibody production against AAVs. In light of prior evidence and the observed repression of the immunoglobulin pathway, the inventors asked whether there was a decrease in AAV-specific humoral response in Myd88 repressed groups. The inventors measured immunoglobulin G (IgG) response against AAV1 capsid. Compared to the un-injected controls, the inventors detected an 11-fold increase in plasma IgG2a levels against AAV1 in AAV/Mock treated animals. However, those who received AAV/Myd88 had significantly lower (60%) plasma IgG2a against AAV-1 (FIG. 1H). This finding presents an exciting opportunity to modulate humoral immunity against AAV, a significant challenge in current AAV-based gene therapies, with a tool inherently suited to perform concurrent gene editing (nuclease competent CRISPR).

Having identified a more potent CRISPR repressor for transcriptional modulation of MyD88, the inventors next asked whether this repression is sufficient to modulate downstream host response and confer protection when there is an augmented systemic transcriptional response, such as in septicemia. Septicemia is a pressing medical issue due to the emergence of antibiotic-resistance and rising longevity of patients suffering from chronic diseases. Moreover, high mortality rate due to septicemia still remains a medical challenge following trauma in the battlefield, highlighting the need for novel prevention strategies.

Figure 2:
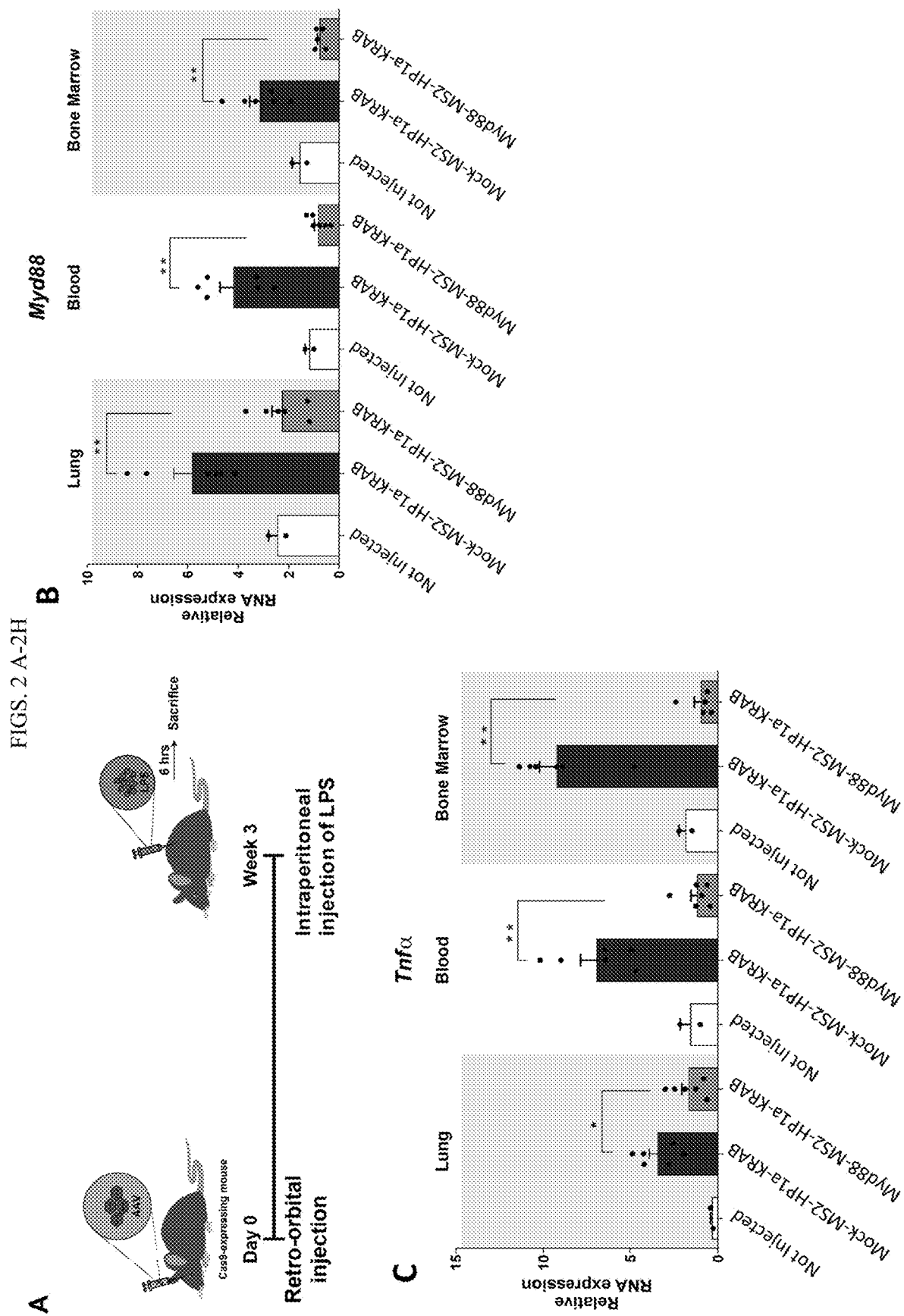
FIGS. 2A-2H show CRISPR-based modulation of host inflammatory response confers protection following LPS-mediated septicemia.
Figures 2A, 2B, 2C, 2D, 2E, 2F, 2G, 2H:
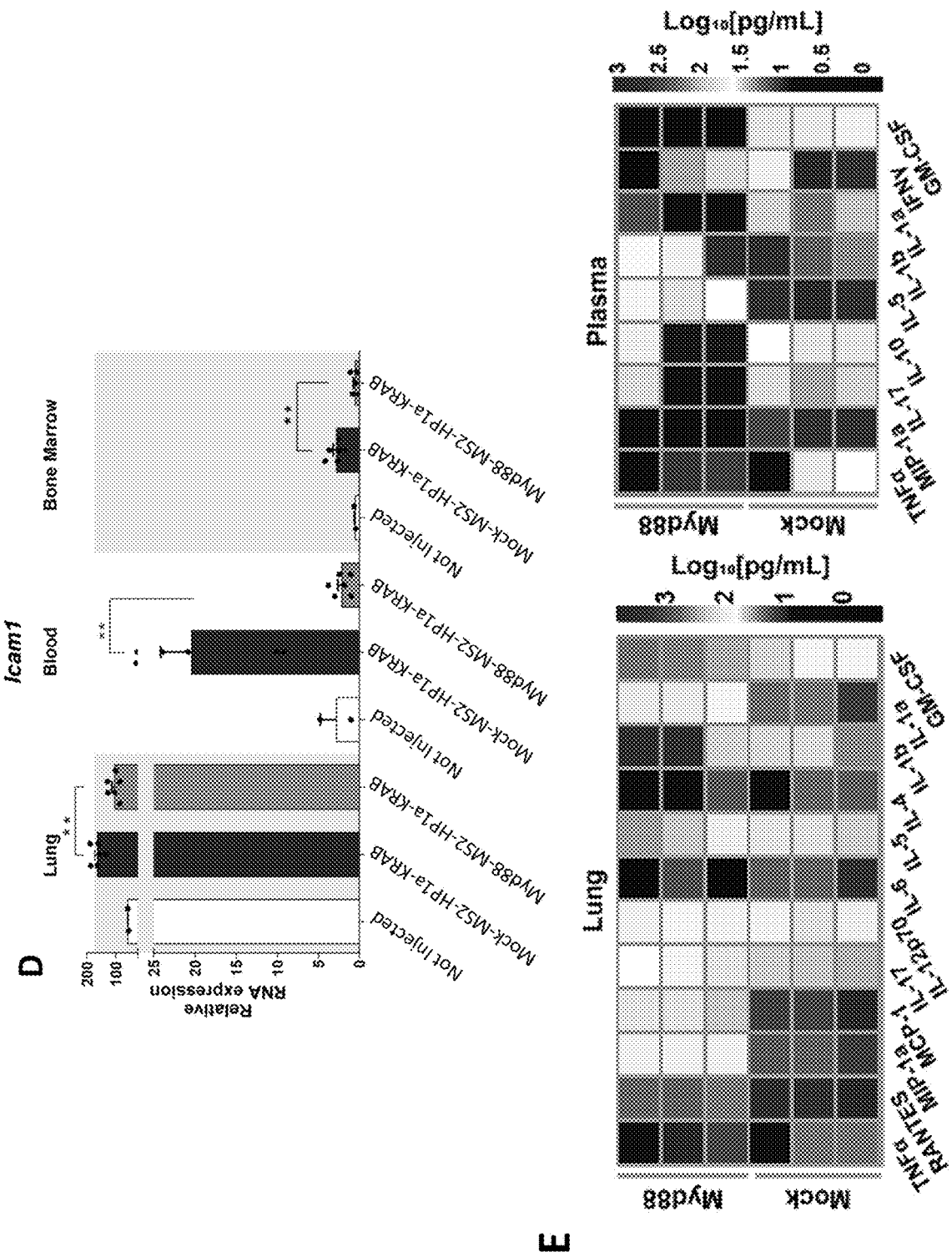
Figures 2A, 2B, 2C, 2D, 2E, 2F, 2G, 2H:
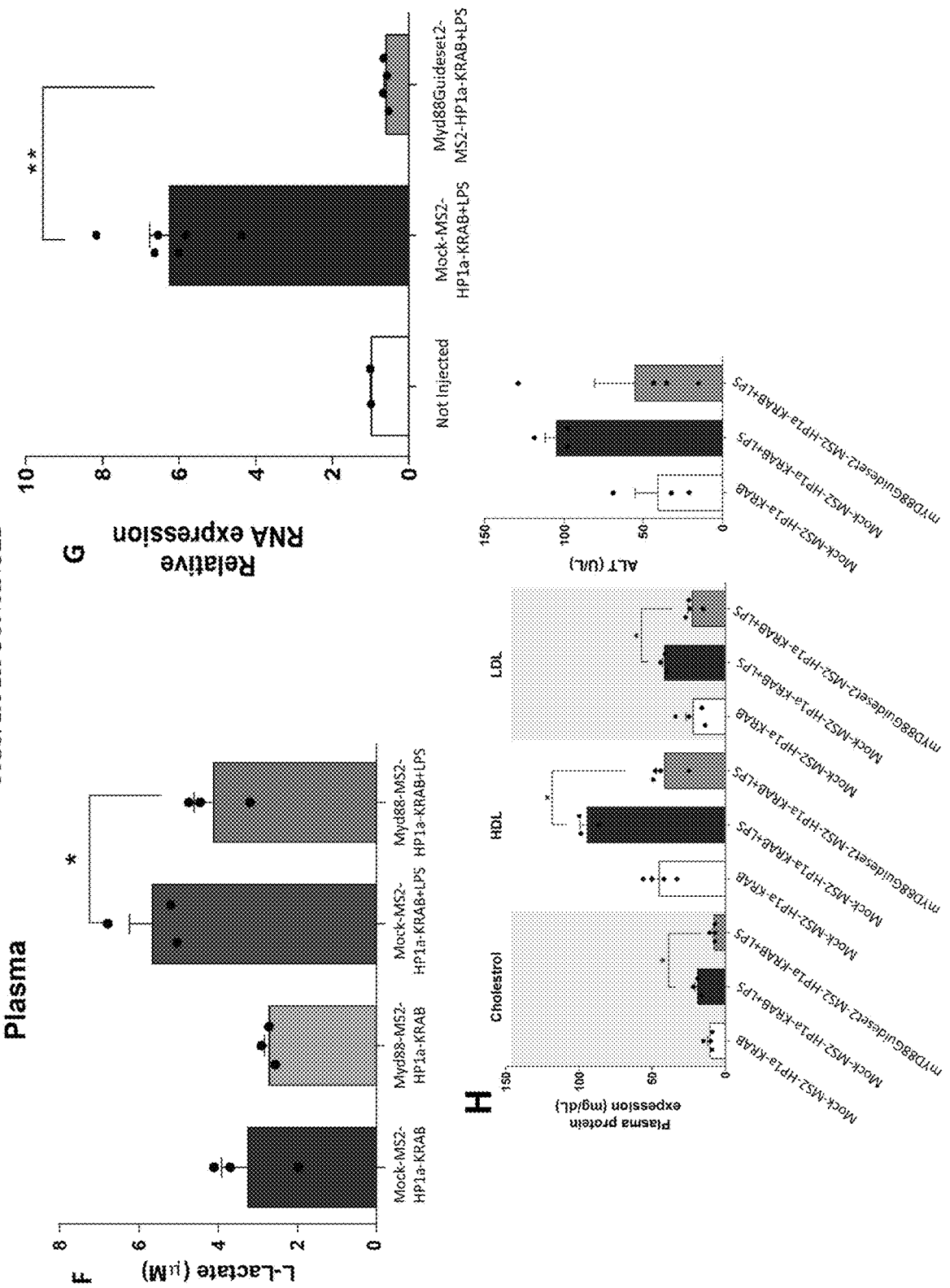

The inventors pre-treated Cas9 mice with AAV/Myd88-Ms2-HP1aKRAB or AAV/Mock and three weeks later subjected them to systemic lipopolysaccharides (LPS) (from *Escherichia coli* 0127:B8) treatment. Six hours following LPS treatment, the inventors harvested lung, blood and bone marrow and assessed the transcript levels of Myd88 and major inflammatory cytokines (FIG. 2A). The inventors observed significant repression of Myd88 in lung (61%), blood (80%) and bone marrow (76%) compared to AAV/Mock-treated mice (FIG. 2B). In response to LPS, Myd88 repression prevented upregulation of a wide range of inflammatory and immune-related markers that are directly or indirectly downstream of Myd88 signaling such as Icam-1, Tnfα, Ncf, and I16, Ifn-α, Ifn-β, Ifn-γ, and Stat4 (FIGS. 2C-2D, FIG. 6, and FIG. 7). Analysis of serum and lung cytokine levels using a quantitative ELISA-based chemiluminescent assay revealed lower level of cytokines in Myd88-repressed mice (FIG. 2E). Additionally, serum lactate level, a systemic marker associated with septicemia and tissue damage, was significantly lower when mice were pretreated with the AAV/Myd88 repression cassette before LPS exposure, indicating a reduced systemic injury (FIG. 2F).

Figures 8A, 8B, 8C:
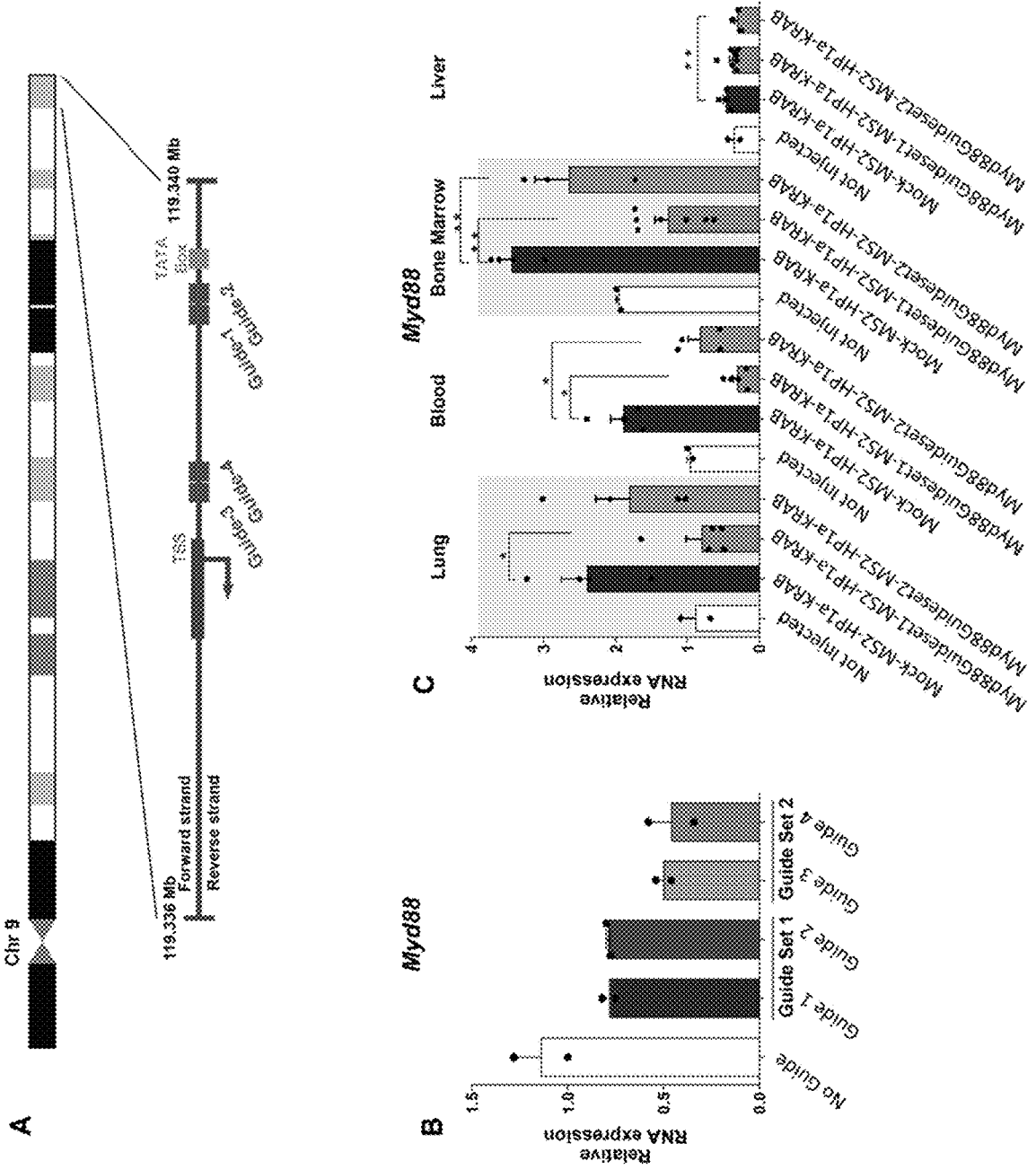
FIGS. 8A-8C show an assessment of the repression efficiency of a set of gRNAs targeting a different region of Myd88 locus.
Figure 9:
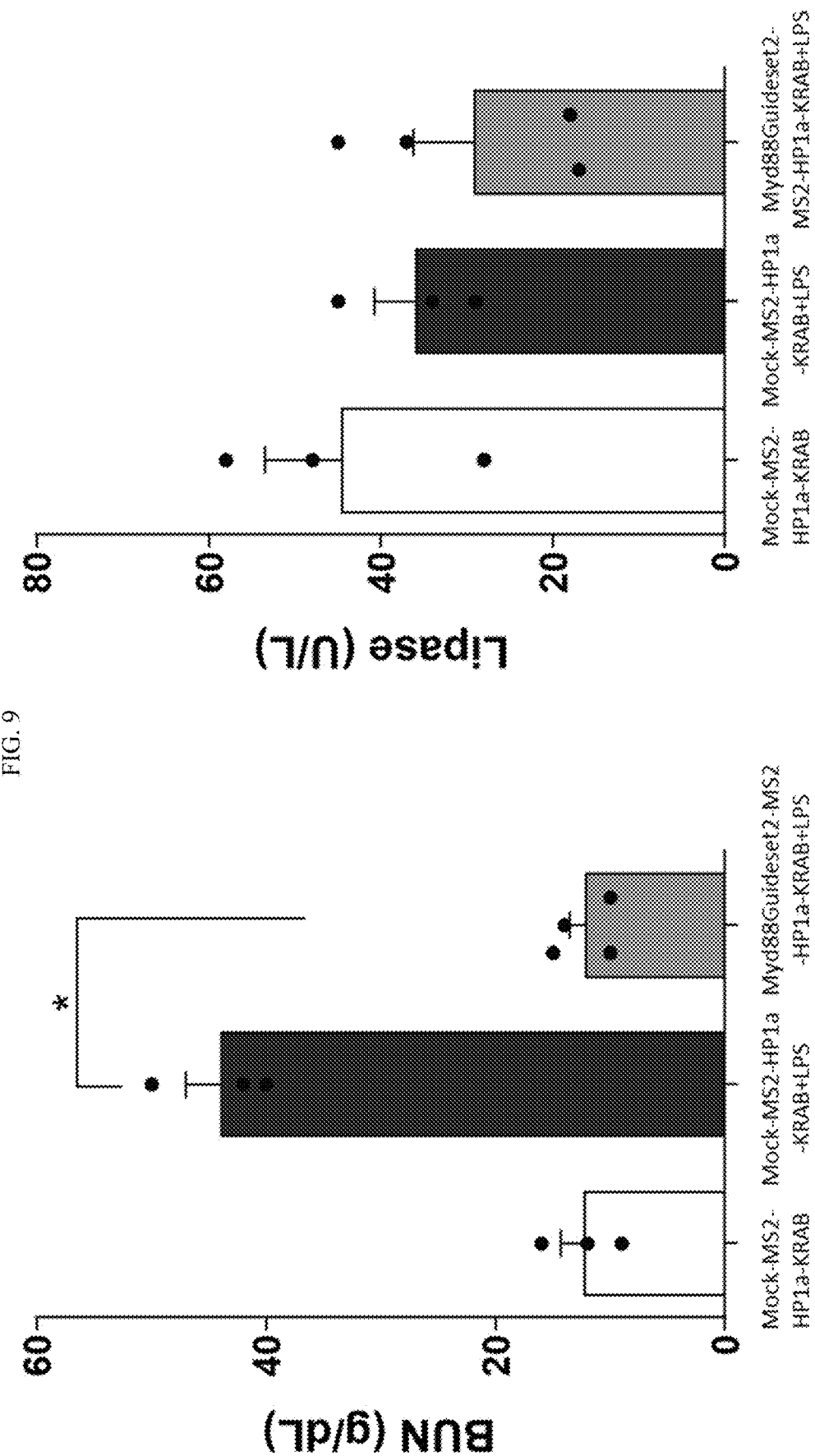
FIG. 9 shows analysis of serum markers of tissue damage following LPS injury. Serum Blood Urea Nitrogen (BUN), a marker of injury to kidney, was increased in serum after LPS injury, and Myd88 repression prevented such increase. LPS treatment and Myd88 repression did not have any significant effect on serum Lipase level, which generally indicates injury to the pancreas. *P<0.05; significant
Figures 10A, 10B, 10C:
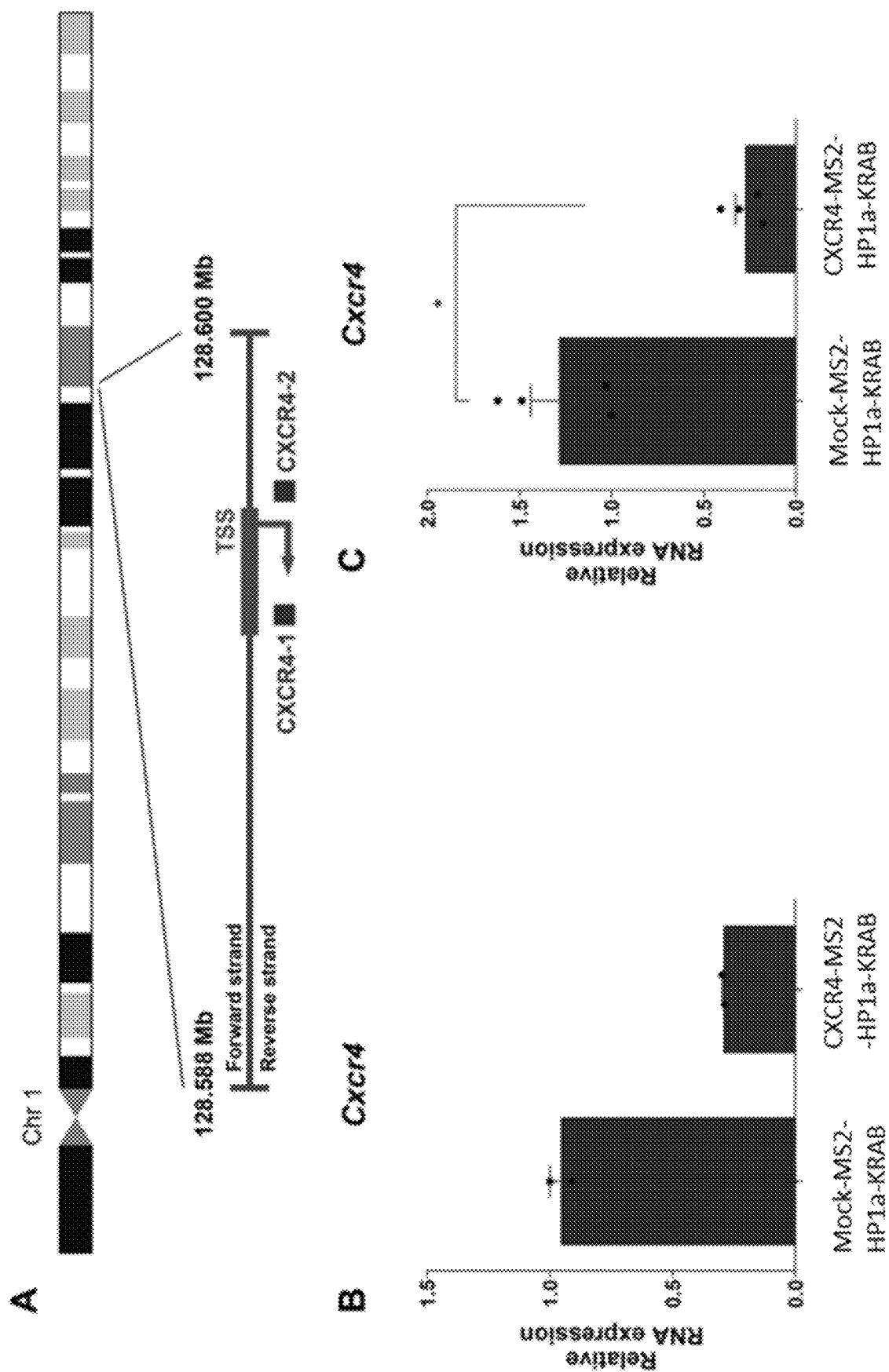
FIGS. 10A-10C show endogenous repression of Cxcr4.
Figure 11:
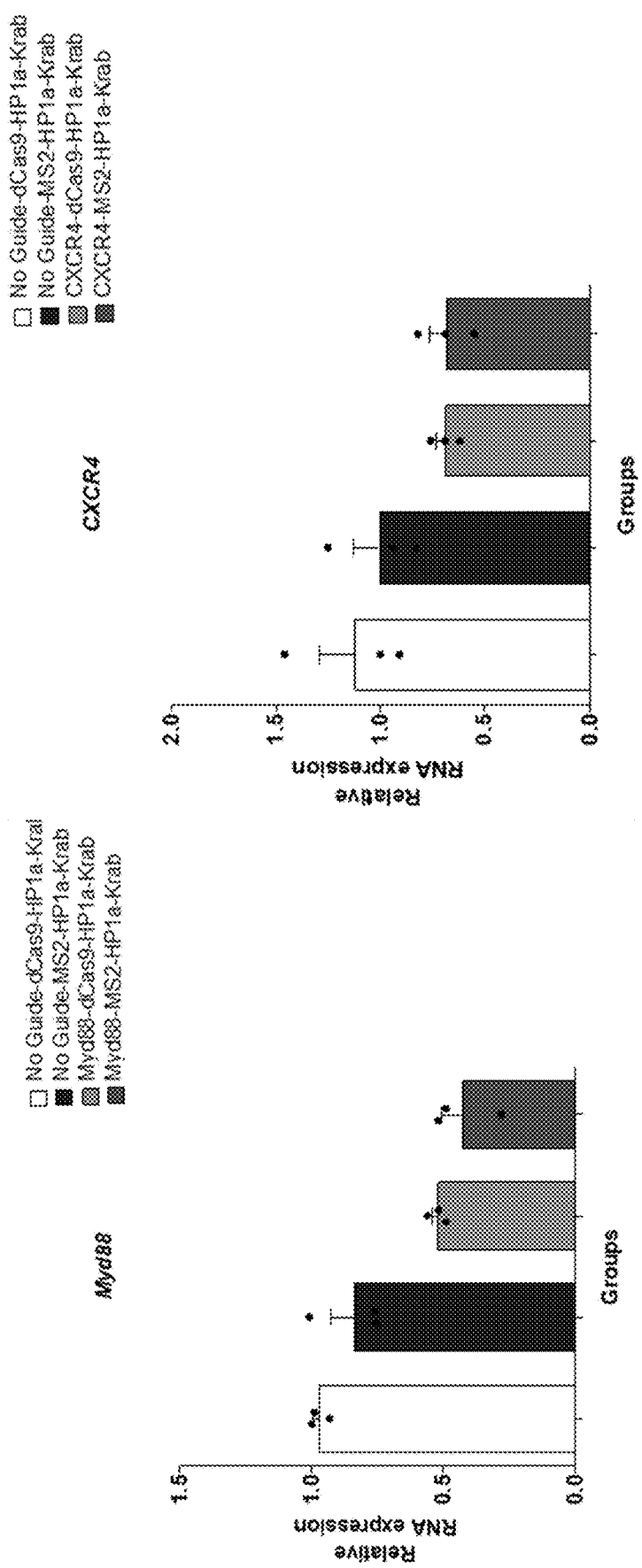
FIG. 11 shows the differences between MS2-HP1aKRAB and Cas9-HP1 aKRAB. Data shows similar level of repression using Cas9 plus MS2 fused Hp1a-Krab repressor and Cas9 fused to HP1a-Krab.
Figure 12:
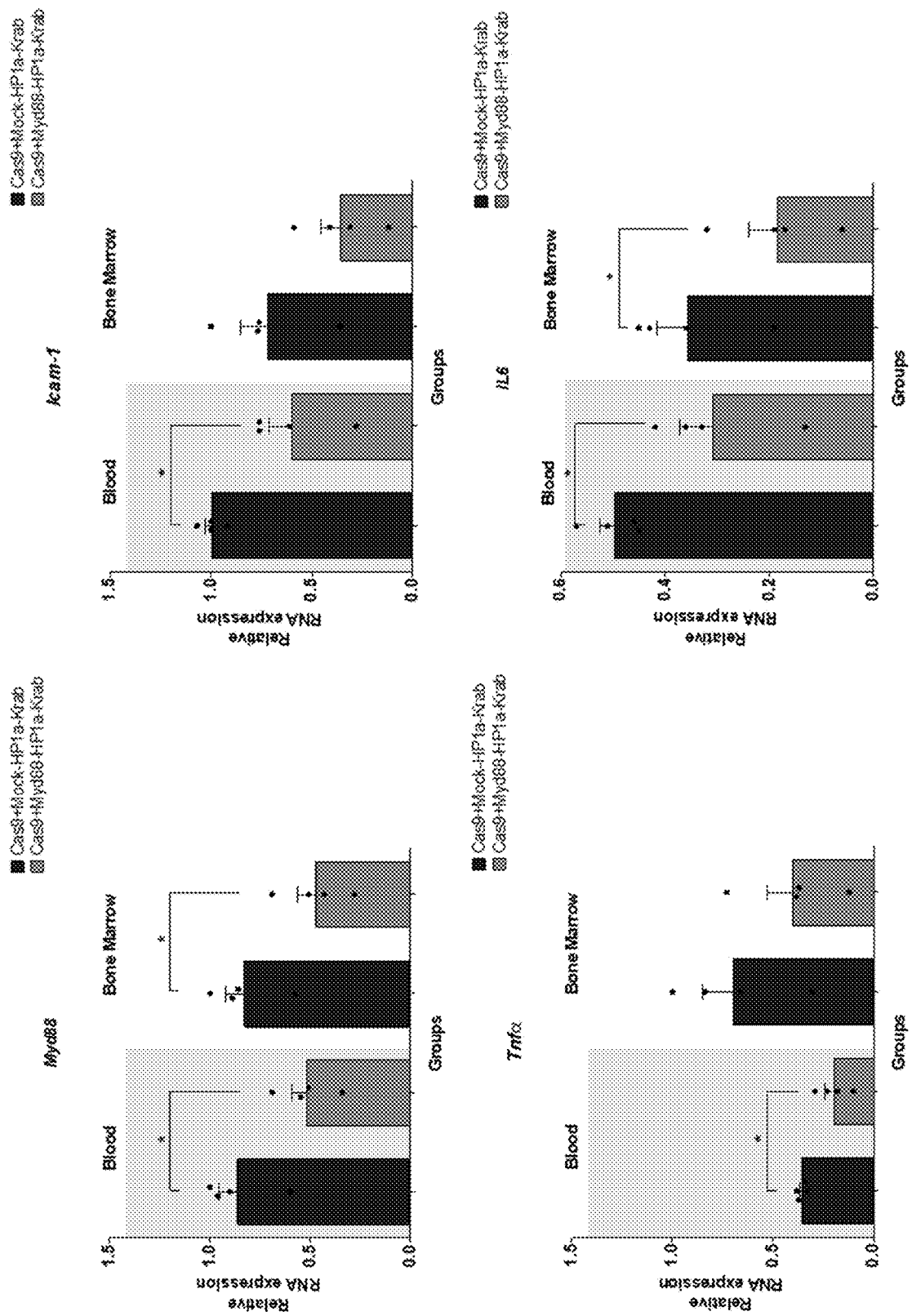
FIG. 12 shows repression of Myd88 and downstream cytokines followed by CRISPR delivery to wild type mice.
Figure 13:
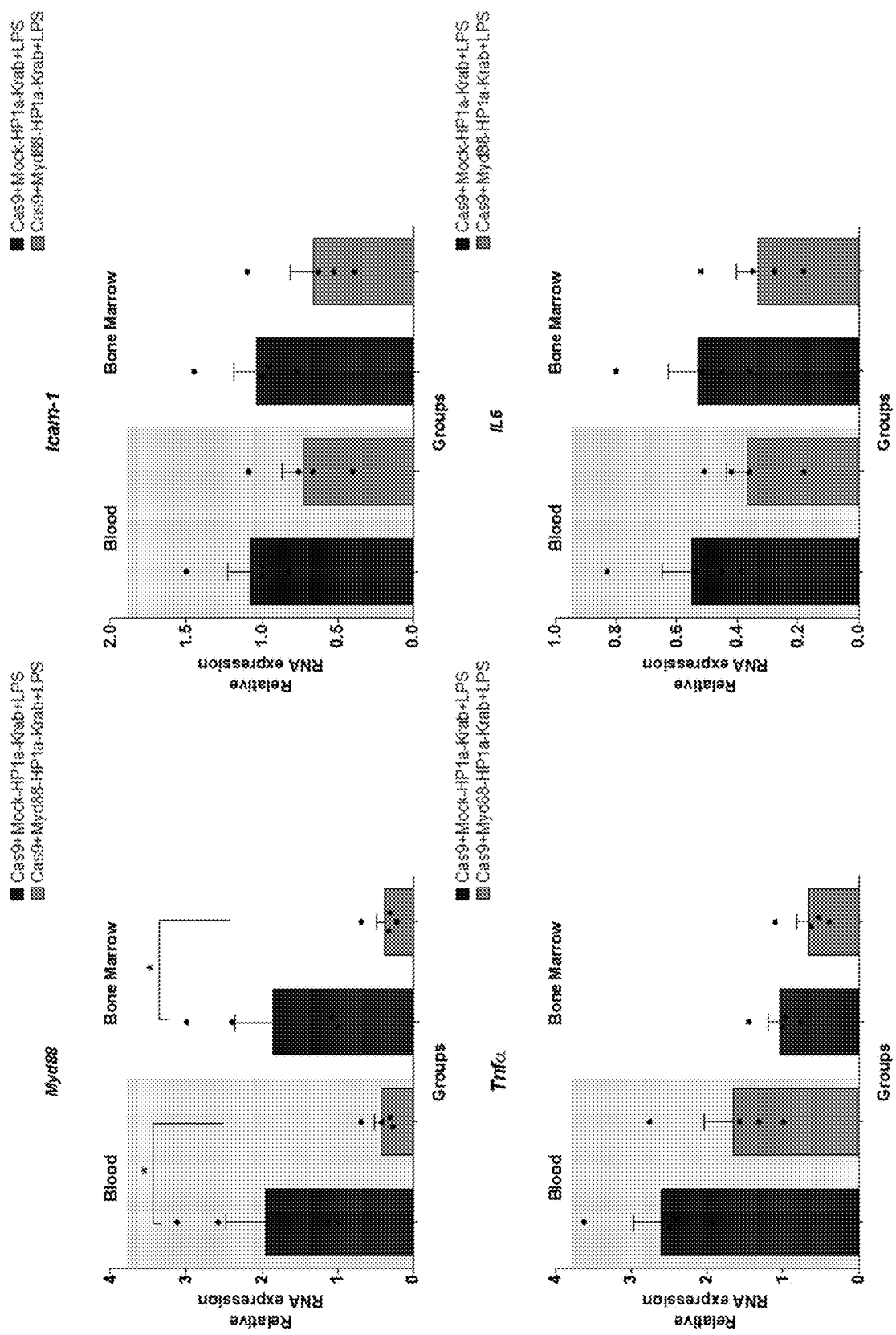
FIG. 13 shows repression of Myd88 and downstream cytokines followed by CRISPR delivery to wild type mice injected with LPS.
Figure 14:
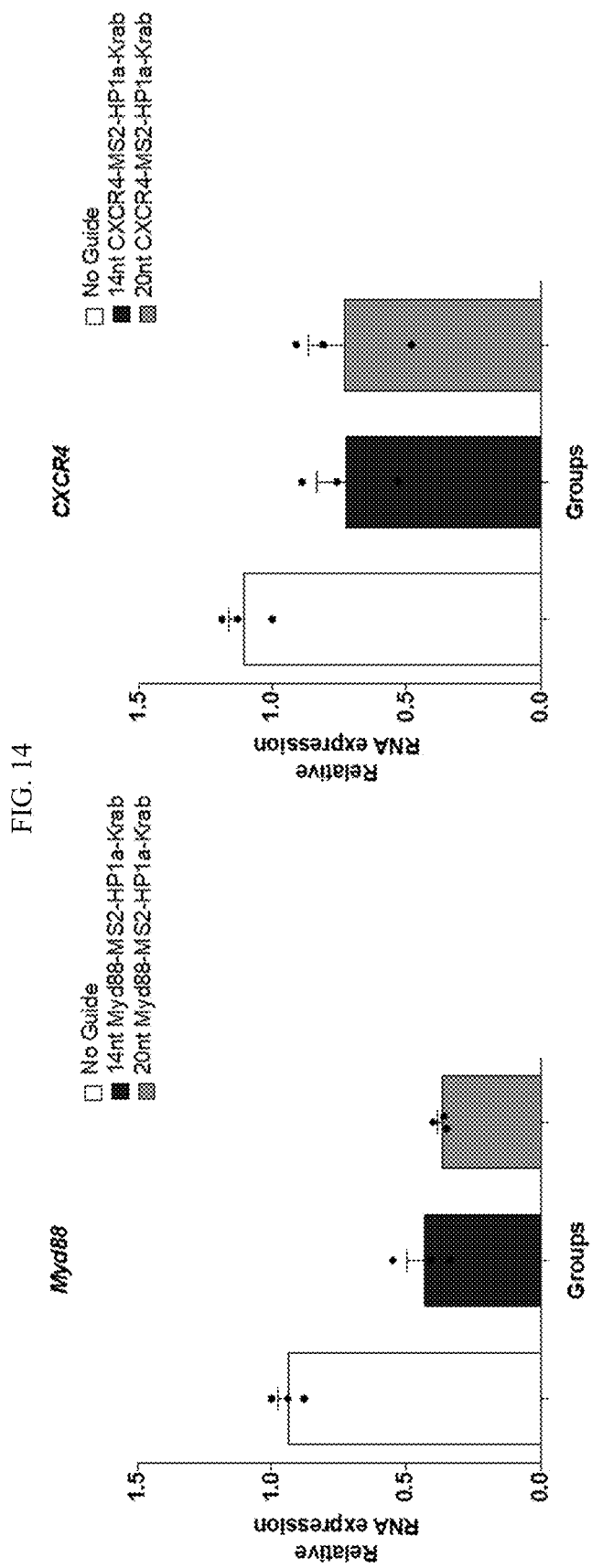
FIG. 14 shows a comparison of the repression efficiency of Cas9 with 14nt versus 20nt gRNA guide sequences targeting different loci. Data shows similar level of repression using Cas9+MS2-Hp1a-Krab repressor in combination with 14 nt gRNA or 20ntgRNA.
Figure 15:
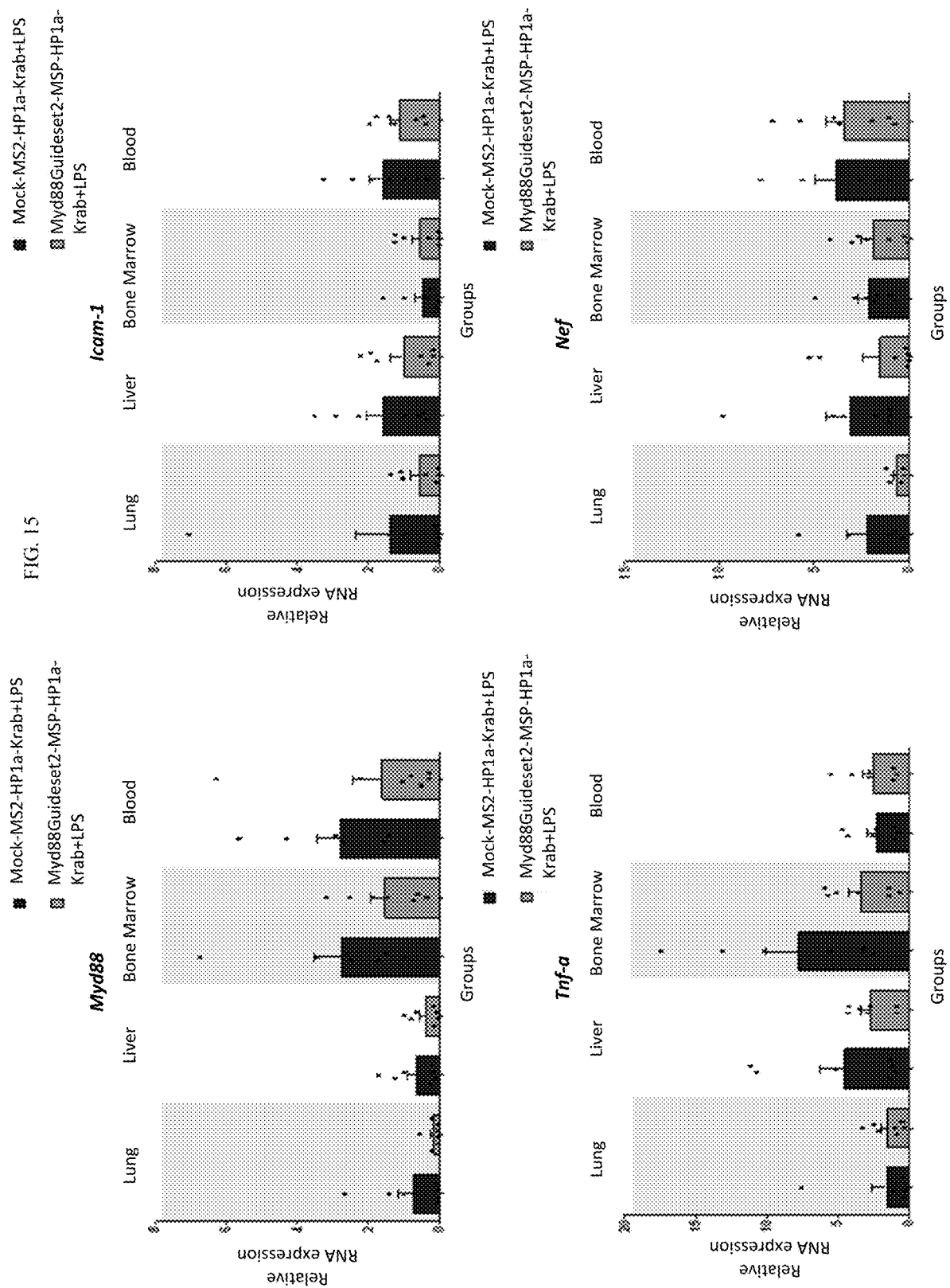
FIG. 15 shows qRT-PCR analysis of in vivo Myd88 expression 24 hours post CRISPR delivery. Mice received 2.5 mg/kg LPS. Two hours post LPS injection mice received the CRISPR synthetic repression system using pepjet. qRT-PCR analysis of Myd88 expression shows decreased level of Myd88 in lung, liver, and bone marrow.
Figure 15:
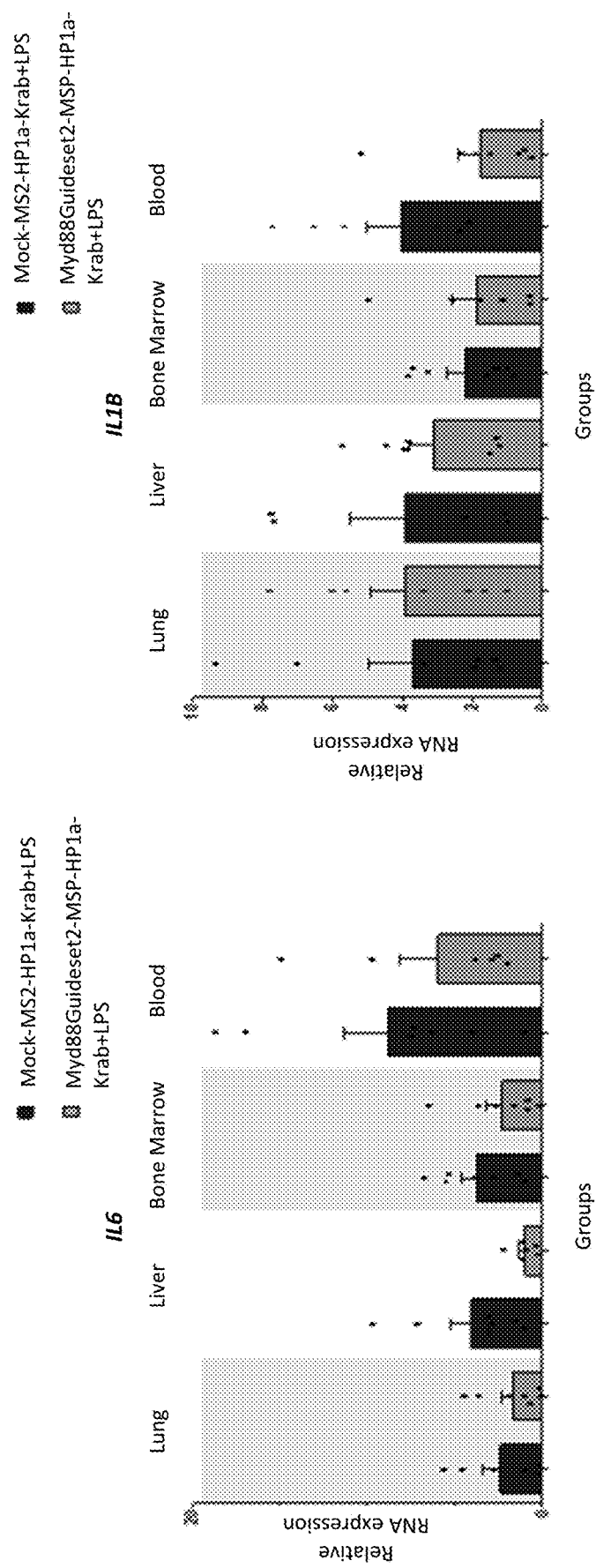
Figure 16:
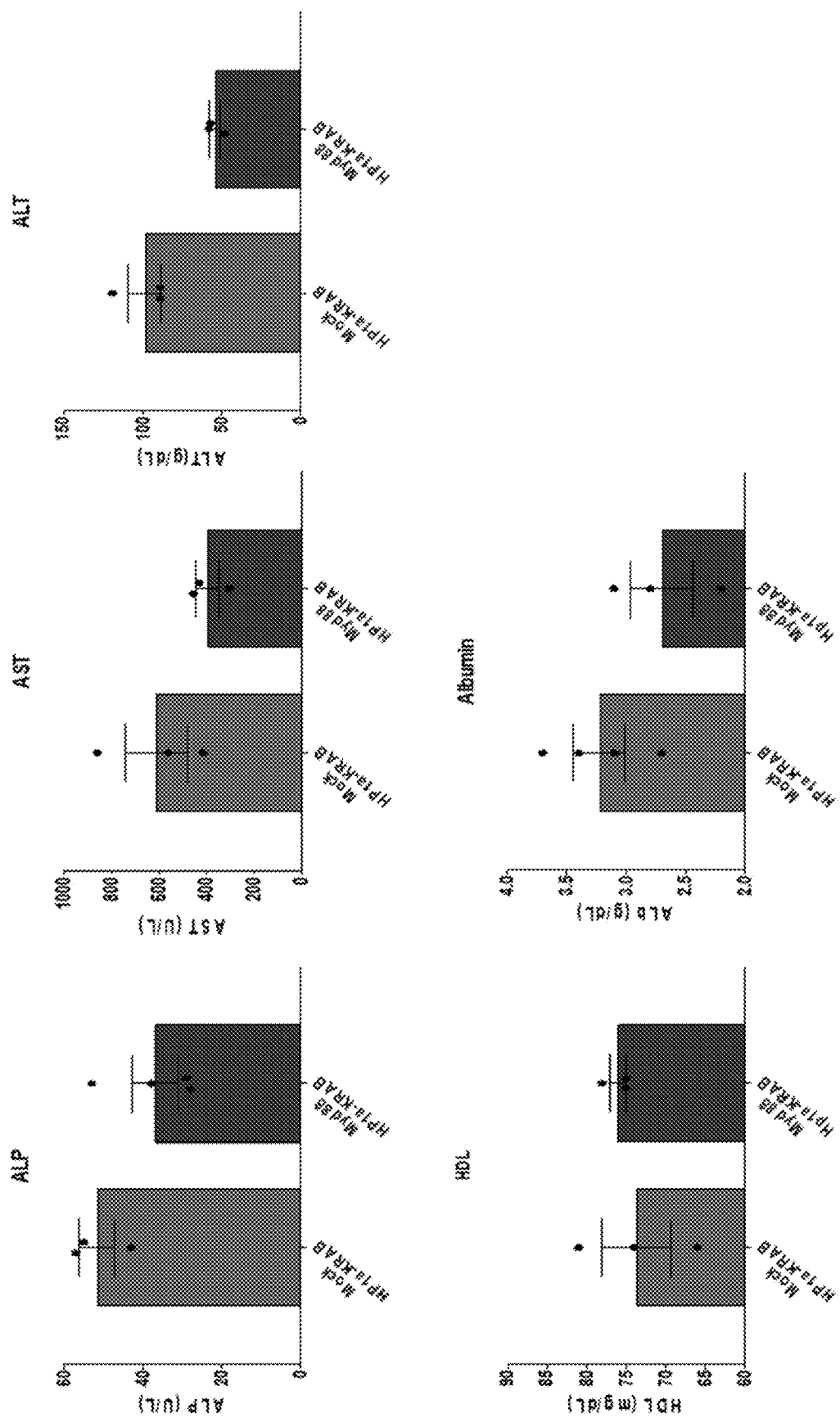
FIG. 16 shows IDEXX liver panel data. Mice received 2.5 mg/kg LPS. Two hours post LPS injection mice received the CRISPR synthetic repression system using pepjet.

Next, the inventors explored Myd88 repression levels through targeting a different region of the Myd88 promoter. The inventors constructed gRNAs targeting within 100 bp upstream of the transcription start site (Set 2) and detected superior in vitro efficacy compared to the previous set of gRNAs (Set 1) (FIGS. 8A-8B). Strikingly, the new Myd88 gRNAs led to superior repression in the liver and significant but less pronounced repression of Myd88 in blood, lung and bone marrow when compared to previous set of gRNAs (FIG. 8C). This was also observed following LPS injury (FIG. 2G), demonstrating a potential organ and cell type-specific effect of gRNA target site within the endogenous promoters. Next, the inventors asked if this CRISPR-based MyD88 repression is sufficient to induce a patho-physiologically relevant phenotype after LPS-induced damage. Analysis of serum markers of systemic inflammatory response and tissue damage of the liver showed that pretreatment with CRISPR-Set 2 attenuates the detrimental effects of LPS injection (FIG. 2H). In particular, high density lipoprotein (HDL) has been shown to increase following LPS treatment to eliminate systemic LPS to protect tissues from damage and has been associated with MyD88 signaling. In accordance with this, the inventors found that LPS induced an elevation in HDL, low density lipoproteins (LDL), and cholesterol in mock-treated groups but not under MyD88 repression. In addition, MyD88 repression suppressed the elevation in Alanine Transaminase (ALT), a marker of hepatocyte damage, and Blood Urea Nitrogen (BUN), a marker of acute kidney injury, which further suggests that Myd88 repression could ameliorate liver and systemic tissue damage following septicemia (FIG. 2H and FIG. 9). Finally, the inventors showed the extensibility of MS2-HP1aKRAB super-repression for synthetic control of other immunologically relevant loci such as CXCR4 in vitro and in vivo (FIGS. 10A-10C).

In summary, the inventors provide compositions, systems, and methods for synthetic control of immune response in vivo using a newly developed CRISPR-based transcriptional super-repressor against endogenous Myd88. The inventors show that this system is effective in modulating layers of downstream signaling and can create a visible protective phenotype in vivo. This notion is especially attractive in case of delivery using a less common AAV serotype (AAV2/1) known to target smaller cellular populations in vivo (e.g. non-parenchymal cells).

The inventors demonstrate that targeting the Myd88 locus with AAV/CRISPR generated less IgG2a against AAV1 and modulated general immunoglobulin expression patterns, consistent with prior reports on failure of generation of antigen specific IgG2a response in Myd88−/− animals. Additionally, AAV-1 was shown to be able to target dendritic cells, and Myd88 signaling in these cells was important to mount adaptive immune response against AAVs. The ability to control Myd88 levels using a CRISPR-based synthetic repressor is of significance in light of the common challenges involved with AAV-based clinical gene therapies, as this pathway has been demonstrated as a key node to induce humoral immunity against many AAV serotypes and not just AAV2/1 in vivo. Employment of a nuclease competent Cas9 and a truncated gRNA in this study opens up an opportunity for simultaneous application of CRISPR for targeted gene editing while modulating the immune response, which makes CRISPR-mediated gene repression superior to previously used systems such as shRNAs.

This strategy was also effective in modulating systemic inflammatory response against (LPS)-induced endotoxemia. CRISPR-mediated endogenous repression of Myd88 prevented upregulation of a wide range of inflammatory markers and conferred a protective phenotype. This notion is promising for the application of CRISPR-based transcriptional regulation as a readily programmable tool for modulating inflammatory conditions and protecting against septicemia. Finally, activating somatic mutation in Myd88 (L265P) is implicated in Waldenström macroglobulinemia, a type of non-Hodgkin lymphoma characterized by unchecked lymphocyte proliferation and macroglobulin production. Myd88 mutation supports malignant growth through NF-κB signaling and its inhibition is associated with decreased survival of cancer cells. The ability to systemically repress Myd88 (and CXCR4) as shown in this study, can therefore present an exciting therapeutic opportunity for this group of patients.

Methods

MS2 Fusion repressors—To construct the MS2 fused transcriptional repressors, the specific domains of interest were amplified from vectors previously published in our group and subsequently cloned into pcDNA3-MS2-VP64 backbone (Addgene plasmid ID: 79371)[10]. The pcDNA3-MS2-VP64 vector was digested with NotI and AgeI to remove the VP64 domain and then the amplified repressors were cloned into this backbone via Gibson Assembly method.

U6-gRNA-MS2 plasmids—To generate these plasmids, 14 bp or 20 bp spacers of gRNAs were inserted into sgRNA-MS2 cloning backbone (Addgene plasmid ID: 61424) at BbsI site via golden gate reaction. All the gRNA sequences are listed below.

AAV vectors—Following cloning of the gRNAs into a U6-sgRNA-MS2 backbone, the U6-gRNA encoding region was amplified from this vector and inserted within gateway entry vectors using golden gate reaction. Using the same method, the repressor domain and a shef1a promoter were cloned into gateway entry vectors. The designed safety switch sgRNA sequence was synthesized as gblocks (Integrated DNA Technologies) and inserted into a gateway entry vector (Addgene plasmid ID #62084) digested with HindIII and SphI. Further sub-cloning of all these components into AAV backbone via LR reaction (Invitrogen) made the AAV vectors. All the primers and gRNA sequences are listed below.

AAV packaging and purification—Constructed AAV vectors were digested by SmaI digest to test the integrity of ITR regions before virus production. Verified AAV vectors were used to generate AAV2/1-Myd88, AAV2/1-CXCR4, AAV2/DJ-TTN, AAV2/DJ-Cas9, and AAV2/1-Cas9 by PackGene® Biotech, LLC. The virus titers were quantified via Real-time SYBR Green PCR at 1.5E+13 GC/ml against standard curves using linearized parental AAV vectors.

AVV2/1-Myd88

(SEQ ID NO: 64)

```
CCTGCAGGCAGCTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGGGTTCCTGCGGCC

GCACGCGTTGATATCAACTTTGTATAGAAAAGTTTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CTGCGGGTCCTGCACTGTTTTAGAGCTAGGCCAACATGAGGATCACCCATGTCTGCAGGGCCTAGCAA

GTTAAAATAAGGCTAGTCCGTTATCAACTTGGCCAACATGAGGATCACCCATGTCTGCAGGGCCAAGT

GGCACCGAGTCGGTGCTTTTTTTGAATTCTGATGCGGTATTTTCTCCTTACGCATCTGTGCGGTATTT

CACACCGCATACGTCAAAGCAACCATAGTACGCGCCCTGTATTTCCCATGATTCCTTCATATTTGCAT

ATACGATACAAGGCTGTTAGAGAGATAATTGGAATTAATTTGACTGTAAACACAAAGATATTAGTACA

AAATACGTGACGTAGAAAGTAATAATTTCTTGGGTAGTTTGCAGTTTTAAAATTATGTTTTAAAATGG

ACTATCATATGCTTACCGTAACTTGAAAGTATTTCGATTTCTTGGCTTTATATATCTTGTGGAAAGGA

CGAAACACCGAAGCTTCGGGAGGGTTTTAGAGCTAGGCCAACATGAGGATCACCCATGTCTGCAGGGC

CTAGCAAGTTAAAATAAGGCTAGTCCGTTATCAACTTGGCCAACATGAGGATCACCCATGTCTGCAGG

GCCAAGTGGCACCGAGTCGGTGCTTTTTTTGAATTCTGATGCGGTATTTTCTCCTTACGCATCTGTGC

GGTATTTCACACCGCATACGTCAAAGCAACCATAGTACGCGCCCTGTAGCGGACCCAAGTTTGTACAA

AAAAGCAGGCTAGGCTCCGGTGCCCGTCAGTGGGCAGAGCGCACATCGCCCACAGTCCCCGAGAAGTT

GGGGGGAGGGGTCGGCAATTGAACCGGTGCCTAGAGAAGGTGGCGCGGGGTAAACTGGGAAAGTGATG

TCGTGTACTGGCTCCGCCTTTTTCCCGAGGGTGGGGGAGAACCGTATATAAGTGCAGTAGTCGCCGTG

AACGTTCTTTTTCGCAACGGGTTTGCCGCCAGAACACAGCTTAAGCTTGGTACCGAGCTCGGATCCAC

TAGTAACGGCCGCCAGTGTGCTGGAATTCTGCAGATATCCATCACACTGGCGGCCGCTCGAGCATGCA

TCTAGAGGACAACTTTGTATACAAAAGTTGAGGCTGGATCCCGGTACCCTCGACACCTGCTGACAGGT

CCACCATGGGACCTAAGAAAAGAGGAAGGTGGCGGCCGCTGACTACAAGGATGACGACGATAAATCT

AGAATGGCTTCTAACTTTACTCAGTTCGTTCTCGTCGACAATGGCGGAACTGGCGACGTGACTGTCGC

CCCAAGCAACTTCGCTAACGGGATCGCTGAATGGATCAGCTCTAACTCGCGTTCACAGGCTTACAAAG

TAACCTGTAGCGTTCGTCAGAGCTCTGCGCAGAATCGCAAATACACCATCAAAGTCGAGGTGCCTAAA

GGCGCCTGGCGTTCGTACTTAAATATGGAACTAACCATTCCAATTTTCGCCACGAATTCCGACTGCGA

GCTTATTGTTAAGGCAATGCAAAGTCTCCTAAAAGATGGAAACCCGATTCCCTCAGCAATCGCAGCAA

ACTCCGGCATCTACGAGGCCAGCCCCAAGAAGAAGAGGAAGGTGAGTGGTGGAGGAAGTGGCGGGTCA

GGGTCGAGCCCCAAGAAAAAACGGAAAGTGGAGGCATCAATGAAGGAGGGAGAAAACAACAAACCCAG
```

-continued

```
GGAGAAAAGTGAAGGGAATAAGAGAAAAAGCTCCTTCTCTAACAGTGCAGACGATATCAAGTCCAAGA
AAAAGCGGGAGCAGTCTAATGACATTGCTAGGGGCTTCGAGAGAGGACTGGAGCCAGAAAAAATCATT
GGGGCAACCGACAGCTGCGGCGATCTGATGTTTCTCATGAAATGGAAGGACACAGATGAGGCCGACCT
GGTGCTCGCCAAAGAAGCTAACGTGAAGTGTCCCCAGATCGTCATTGCTTTTTACGAGGAAAGGCTCA
CCTGGCACGCATATCCTGAGGATGCCGAAAACAAGGAGAAGGAATCAGCTAAGAGCTCGGGAGGTGGT
TCGGGTGGCTCTGGATCAATGGACGCGAAATCACTTACGGCATGGTCGAGAACACTGGTTACGTTCAA
GGACGTGTTTGTGGACTTTACACGTGAGGAGTGGAAATTGCTGGATACTGCGCAACAAATTGTGTATC
GAAATGTCATGCTTGAGAATTACAAGAACCTCGTCAGTCTCGGATACCAGTTGACGAAACCGGATGTG
ATCCTTAGGCTCGAAAAGGGGGAAGAACCTTGGCTGGTATAGAAGAATTCGATCCCGCTTCAGTGCAG
GTGAATTCTACCACCCAGCTTAAGCTTGGTACCGAGCTCGGATCCACTAGTAACGGCCGCCAGTGTGC
TGGAATTCTGCAGATATCCATCACACTGGCGGCCGCTCGAGCATGCATCTAGAGGTACCCAGCTTTCT
TGTACAAAGTGGTAAGCTTGCCTCGAGCAGCGCTGCTCGAGAGATCTACGGGTGGCATCCCTGTGACC
CCTCCCCAGTGCCTCTCCTGGCCCTGGAAGTTGCCACTCCAGTGCCCACCAGCCTTGTCCTAATAAAA
TTAAGTTGCATCATTTTGTCTGACTAGGTGTCCTTCTATAATATTATGGGGTGGAGGGGGGTGGTATG
GAGCAAGGGGCAAGTTGGGAAGACAACCTGTAGGGCCTGCGGGGTCTATTGGGAACCAAGCTGGAGTG
CAGTGGCACAATCTTGGCTCACTGCAATCTCCGCCTCCTGGGTTCAAGCGATTCTCCTGCCTCAGCCT
CCCGAGTTGTTGGGATTCCAGGCATGCATGACCAGGCTCAGCTAATTTTGTTTTTTGGTAGAGACG
GGGTTTCACCATATTGGCCAGGCTGGTCTCCAACTCCTAATCTCAGGTGATCTACCCACCTTGGCCTC
CCAAATTGCTGGGATTACAGGCGTGAACCACTGCTCCCTTCCCTGTCCTTCTGATTTTGTAGGTAACC
ACGTGCGGACCGAGCGGCCGCAGGAACCCCTAGTGATGGAGTTGGCCACTCCCTCTCTGCGCGCTCGC
TCGCTCACTGAGGCCGGGCGACCAAAGGTCGCCCGACGCCCGGGCTTTGCCCGGGCGGCCTCAGTGAG
CGAGCGAGCGCGCAGCTGCCTGCAGGGGCGCCTGATGCGGTATTTTCTCCTTACGCATCTGTGCGGTA
TTTCACACCGCATACGTCAAAGCAACCATAGTACGCGCCCTGTAGCGGCGCATTAAGCGCGGCGGGTG
TGGTGGTTACGCGCAGCGTGACCGCTACACTTGCCAGCGCCCTAGCGCCCGCTCCTTTCGCTTTCTTC
CCTTCCTTTCTCGCCACGTTCGCCGGCTTTCCCCGTCAAGCTCTAAATCGGGGGCTCCCTTTAGGGTT
CCGATTTAGTGCTTTACGGCACCTCGACCCCAAAAAACTTGATTTGGGTGATGGTTCACGTAGTGGGC
CATCGCCCTGATAGACGGTTTTTCGCCCTTTGACGTTGGAGTCCACGTTCTTTAATAGTGGACTCTTG
TTCCAAACTGGAACAACACTCAACCCTATCTCGGGCTATTCTTTTGATTTATAAGGGATTTTGCCGAT
TTCGGCCTATTGGTTAAAAAATGAGCTGATTTAACAAAAATTTAACGCGAATTTTAACAAAATATTAA
CGTTTACAATTTTATGGTGCACTCTCAGTACAATCTGCTCTGATGCCGCATAGTTAAGCCAGCCCCGA
CACCCGCCAACACCCGCTGACGCGCCCTGACGGGCTTGTCTGCTCCCGGCATCCGCTTACAGACAAGC
TGTGACCGTCTCCGGGAGCTGCATGTGTCAGAGGTTTTCACCGTCATCACCGAAACGCGCGAGACGAA
AGGGCCTCGTGATACGCCTATTTTTATAGGTTAATGTCATGATAATAATGGTTTCTTAGACGTCAGGT
GGCACTTTTCGGGGAAATGTGCGCGGAACCCCTATTTGTTTATTTTTCTAAATACATTCAAATATGTA
TCCGCTCATGAGACAATAACCCTGATAAATGCTTCAATAATATTGAAAAAGGAAGAGTATGAGTATTC
AACATTTCCGTGTCGCCCTTATTCCCTTTTTTGCGGCATTTTGCCTTCCTGTTTTTGCTCACCCAGAA
ACGCTGGTGAAAGTAAAAGATGCTGAAGATCAGTTGGGTGCACGAGTGGGTTACATCGAACTGGATCT
CAACAGCGGTAAGATCCTTGAGAGTTTTCGCCCCGAAGAACGTTTTCCAATGATGAGCACTTTTAAAG
TTCTGCTATGTGGCGCGGTATTATCCCGTATTGACGCCGGGCAAGAGCAACTCGGTCGCCGCATACAC
TATTCTCAGAATGACTTGGTTGAGTACTCACCAGTCACAGAAAAGCATCTTACGGATGGCATGACAGT
AAGAGAATTATGCAGTGCTGCCATAACCATGAGTGATAACACTGCGGCCAACTTACTTCTGACAACGA
```

-continued

```
TCGGAGGACCGAAGGAGCTAACCGCTTTTTTGCACAACATGGGGGATCATGTAACTCGCCTTGATCGT

TGGGAACCGGAGCTGAATGAAGCCATACCAAACGACGAGCGTGACACCACGATGCCTGTAGCAATGGC

AACAACGTTGCGCAAACTATTAACTGGCGAACTACTTACTCTAGCTTCCCGGCAACAATTAATAGACT

GGATGGAGGCGGATAAAGTTGCAGGACCACTTCTGCGCTCGGCCCTTCCGGCTGGCTGGTTTATTGCT

GATAAATCTGGAGCCGGTGAGCGTGGGTCTCGCGGTATCATTGCAGCACTGGGGCCAGATGGTAAGCC

CTCCCGTATCGTAGTTATCTACACGACGGGGAGTCAGGCAACTATGGATGAACGAAATAGACAGATCG

CTGAGATAGGTGCCTCACTGATTAAGCATTGGTAACTGTCAGACCAAGTTTACTCATATATACTTTAG

ATTGATTTAAAACTTCATTTTTAATTTAAAAGGATCTAGGTGAAGATCCTTTTTGATAATCTCATGAC

CAAAATCCCTTAACGTGAGTTTTCGTTCCACTGAGCGTCAGACCCCGTAGAAAAGATCAAAGGATCTT

CTTGAGATCCTTTTTTTCTGCGCGTAATCTGCTGCTTGCAAACAAAAAAACCACCGCTACCAGCGGTG

GTTTGTTTGCCGGATCAAGAGCTACCAACTCTTTTTCCGAAGGTAACTGGCTTCAGCAGAGCGCAGAT

ACCAAATACTGTCCTTCTAGTGTAGCCGTAGTTAGGCCACCACTTCAAGAACTCTGTAGCACCGCCTA

CATACCTCGCTCTGCTAATCCTGTTACCAGTGGCTGCTGCCAGTGGCGATAAGTCGTGTCTTACCGGG

TTGGACTCAAGACGATAGTTACCGGATAAGGCGCAGCGGTCGGGCTGAACGGGGGGTTCGTGCACACA

GCCCAGCTTGGAGCGAACGACCTACACCGAACTGAGATACCTACAGCGTGAGCTATGAGAAAGCGCCA

CGCTTCCCGAAGGGAGAAAGGCGGACAGGTATCCGGTAAGCGGCAGGGTCGGAACAGGAGAGCGCACG

AGGGAGCTTCCAGGGGGAAACGCCTGGTATCTTTATAGTCCTGTCGGGTTTCGCCACCTCTGACTTGA

GCGTCGATTTTTGTGATGCTCGTCAGGGGGCGGAGCCTATGGAAAAACGCCAGCAACGCGGCCTTTT

TACGGTTCCTGGCCTTTTGCTGGCCTTTTGCTCACATGT
```

AAV2/1-CXCR4

(SEQ ID NO: 65)
```
CCTGCAGGCAGCTGCGCGCTCGCTCGCTCACTGAGGCCGCCCGGGCGTCGGGCGACCTTTGGTCGCCC

GGCCTCAGTGAGCGAGCGAGCGCGCAGAGAGGGAGTGGCCAACTCCATCACTAGGGGTTCCTGCGGCC

GCACGCGTTGATATCAACTTTGTATAGAAAAGTTTTCCCATGATTCCTTCATATTTGCATATACGATA

CAAGGCTGTTAGAGAGATAATTGGAATTAATTTGACTGTAAACACAAAGATATTAGTACAAAATACGT

GACGTAGAAAGTAATAATTTCTTGGGTAGTTTGCAGTTTTAAAATTATGTTTTAAAATGGACTATCAT

ATGCTTACCGTAACTTGAAAGTATTTCGATTTCTTGGCTTTATATATCTTGTGGAAAGGACGAAACAC

CATAAAAGTCCGGTTGTTTTAGAGCTAGGCCAACATGAGGATCACCCATGTCTGCAGGGCCTAGCAAG

TTAAAATAAGGCTAGTCCGTTATCAACTTGGCCAACATGAGGATCACCCATGTCTGCAGGGCCAAGTG

GCACCGAGTCGGTGCTTTTTTGAATTCTGATGCGGTATTTTCTCCTTACGCATCTGTGCGGTATTTC

ACACCGCATACGTCAAAGCAACCATAGTACGCGCCCTGTATTTCCCATGATTCCTTCATATTTGCATA

TACGATACAAGGCTGTTAGAGAGATAATTGGAATTAATTTGACTGTAAACACAAAGATATTAGTACAA

AATACGTGACGTAGAAAGTAATAATTTCTTGGGTAGTTTGCAGTTTTAAAATTATGTTTTAAAATGGA

CTATCATATGCTTACCGTAACTTGAAAGTATTTCGATTTCTTGGCTTTATATATCTTGTGGAAAGGAC

GAAACACCTCCGGTAACCACCAGTTTTAGAGCTAGGCCAACATGAGGATCACCCATGTCTGCAGGGCC

TAGCAAGTTAAAATAAGGCTAGTCCGTTATCAACTTGGCCAACATGAGGATCACCCATGTCTGCAGGG

CCAAGTGGCACCGAGTCGGTGCTTTTTTGAATTCTGATGCGGTATTTTCTCCTTACGCATCTGTGCG

GTATTTCACACCGCATACGTCAAAGCAACCATAGTACGCGCCCTGTAGCGGACCCAAGTTTGTACAAA

AAAGCAGGCTAGGCTCCGGTGCCCGTCAGTGGGCAGAGCGCACATCGCCCACAGTCCCCGAGAAGTTG

GGGGGAGGGGTCGGCAATTGAACCGGTGCCTAGAGAAGGTGGCGCGGGGTAAACTGGGAAAGTGATGT

CGTGTACTGGCTCCGCCTTTTTCCCGAGGGTGGGGGAGAACCGTATATAAGTGCAGTAGTCGCCGTGA
```

-continued
ACGTTCTTTTTCGCAACGGGTTTGCCGCCAGAACACAGCTTAAGCTTGGTACCGAGCTCGGATCCACT

AGTAACGGCCGCCAGTGTGCTGGAATTCTGCAGATATCCATCACACTGGCGGCCGCTCGAGCATGCAT

CTAGAGGACAACTTTGTATACAAAAGTTGAGGCTGGATCCCGGTACCCTCGACACCTGCTGACAGGTC

CACCATGGGACCTAAGAAAAAGAGGAAGGTGGCGGCCGCTGACTACAAGGATGACGACGATAAATCTA

GAATGGCTTCTAACTTTACTCAGTTCGTTCTCGTCGACAATGGCGGAACTGGCGACGTGACTGTCGCC

CCAAGCAACTTCGCTAACGGGATCGCTGAATGGATCAGCTCTAACTCGCGTTCACAGGCTTACAAAGT

AACCTGTAGCGTTCGTCAGAGCTCTGCGCAGAATCGCAAATACACCATCAAAGTCGAGGTGCCTAAAG

GCGCCTGGCGTTCGTACTTAAATATGGAACTAACCATTCCAATTTTCGCCACGAATTCCGACTGCGAG

CTTATTGTTAAGGCAATGCAAAGTCTCCTAAAAGATGGAAACCCGATTCCCTCAGCAATCGCAGCAAA

CTCCGGCATCTACGAGGCCAGCCCCAAGAAGAAGAGGAAGGTGAGTGGTGGAGGAAGTGGCGGGTCAG

GGTCGAGCCCCAAGAAAAAACGGAAAGTGGAGGCATCAATGAAGGAGGGAGAAAACAACAAACCCAGG

GAGAAAAGTGAAGGGAATAAGAGAAAAAGCTCCTTCTCTAACAGTGCAGACGATATCAAGTCCAAGAA

AAAGCGGGAGCAGTCTAATGACATTGCTAGGGGCTTCGAGAGAGGACTGGAGCCAGAAAAATCATTG

GGGCAACCGACAGCTGCGGCGATCTGATGTTTCTCATGAAATGGAAGGACACAGATGAGGCCGACCTG

GTGCTCGCCAAAGAAGCTAACGTGAAGTGTCCCCAGATCGTCATTGCTTTTTACGAGGAAAGGCTCAC

CTGGCACGCATATCCTGAGGATGCCGAAAACAAGGAGAAGGAATCAGCTAAGAGCTCGGAGGTGGTT

CGGGTGGCTCTGGATCAATGGACGCGAAATCACTTACGGCATGGTCGAGAACACTGGTTACGTTCAAG

GACGTGTTTGTGGACTTTACACGTGAGGAGTGGAAATTGCTGGATACTGCGCAACAAATTGTGTATCG

AAATGTCATGCTTGAGAATTACAAGAACCTCGTCAGTCTCGGATACCAGTTGACGAAACCGGATGTGA

TCCTTAGGCTCGAAAAGGGGGAAGAACCTTGGCTGGTATAGAAGAATTCGATCCCGCTTCAGTGCAGG

TGAATTCTACCACCCAGCTTAAGCTTGGTACCGAGCTCGGATCCACTAGTAACGGCCGCCAGTGTGCT

GGAATTCTGCAGATATCCATCACACTGGCGGCCGCTCGAGCATGCATCTAGAGGTACCCAGCTTTCTT

GTACAAAGTGGTAAGCTTGCCTCGAGCAGCGCTGCTCGAGAGATCTACGGGTGGCATCCCTGTGACCC

CTCCCCAGTGCCTCTCCTGGCCCTGGAAGTTGCCACTCCAGTGCCCACCAGCCTTGTCCTAATAAAAT

TAAGTTGCATCATTTTGTCTGACTAGGTGTCCTTCTATAATATTATGGGGTGGAGGGGGGTGGTATGG

AGCAAGGGGCAAGTTGGGAAGACAACCTGTAGGGCCTGCGGGGTCTATTGGGAACCAAGCTGGAGTGC

AGTGGCACAATCTTGGCTCACTGCAATCTCCGCCTCCTGGGTTCAAGCGATTCTCCTGCCTCAGCCTC

CCGAGTTGTTGGGATTCCAGGCATGCATGACCAGGCTCAGCTAATTTTTGTTTTTTTGGTAGAGACGG

GGTTTCACCATATTGGCCAGGCTGGTCTCCAACTCCTAATCTCAGGTGATCTACCCACCTTGGCCTCC

CAAATTGCTGGGATTACAGGCGTGAACCACTGCTCCCTTCCCTGTCCTTCTGATTTTGTAGGTAACCA

CGTGCGACCGAGCGGCCGCAGGAACCCCTAGTGATGGAGTTGGCCACTCCCTCTCTGCGCGCTCGCT

CGCTCACTGAGGCCGGGCGACCAAAGGTCGCCCGACGCCCGGGCTTTGCCCGGGCGGCCTCAGTGAGC

GAGCGAGCGCGCAGCTGCCTGCAGGGGCGCCTGATGCGGTATTTTCTCCTTACGCATCTGTGCGGTAT

TCACACCGCATACGTCAAAGCAACCATAGTACGCGCCCTGTAGCGGCGCATTAAGCGCGGCGGGTGT

GGTGGTTACGCGCAGCGTGACCGCTACACTTGCCAGCGCCCTAGCGCCCGCTCCTTTCGCTTTCTTCC

CTTCCTTTCTCGCCACGTTCGCCGGCTTTCCCCGTCAAGCTCTAAATCGGGGGCTCCCTTTAGGGTTC

CGATTTAGTGCTTTACGGCACCTCGACCCCAAAAAACTTGATTTGGGTGATGGTTCACGTAGTGGGCC

ATCGCCCTGATAGACGGTTTTTCGCCCTTTGACGTTGGAGTCCACGTTCTTTAATAGTGGACTCTTGT

TCCAAACTGGAACAACACTCAACCCTATCTCGGGCTATTCTTTTGATTTATAAGGGATTTTGCCGATT

TCGGCCTATTGGTTAAAAAATGAGCTGATTTAACAAAAATTTAACGCGAATTTTAACAAAATATTAAC

GTTTACAATTTTATGGTGCACTCTCAGTACAATCTGCTCTGATGCCGCATAGTTAAGCCAGCCCCGAC

-continued

```
ACCCGCCAACACCCGCTGACGCGCCCTGACGGGCTTGTCTGCTCCCGGCATCCGCTTACAGACAAGCT
GTGACCGTCTCCGGGAGCTGCATGTGTCAGAGGTTTTCACCGTCATCACCGAAACGCGCGAGACGAAA
GGGCCTCGTGATACGCCTATTTTTATAGGTTAATGTCATGATAATAATGGTTTCTTAGACGTCAGGTG
GCACTTTTCGGGGAAATGTGCGCGGAACCCCTATTTGTTTATTTTTCTAAATACATTCAAATATGTAT
CCGCTCATGAGACAATAACCCTGATAAATGCTTCAATAATATTGAAAAAGGAAGAGTATGAGTATTCA
ACATTTCCGTGTCGCCCTTATTCCCTTTTTTGCGGCATTTTGCCTTCCTGTTTTTGCTCACCCAGAAA
CGCTGGTGAAAGTAAAAGATGCTGAAGATCAGTTGGGTGCACGAGTGGGTTACATCGAACTGGATCTC
AACAGCGGTAAGATCCTTGAGAGTTTTCGCCCCGAAGAACGTTTTCCAATGATGAGCACTTTTAAAGT
TCTGCTATGTGGCGCGGTATTATCCCGTATTGACGCCGGGCAAGAGCAACTCGGTCGCCGCATACACT
ATTCTCAGAATGACTTGGTTGAGTACTCACCAGTCACAGAAAAGCATCTTACGGATGGCATGACAGTA
AGAGAATTATGCAGTGCTGCCATAACCATGAGTGATAACACTGCGGCCAACTTACTTCTGACAACGAT
CGGAGGACCGAAGGAGCTAACCGCTTTTTTGCACAACATGGGGGATCATGTAACTCGCCTTGATCGTT
GGGAACCGGAGCTGAATGAAGCCATACCAAACGACGAGCGTGACACCACGATGCCTGTAGCAATGGCA
ACAACGTTGCGCAAACTATTAACTGGCGAACTACTTACTCTAGCTTCCCGGCAACAATTAATAGACTG
GATGGAGGCGGATAAAGTTGCAGGACCACTTCTGCGCTCGGCCCTTCCGGCTGGCTGGTTTATTGCTG
ATAAATCTGGAGCCGGTGAGCGTGGGTCTCGCGGTATCATTGCAGCACTGGGGCCAGATGGTAAGCCC
TCCCGTATCGTAGTTATCTACACGACGGGGAGTCAGGCAACTATGGATGAACGAAATAGACAGATCGC
TGAGATAGGTGCCTCACTGATTAAGCATTGGTAACTGTCAGACCAAGTTTACTCATATATACTTTAGA
TTGATTTAAAACTTCATTTTTAATTTAAAAGGATCTAGGTGAAGATCCTTTTTGATAATCTCATGACC
AAAATCCCTTAACGTGAGTTTTCGTTCCACTGAGCGTCAGACCCCGTAGAAAAGATCAAAGGATCTTC
TTGAGATCCTTTTTTTCTGCGCGTAATCTGCTGCTTGCAAACAAAAAAACCACCGCTACCAGCGGTGG
TTTGTTTGCCGGATCAAGAGCTACCAACTCTTTTTCCGAAGGTAACTGGCTTCAGCAGAGCGCAGATA
CCAAATACTGTCCTTCTAGTGTAGCCGTAGTTAGGCCACCACTTCAAGAACTCTGTAGCACCGCCTAC
ATACCTCGCTCTGCTAATCCTGTTACCAGTGGCTGCTGCCAGTGGCGATAAGTCGTGTCTTACCGGGT
TGGACTCAAGACGATAGTTACCGGATAAGGCGCAGCGGTCGGGCTGAACGGGGGGTTCGTGCACACAG
CCCAGCTTGGAGCGAACGACCTACACCGAACTGAGATACCTACAGCGTGAGCTATGAGAAAGCGCCAC
GCTTCCCGAAGGGAGAAAGGCGGACAGGTATCCGGTAAGCGGCAGGGTCGGAACAGGAGAGCGCACGA
GGGAGCTTCCAGGGGGAAACGCCTGGTATCTTTATAGTCCTGTCGGGTTTCGCCACCTCTGACTTGAG
CGTCGATTTTTGTGATGCTCGTCAGGGGGCGGAGCCTATGGAAAAACGCCAGCAACGCGGCCTTTTT
ACGGTTCCTGGCCTTTTGCTGGCCTTTTGCTCACATGT
```

AAV2/DJ-Cas9 and AAV/2/1 Cas9
(SEQ ID NO: 66)
```
CCTGCAGGCAGCTGCGCGCTCGCTCGCTCACTGAGGCCGCCCGGGCAAAGCCCGGGCGTCGGGCGACC
TTTGGTCGCCCGGCCTCAGTGAGCGAGCGAGCGCGCAGAGAGGGAGTGGCCAACTCCATCACTAGGGG
TTCCTGCGGCCTCTAGAAATGTAGTCTTATGCAATACTCTTGTAGTCTTGCAACATGGTAACGATGAG
TTAGCAACATGCCTTACAAGGAGAGAAAAAGCACCGTGCATGCCGATTGGTGGAAGTAAGGTGGTACG
ATCGTGCCTTATTAGGAAGGCAACAGACGGGTCTGACATGGATTGGACGAACCACTGAATTGCCGCAT
TGCAGAGATATTGTATTTAAGTGCCTAGCTCGATACATAAAACCGGTGCCACCATGTACCCATACGAT
GTTCCAGATTACGCTTCGCCGAAGAAAAGCGCAAGGTCGAAGCGTCCGACAAGAAGTACAGCATCGG
CCTGGACATCGGCACCAACTCTGTGGGCTGGGCCGTGATCACCGACGAGTACAAGGTGCCCAGCAAGA
AATTCAAGGTGCTGGGCAACACCGACCGGCACAGCATCAAGAAGAACCTGATCGGAGCCCTGCTGTTC
```

-continued

```
GACAGCGGCGAAACAGCCGAGGCCACCCGGCTGAAGAGAACCGCCAGAAGAAGATACACCAGACGGAA
GAACCGGATCTGCTATCTGCAAGAGATCTTCAGCAACGAGATGGCCAAGGTGGACGACAGCTTCTTCC
ACAGACTGGAAGAGTCCTTCCTGGTGGAAGAGGATAAGAAGCACGAGCGGCACCCCATCTTCGGCAAC
ATCGTGGACGAGGTGGCCTACCACGAGAAGTACCCCACCATCTACCACCTGAGAAAGAAACTGGTGGA
CAGCACCGACAAGGCCGACCTGCGGCTGATCTATCTGGCCCTGGCCCACATGATCAAGTTCCGGGGCC
ACTTCCTGATCGAGGGCGACCTGAACCCCGACAACAGCGACGTGGACAAGCTGTTCATCCAGCTGGTG
CAGACCTACAACCAGCTGTTCGAGGAAAACCCCATCAACGCCAGCGGCGTGGACGCCAAGGCCATCCT
GTCTGCCAGACTGAGCAAGAGCAGACGGCTGGAAAATCTGATCGCCCAGCTGCCCGGCGAGAAGAAGA
ATGGCCTGTTCGGCAACCTGATTGCCCTGAGCCTGGGCCTGACCCCCAACTTCAAGAGCAACTTCGAC
CTGGCCGAGGATGCCAAACTGCAGCTGAGCAAGGACACCTACGACGACGACCTGGACAACCTGCTGGC
CCAGATCGGCGACCAGTACGCCGACCTGTTTCTGGCCGCCAAGAACCTGTCCGACGCCATCCTGCTGA
GCGACATCCTGAGAGTGAACACCGAGATCACCAAGGCCCCCCTGAGCGCCTCTATGATCAAGAGATAC
GACGAGCACCACCAGGACCTGACCCTGCTGAAAGCTCTCGTGCGGCAGCAGCTGCCTGAGAAGTACAA
AGAGATTTTCTTCGACCAGAGCAAGAACGGCTACGCCGGCTACATTGACGGCGGAGCCAGCCAGGAAG
AGTTCTACAAGTTCATCAAGCCCATCCTGGAAAAGATGGACGGCACCGAGGAACTGCTCGTGAAGCTG
AACAGAGAGGACCTGCTGCGGAAGCAGCGGACCTTCGACAACGGCAGCATCCCCCACCAGATCCACCT
GGGAGAGCTGCACGCCATTCTGCGGCGGCAGGAAGATTTTTACCCATTCCTGAAGGACAACCGGGAAA
AGATCGAGAAGATCCTGACCTTCCGCATCCCCTACTACGTGGGCCCTCTGGCCAGGGGAAACAGCAGA
TTCGCCTGGATGACCAGAAGAGCGAGGAAACCATCACCCCCTGGAACTTCGAGGAAGTGGTGGACAA
GGGCGCTTCCGCCCAGAGCTTCATCGAGCGGATGACCAACTTCGATAAGAACCTGCCCAACGAGAAGG
TGCTGCCCAAGCACAGCCTGCTGTACGAGTACTTCACCGTGTATAACGAGCTGACCAAAGTGAAATAC
GTGACCGAGGGAATGAGAAAGCCCGCCTTCCTGAGCGGCGAGCAGAAAAAGGCCATCGTGGACCTGCT
GTTCAAGACCAACCGGAAAGTGACCGTGAAGCAGCTGAAAGAGGACTACTTCAAGAAAATCGAGTGCT
TCGACTCCGTGGAAATCTCCGGCGTGGAAGATCGGTTCAACGCCTCCCTGGGCACATACCACGATCTG
CTGAAAATTATCAAGGACAAGGACTTCCTGGACAATGAGGAAAACGAGGACATTCTGGAAGATATCGT
GCTGACCCTGACACTGTTTGAGGACAGAGAGATGATCGAGGAACGGCTGAAAACCTATGCCCACCTGT
TCGACGACAAAGTGATGAAGCAGCTGAAGCGGCGGAGATACACCGGCTGGGGCAGGCTGAGCCGGAAG
CTGATCAACGGCATCCGGGACAAGCAGTCCGGCAAGACAATCCTGGATTTCCTGAAGTCCGACGGCTT
CGCCAACAGAAACTTCATGCAGCTGATCCACGACGACAGCCTGACCTTTAAAGAGGACATCCAGAAAG
CCCAGGTGTCCGGCCAGGGCGATAGCCTGCACGAGCACATTGCCAATCTGGCCGGCAGCCCCGCCATT
AAGAAGGGCATCCTGCAGACAGTGAAGGTGGTGGACGAGCTCGTGAAAGTGATGGGCCGGCACAAGCC
CGAGAACATCGTGATCGAAATGGCCAGAGAGAACCAGACCACCCAGAAGGGACAGAAGAACAGCCGCG
AGAGAATGAAGCGGATCGAAGAGGGCATCAAAGAGCTGGGCAGCCAGATCCTGAAAGAACACCCCGTG
GAAAACACCCAGCTGCAGAACGAGAAGCTGTACCTGTACTACCTGCAGAATGGGCGGGATATGTACGT
GGACCAGGAACTGGACATCAACCGGCTGTCCGACTACGATGTGGACCATATCGTGCCTCAGAGCTTTC
TGAAGGACGACTCCATCGACAACAAGGTGCTGACCAGAAGCGACAAGAACCGGGGCAAGAGCGACAAC
GTGCCCTCCGAAGAGGTCGTGAAGAAGATGAAGAACTACTGGCGGCAGCTGCTGAACGCCAAGCTGAT
TACCCAGAGAAAGTTCGACAATCTGACCAAGGCCGAGAGAGGCGGCCTGAGCGAACTGGATAAGGCCG
GCTTCATCAAGAGACAGCTGGTGGAAACCCGGCAGATCACAAAGCACGTGGCACAGATCCTGGACTCC
CGGATGAACACTAAGTACGACGAGAATGACAAGCTGATCCGGGAAGTGAAAGTGATCACCCTGAAGTC
CAAGCTGGTGTCCGATTTCCGGAAGGATTTCCAGTTTTACAAAGTGCGCGAGATCAACAACTACCACC
```

-continued

```
ACGCCCACGACGCCTACCTGAACGCCGTCGTGGGAACCGCCCTGATCAAAAAGTACCCTAAGCTGGAA

AGCGAGTTCGTGTACGGCGACTACAAGGTGTACGACGTGCGGAAGATGATCGCCAAGAGCGAGCAGGA

AATCGGCAAGGCTACCGCCAAGTACTTCTTCTACAGCAACATCATGAACTTTTTCAAGACCGAGATTA

CCCTGGCCAACGGCGAGATCCGGAAGCGGCCTCTGATCGAGACAAACGGCGAAACCGGGGAGATCGTG

TGGGATAAGGGCCGGGATTTTGCCACCGTGCGGAAAGTGCTGAGCATGCCCCAAGTGAATATCGTGAA

AAAGACCGAGGTGCAGACAGGCGGCTTCAGCAAAGAGTCTATCCTGCCCAAGAGGAACAGCGATAAGC

TGATCGCCAGAAAGAAGGACTGGGACCCTAAGAAGTACGGCGGCTTCGACAGCCCCACCGTGGCCTAT

TCTGTGCTGGTGGTGGCCAAAGTGGAAAAGGGCAAGTCCAAGAAACTGAAGAGTGTGAAAGAGCTGCT

GGGGATCACCATCATGGAAAGAAGCAGCTTCGAGAAGAATCCCATCGACTTTCTGGAAGCCAAGGGCT

ACAAAGAAGTGAAAAAGGACCTGATCATCAAGCTGCCTAAGTACTCCCTGTTCGAGCTGGAAAACGGC

CGGAAGAGAATGCTGGCCTCTGCCGGCGAACTGCAGAAGGGAAACGAACTGGCCCTGCCCTCCAAATA

TGTGAACTTCCTGTACCTGGCCAGCCACTATGAGAAGCTGAAGGGCTCCCCCGAGGATAATGAGCAGA

AACAGCTGTTTGTGGAACAGCACAAGCACTACCTGGACGAGATCATCGAGCAGATCAGCGAGTTCTCC

AAGAGAGTGATCCTGGCCGACGCTAATCTGGACAAAGTGCTGTCCGCCTACAACAAGCACCGGGATAA

GCCCATCAGAGAGCAGGCCGAGAATATCATCCACCTGTTTACCCTGACCAATCTGGGAGCCCCTGCCG

CCTTCAAGTACTTTGACACCACCATCGACCGGAAGAGGTACACCAGCACCAAAGAGGTGCTGGACGCC

ACCCTGATCCACCAGAGCATCACCGGCCTGTACGAGACACGGATCGACCTGTCTCAGCTGGGAGGCGA

CAGCCCCAAGAAGAAGAGAAAGGTGGAGGCCAGCTAAGAATTCAGCGGCGCGCCTTCCCAAAACCCAC

CAAACTAAGTAACTGCTACTTCTCTCAGCAACACCAAGATCAATGAAAGAGGCAAGGTGGGTCTTCGA

GAAGACCTGCTTAATAAAAGATCTTTATTTTCATTAGATCTGTGTGTTGGTTTTTTGTGTGGCGGCCG

CAGGAACCCCTAGTGATGGAGTTGGCCACTCCCTCTCTGCGCGCTCGCTCGCTCACTGAGGCCGGGCG

ACCAAAGGTCGCCCGACGCCCGGGCTTTGCCCGGGCGGCCTCAGTGAGCGAGCGAGCGCGCAGCTGCC

TGCAGGGGCGCCTGATGCGGTATTTTCTCCTTACGCATCTGTGCGGTATTTCACACCGCATACGTCAA

AGCAACCATAGTACGCGCCCTGTAGCGGCGCATTAAGCGCGGCGGGTGTGGTGGTTACGCGCAGCGTG

ACCGCTACACTTGCCAGCGCCCTAGCGCCCGCTCCTTTCGCTTTCTTCCCTTCCTTTCTCGCCACGTT

CGCCGGCTTTCCCCGTCAAGCTCTAAATCGGGGGCTCCCTTTAGGGTTCCGATTTAGTGCTTTACGGC

ACCTCGACCCCAAAAAACTTGATTTGGGTGATGGTTCACGTAGTGGGCCATCGCCCTGATAGACGGTT

TTTCGCCCTTTGACGTTGGAGTCCACGTTCTTTAATAGTGGACTCTTGTTCCAAACTGGAACAACACT

CAACCCTATCTCGGGCTATTCTTTTGATTTATAAGGGATTTTGCCGATTTCGGCCTATTGGTTAAAAA

ATGAGCTGATTTAACAAAAATTTAACGCGAATTTTAACAAAATATTAACGTTTACAATTTTATGGTGC

ACTCTCAGTACAATCTGCTCTGATGCCGCATAGTTAAGCCAGCCCCGACACCCGCCAACACCCGCTGA

CGCGCCCTGACGGGCTTGTCTGCTCCCGGCATCCGCTTACAGACAAGCTGTGACCGTCTCCGGGAGCT

GCATGTGTCAGAGGTTTTCACCGTCATCACCGAAACGCGCGAGACGAAAGGGCCTCGTGATACGCCTA

TTTTTATAGGTTAATGTCATGATAATAATGGTTTCTTAGACGTCAGGTGGCACTTTTCGGGGAAATGT

GCGCGGAACCCCTATTTGTTTATTTTTCTAAATACATTCAAATATGTATCCGCTCATGAGACAATAAC

CCTGATAAATGCTTCAATAATATTGAAAAAGGAAGAGTATGAGTATTCAACATTTCCGTGTCGCCCTT

ATTCCCTTTTTTGCGGCATTTTGCCTTCCTGTTTTTGCTCACCCAGAAACGCTGGTGAAAGTAAAAGA

TGCTGAAGATCAGTTGGGTGCACGAGTGGGTTACATCGAACTGGATCTCAACAGCGGTAAGATCCTTG

AGAGTTTTCGCCCCGAAGAACGTTTTCCAATGATGAGCACTTTTAAAGTTCTGCTATGTGGCGCGGTA

TTATCCCGTATTGACGCCGGGCAAGAGCAACTCGGTCGCCGCATACACTATTCTCAGAATGACTTGGT
```

-continued

```
TGAGTACTCACCAGTCACAGAAAAGCATCTTACGGATGGCATGACAGTAAGAGAATTATGCAGTGCTG

CCATAACCATGAGTGATAACACTGCGGCCAACTTACTTCTGACAACGATCGGAGGACCGAAGGAGCTA

ACCGCTTTTTTGCACAACATGGGGGATCATGTAACTCGCCTTGATCGTTGGGAACCGGAGCTGAATGA

AGCCATACCAAACGACGAGCGTGACACCACGATGCCTGTAGCAATGGCAACAACGTTGCGCAAACTAT

TAACTGGCGAACTACTTACTCTAGCTTCCCGGCAACAATTAATAGACTGGATGGAGGCGGATAAAGTT

GCAGGACCACTTCTGCGCTCGGCCCTTCCGGCTGGCTGGTTTATTGCTGATAAATCTGGAGCCGGTGA

GCGTGGAAGCCGCGGTATCATTGCAGCACTGGGGCCAGATGGTAAGCCCTCCCGTATCGTAGTTATCT

ACACGACGGGGAGTCAGGCAACTATGGATGAACGAAATAGACAGATCGCTGAGATAGGTGCCTCACTG

ATTAAGCATTGGTAACTGTCAGACCAAGTTTACTCATATATACTTTAGATTGATTTAAAACTTCATTT

TTAATTTAAAAGGATCTAGGTGAAGATCCTTTTTGATAATCTCATGACCAAAATCCCTTAACGTGAGT

TTTCGTTCCACTGAGCGTCAGACCCCGTAGAAAAGATCAAAGGATCTTCTTGAGATCCTTTTTTCTG

CGCGTAATCTGCTGCTTGCAAACAAAAAAACCACCGCTACCAGCGGTGGTTTGTTTGCCGGATCAAGA

GCTACCAACTCTTTTTCCGAAGGTAACTGGCTTCAGCAGAGCGCAGATACCAAATACTGTCCTTCTAG

TGTAGCCGTAGTTAGGCCACCACTTCAAGAACTCTGTAGCACCGCCTACATACCTCGCTCTGCTAATC

CTGTTACCAGTGGCTGCTGCCAGTGGCGATAAGTCGTGTCTTACCGGGTTGGACTCAAGACGATAGTT

ACCGGATAAGGCGCAGCGGTCGGGCTGAACGGGGGGTTCGTGCACACAGCCCAGCTTGGAGCGAACGA

CCTACACCGAACTGAGATACCTACAGCGTGAGCTATGAGAAAGCGCCACGCTTCCCGAAGGGAGAAAG

GCGGACAGGTATCCGGTAAGCGGCAGGGTCGGAACAGGAGAGCGCACGAGGGAGCTTCCAGGGGAAA

CGCCTGGTATCTTTATAGTCCTGTCGGGTTTCGCCACCTCTGACTTGAGCGTCGATTTTTGTGATGCT

CGTCAGGGGGCGGAGCCTATGGAAAAACGCCAGCAACGCGGCCTTTTTACGGTTCCTGGCCTTTTGC

TGGCCTTTTGCTCACATGT
```

Cell culture for endogenous target repression—HEK293FT, Neuro-2a, and Raw 264.7 cell lines (purchased from ATCC) were maintained in Dulbecco's modified Eagle's medium (DMEM—Life Technologies) with 10% fetal bovine serum (FBS—Life Technologies), 2 mM glutamine, 1.0 mM sodium pyruvate (Life Technologies) and 1% penicillin-streptomycin (Life Technologies) in incubators at 37° C. and 5% $CO_2$.

Transfection of in vitro cultured cells—HEK293FT cells were seeded approximately 50,000 cells per well in 24-well plates and transfected the next day. HEK293FT cells were co-transfected with plasmid DNAs encoding gRNA (10 ng), dCas9 (200 ng), MS2-fused repressor (100 ng), puromycin resistant gene (50 ng), and Enhance Blue Fluorescent Protein (EBFP) as a transfection control (25 ng). Polyethylenimine (PEI) (Polysciences) was used to transfect HEK293FT cells. Transfection complexes were prepared according to manufacturer's instructions. Cells were treated with 0.5 ug/ml puromycin (Gibco-life tech) at 24 hours post-transfection. Cells were collected 72 hours post-transfection and total RNA was collected from cells using RNAeasy Plus mini kit (Qiagen).

Neuro-2a cells were seeded approximately 50,000 cells per well in 24-well plates and transfected the next day. Cells were co-transfected with plasmids encoding gRNA (100 ng), Cas9 nuclease (70 ng), and EBFP as a transfection control (25 ng), and a Puromycin resistance gene (50 ng). Plasmids were delivered to Neuro-2a cells with Lipofectamine LTX. Cells were treated with 0.5 ug/ml puromycin (Gibco-life tech) at 24 hours post-transfection. 5 days later, cells were treated with LPS at the concentration of 10 ug/ml and after 5 hours total RNA was collected from cells using RNAeasy Plus mini kit (Qiagen).

For CXCR4 repression, Raw 264.7 cells were seeded approximately 50,000 cells per well in 24-well plates and transduced the next day. Cell culture media was removed and AAV was added to the culture at 1E+9 GC/cell in 250 microliter media. Media was refreshed 12 hours post-transduction. 5 days later, cells were treated with LPS at the concentration of 0.1 ug/ml for 5 hours and then total RNA was collected using RNAeasy Plus mini kit (Qiagen).

Quantitative RT-PCR Analysis—Cells or tissues were lysed and RNA was extracted using RNeasy Plus mini kit (Qiagen) or trizol (Life Technologies) followed by cDNA synthesis using the High-Capacity RNA-to-cDNA Kit (Thermo Fisher) or iScript cDNA synthesis kit (Bio-Rad). qRT-PCR was performed using SYBR Green PCR Master Mix (Thermo Fisher). All analyses were normalized to 18s rRNA ($\Delta Ct$) and fold-changes were calculated against un-transfected controls or Cas9 only groups for in vitro experiments and AAV-GFP injected group for in vivo experiments ($2^{-\Delta\Delta Ct}$). Primer sequences for qPCR are listed below.

DNA isolation and real-time PCR For AAV genomic copies in tissues—DNA isolation from tissues was performed using DNeasy blood and tissue kit (Qiagen) according to the manufacturer's protocol. qPCR reactions consist of 100 ng template DNA from each sample and primers and probes for viral inverted terminal repeats (ITRs) using Probe Based qPCR Master Mix (IDT) according to the manufacturer's protocol. Data was normalized to mouse Acvr2b control gene.

ELISA-based chemiluminescent assay—After harvesting mice, plasma samples were collected and stored in one-time aliquots at −80° C. Lung samples were lysed using 1× cell lysis buffer (Cell Signaling) (ratio of 100 mg of tissue to 1 ml of buffer) followed by homogenization and sonication of the lysed tissue. The assay was performed using the Q-Plex™ Mouse Cytokine—Screen (16-Plex) kit (Quansys Biosciences) following the manufacturer's protocol. Briefly, samples or calibrators were added into wells of a 96 well plate arrayed with analyte specific antibodies that capture GMCSF, IL-1α, IL-1β, IL-4, IL-5, IL-6, IL-12p70, IL-17, MCP-1, MIP-1α, RANTES, and TNFα. Plates were washed and biotinylated analyte specific antibodies were added. After washing, streptavidin-horseradish peroxidase (SHRP) was added. Following an additional wash, the amount of SHRP remaining on each location of the array was measured with the addition of a chemiluminescent substrate.

Antibody ELISA—Fifty microliter AAV particles diluted in 1× coating buffer (13 mM sodium carbonate, 35 mM sodium bicarbonate buffer, pH 9.2) containing $2 \times 10^9$ per viral particles were added to each well in a Microlon® high protein binding 96-well plate (Greiner). Wells were washed three times with 1× Tris Buffered Saline+Tween-20 (TBST, Bethyl) and blocked with 1× Tris Buffered Saline+1% BSA (Bethyl) for 1 hr. at RT. Wells were washed three times with TBST. The standard curve was generated using purified mouse host IgG2a anti-AAV1 (Fitzgerald) antibody in two-fold dilutions in TBST+1% BSA+1:500 negative control mouse serum, beginning from a concentration of 10,000 ng/ml AAV1 antibody. The standards were added to the plate followed by the serum samples at a dilution of 1:500 and incubated for 1 hr. at RT. Wells were washed four times with TBST and then goat anti-mouse HRP antibody was added at a concentration of 1:500 and incubated for 1 hr. at RT. Wells were washed four times with wash buffer and TMB substrate was added to the wells. Reactions were terminated by adding 0.18 M H2SO4 after development of the standard curve (15 min). Finally, absorbance was measured at 450 wavelengths using a plate reader (BioTek). Absorbance results were exported and analyzed in Excel.

Lactate assay—Blood samples were collected using EDTA coated tubes. Samples were centrifuged at 1,000×g for 10 minutes. Plasma was collected and stored at −80° C. Lactate assay was performed following the manufacturer's protocol (L-Lactate Assay Kit, Cayman Chemicals). Briefly, samples were deproteinated by adding 0.5 M MPA. After pelleting the protein, supernatant was added to Potassium Carbonate and centrifuged at 10,000×g for five minutes at 4° C. Samples were diluted four-fold and added to the designated wells. Next, assay buffer cofactor mixture, Fluorometric Substrate, and Enzyme Mixture were added to each well. Plate was incubated for 20 minutes at RT and the fluorescence was measured using an excitation wavelength of 530-540 nm and an emission wavelength of 585-595 nm. Absorbance results were exported and analyzed in Excel according to the manufacturer's protocol.

Examination of liver injury after LPS injection—Plasma samples were sent to IDEXX Laboratories to measure a panel of tissue injury markers including ALT, Cholesterol, LDL, HDL, BUN, and Lipase.

Animals—All the experiments with animals were approved by the Institutional Animal Care and Use Committee (IACUC) at Arizona State University and have been performed according to institutional guidelines. All the experiments were performed on at least 3 mice of 6-8 weeks old per group. Both male and female were included in each experiment. The sample size in each group is indicated in each figure legend. All mice were handled equally. Male C57BL/6 mice (JAX Stock number: 000664) were used for studying AAV2/1-GFP, tropism towards different organs and AAV-CRISPR activation experiments. Both male and female Rosa26-Cas9 knockin mice (JAX Stock number 026179) were used for AAV-CRISPR repression experiments.

Retro-Orbital injections—AAV particles were delivered to mice through Retro-orbital injection of the venous sinus. Animals were anesthetized with 3% isoflurane and virus particles were injected to the left eye with 100 microliters of AAV solution (1E11 to 1E12 genome copy per mouse for experiments with Cas9 expressing mice and a total of 1.01E+12 GC AAV-TTN and AAV-Cas9 (100:1 ratio) for C57BL/6 mice).

Tissue harvest—Mice were euthanized via $CO_2$ inhalation 3 weeks following injection. Tissue samples taken from liver, spleen, lung, testis, bone marrow and blood were collected in RLT (Life Technologies) or snap frozen for RNA analysis.

In vivo LPS Induction—For LPS induction, mice were treated by intraperitoneal (i.p.) injection of lipopolysaccharides (from *Escherichia coli* 0127:B8 (Sigma-Aldrich, St. Louis, MO, USA) dissolved in phosphate-buffered saline (PBS) at a concentration of 50 mg/ml. Mice were euthanized six hours post LPS injection via $CO_2$ inhalation.

RNA Sequencing and Data Analysis—RNA was extracted from mice bone marrow samples using RNeasy Plus mini kit (Qiagen) followed by globin mRNA depletion using GLOBINclear™ Kit, mouse/rat kit (Thermofisher). None-directional library preparation were performed at Novogene Corporation Inc. followed by RNA sequencing using Illumina Nova Platform with paired-end 150 run (2×150 bases). Coverage was minimum 25 million reads per sample. FASTQ files were then aligned to mouse genome sequence using STAR software and uniquely mapped read counts were visualized with Integrative Genomics Viewer (IGV). Gene expression level was calculated by the number of mapped reads. According to all gene expression level (RPKM or FPKM) of each sample, correlation coefficient of sample between groups was calculated. Readcount obtained from Gene Expression Analysis were used for differential expression analysis and differential expression analysis of different groups was performed using the DESeq2 R package. Hierarchical clustering analysis was carried out of log 10 (FPKM+1) of union differential expression genes, within all comparison groups. ClusterProfiler software was used for enrichment analysis, including GO Enrichment, DO Enrichment, KEGG Enrichment and Reactome Enrichment.

Statistical analysis—Statistical analyses are included in the figure legends. All of the data are presented as the mean±SEM or mean±SD. N=number of individual transfections for in vitro experiments an N=number of animals for in vivo experiments. Statistical analyses were performed using prims 7 Software (GraphPad). the inventors performed two-tailed Student's t-test. A value of p<0.05 was considered significant, represented as * (p<0.05),  (p<0.01), * (p<0.001) or n.s. (not significant).

TABLE 2

14 nt guide sequences within gRNAs described herein - 5'-3'

| Mouse | Myd88-1 | GCCTAGTCCATCCA | (SEQ ID NO: 1) |
|---|---|---|---|
| Mouse | Myd88-2 | CCACCGATCAAGGT | (SEQ ID NO: 2) |
| Mouse | Myd88-3 | GCGAGCGTACTGGA | (SEQ ID NO: 3) |
| Mouse | Myd88-4 | GTGGACGGCACCGG | (SEQ ID NO: 4) |

TABLE 2-continued 14 nt guide sequences within gRNAs described herein - 5'-3'

| | | | |
|---|---|---|---|
| Mouse | Mock | AGCTTAGGGATAAC | (SEQ ID NO: 5) |
| Mouse | CXCR4-1 | ATAAAAGTCCGGTT | (SEQ ID NO: 6) |
| Mouse | CXCR4-2 | TCCGGTAACCACCA | (SEQ ID NO: 7) |

TABLE 3

20 nt guide sequences within gRNAs described herein gRNAs - 5'-3'

| | | |
|---|---|---|
| HumanSEL1L-1 | GGCAGGAAGAGCAGCGGCGAGG | (SEQ ID NO: 8) |
| HumanSEL1L-5 | GGGGGGCGGATACTGACCCG | (SEQ ID NO: 9) |
| HumanSEL1L-7 | GGATACTGACCCGAGGACGCCG | (SEQ ID NO: 10) |
| HumanSYVN1-10 | GGGCGCTGGGTTCCTGGTGAGT | (SEQ ID NO: 11) |
| HumanSYVN1-4 | GGTTGCGGGCGTCGCAGGCA | (SEQ ID NO: 12) |
| HumanSYVN1-3 | GGCACCGGCGTCTGAGGTCTC | (SEQ ID NO: 13) |
| HumanNEAT1-1 | GGCGACAGGGAGGGATGCGCGCC | (SEQ ID NO: 14) |
| HumanNEAT1-2 | GGCGCGCCTGGGTGTAGTTGT | (SEQ ID NO: 15) |
| HumanNEAT1-3 | GGAAGTGGCTAGCTCAGGGCTTC | (SEQ ID NO: 16) |
| HumanXIST-1 | GGCAGCGCTTTAAGAACTGAA | (SEQ ID NO: 17) |
| HumanXIST-2 | GGACTGAAGATCTCTCTGCACTT | (SEQ ID NO: 18) |
| HumanXIST-3 | GGCCATATTTCTTACTCTCTCG | (SEQ ID NO: 19) |
| HumanCXCR4 | GCAGGTAGCAAAGTGACGCCGA | (SEQ ID NO: 20) |

TABLE 4

Mouse qPCR primers - 5'-3'. IDT ™ PRIMETIME ™ predesigned qPCR primer and probe kits are commercially available for the targets noted below and therefore the sequences of these primers are not separately provided herein.

| | | |
|---|---|---|
| GFP-FW1: | CAACCACTACCTGAGCACCC | (SEQ ID NO: 21) |
| GFP-RV1: | GTCCATGCCGAGAGTGATCC | (SEQ ID NO: 22) |
| Myd88 primer FW | GTGAGGATATACTGAAGGAGCTG | (SEQ ID NO: 23) |
| Myd88 primer RV | CTGTAAAGGCTTCTCGGACTC | (SEQ ID NO: 24) |
| Stat4-FW | CCTGACATTCCCAAAGACAAAGC | (SEQ ID NO: 25) |
| Stat4-RV | TCTCTCAGCACAGCATATGCAC | (SEQ ID NO: 26) |
| Cxcl1-FW | GACCATGGCTGGGATTCACC | (SEQ ID NO: 27) |
| Cxcl1-RV | CCAAGGGAGCTTCAGGGTCA | (SEQ ID NO: 28) |
| IFNα-fw | GGACTTTGGATTCCCGCAGGAGAAG | (SEQ ID NO: 29) |
| IFNα-RV | GCTGCATCAGACAGCCTTGCAGGTC | (SEQ ID NO: 30) |
| IFN-γ-PRIMETIME | IDT:MM.PT.58.41769240 | |

TABLE 4-continued

Mouse qPCR primers - 5'-3'. IDT ™ PRIMETIME ™ predesigned qPCR primer and probe kits are commercially available for the targets noted below and therefore the sequences of these primers are not separately provided herein.

| | | |
|---|---|---|
| IFN-β-PRIMETIME | IDT:MM.PT.58.30132453.G | |
| Icam-1-FW | CAATTTCTCATGCCGCACAG | (SEQ ID NO: 31) |
| Icam-1-RV | AGCTGGAAGATCGAAAGTCCG | (SEQ ID NO: 32) |
| TNFα-FW | AGGCTGCCCCGACTACGT | (SEQ ID NO: 33) |
| TNFα-RV | GACTTTCTCCTGGTATGAGATAGCAAA | (SEQ ID NO: 34) |
| NCF-FW | GCTGCGTGAACACTATCCTGG | (SEQ ID NO: 35) |
| NCF-RV | AGGTCGTACTTCTCCATTCTGTA | (SEQ ID NO: 36) |
| 18S-FW | GGCCGTTCTTAGTTGGTGGAGCG | (SEQ ID NO: 37) |
| 18S-RV | CTGAACGCCACTTGTCCCTC | (SEQ ID NO: 38) |
| CD68-FW | TGCGGCTCCCTGTGTGT | (SEQ ID NO: 39) |
| CD68-RV | TCTTCCTCTGTTCCTTGGGCTAT | (SEQ ID NO :40) |
| CXCR4-PRIMETIME | IDT:MM.PT.58.41597935 | |
| CD8-FW | GCTCAGTCATCAGCAACTCG | (SEQ ID NO: 41) |
| CD8-RV | TCACAGGCGAAGTCCATC | (SEQ ID NO: 42) |
| CD4-FW | GAGAGTCAGCGGAGTTCT | (SEQ ID NO: 43) |
| CD4-RV | CTCACAGGTCAAAGTATTGTTG | (SEQ ID NO: 44) |
| IL6-PRIMETIME | IDT:Mm.PT.58.100 | |
| IL1B-FW | TCGCTCAGGGTCACAAGAAA | (SEQ ID NO: 45) |
| IL1B-RV | CATCAGAGGCAAGGAGGAAAAC | (SEQ ID NO: 46) |

TABLE 5

Human qPCR primers - 5'-3'

| | | |
|---|---|---|
| SEL1L-FW | GTGGCTGTTGGAGTCGGTAT | (SEQ ID NO: 47) |
| SEL1L-RV | ATTCACTCCCCACCCTCTCT | (SEQ ID NO: 48) |
| NEAT1-FW | AGGTCAGGCAGAGGAAGTCA | (SEQ ID NO: 49) |
| NEAT1-RV | CTGCCTCCCGATACAACAAT | (SEQ ID NO: 50) |
| XIST-1-FW | AGGTCAGGCAGAGGAAGTCA | (SEQ ID NO: 51) |
| XIST-1-RV | CTGCCTCCCGATACAACAAT | (SEQ ID NO: 52) |
| SYVN1-FW | ACCAGCATCCCTAGCTCAGA | (SEQ ID NO: 53) |
| SYVN1-RV | TCCTCAGGCATCTCCTCTGT | (SEQ ID NO: 54) |

MS2-*krab*-Mecp2 (SEQ ID NO: 55), MS2 (SEQ ID NO: 56), *krab* (SEQ ID NO: 57), and Mecp2 (SEQ ID NO: 58):
CCACCATGGGACCTAAGAAAAAGAGGAAGGTG**GCGGCCGCTGACTACAAG
GATGACGACGATAAATCTAGAATGGCTTCTAACTTTACTCAGTTCGTTCT**

-continued
CGTCGACAATGGCGGAACTGGCGACGTGACTGTCGCCCCAAGCAACTTCG

CTAACGGGATCGCTGAATGGATCAGCTCTAACTCGCGTTCACAGGCTTAC

AAAGTAACCTGTAGCGTTCGTCAGAGCTCTGCGCAGAATCGCAAATACAC

CATCAAAGTCGAGGTGCCTAAAGGCGCCTGGCGTTCGTACTTAAATATGG

AACTAACCATTCCAATTTTCGCCACGAATTCCGACTGCGAGCTTATTGTT

AAGGCAATGCAAGGTCTCCTAAAAGATGGAAACCCGATTCCCTCAGCAAT

CGCAGCAAACTCCGGCATCTACGAGGCCAGCCCCAAGAAGAAGAGGAAGG

TGAGTGGTGGAGGAAGTGGCGGGTCAGGGTCGTCCATGGACGCGAAATCA

*CTTACGGCATGGTCGAGAACACTGGTTACGTTCAAGGACGTGTTTGTGGA*

*CTTTACACGTGAGGAGTGGAAATTGCTGGATACTGCGCAACAAATTGTGT*

*ATCGAAATGTCATGCTTGAGAATTACAAGAACCTCGTCAGTCTCGGATAC*

*CAGTTGACGAAACCGGATGTGATCCTTAGGCTCGAAAAGGGGGAAGAACC*

*TTGGCTGGTATCGGGAGGTGGTTCGGGTGGCTCTGGATCAAGCCCAAAGA*

AGAAACGGAAGGTGGAAGCCTCAGTGCAGGTGAAAAGGGTGCTGGAAAAA

TCCCCCGGCAAACTCCTCGTGAAGATGCCCTTCCAGGCTTCCCCTGGCGG

AAAAGGTGAAGGGGTGGCGCAACCACATCTGCCCAGGTCATGGTCATCA

AGCGACCTGGAAGGAAAAGAAAGGCCGAGGCTGACCCTCAGGCCATTCCA

AAGAAACGGGGACGCAAGCCAGGGTCCGTGGTCGCAGCTGCAGCAGCTGA

GGCTAAGAAAAGGCAGTGAAGGAAAGCTCCATCCGCAGTGTGCAGGAGA

CTGTCCTGCCCATCAAGAAGAGGAAGACTAGGGAGACCGTGTCCATCGAG

GTCAAAGAAGTGGTCAAGCCCCTGCTCGTGTCCACCCTGGGCGAAAAATC

TGGAAAGGGGCTCAAAACATGCAAGTCACCTGGACGGAAAAGCAAGGAGT

CTAGTCCAAAGGGGCGCTCAAGCTCCGCTTCTAGTCCCCCTAAAAAGGAA

CACCATCACCATCACCATCACGCCGAGTCTCCTAAGGCTCCTATGCCACT

GCTCCCACCACCTCCACCACCTGAGCCACAGTCAAGCGAAGACCCCATCA

GCCCACCCGAGCCTCAGGATCTGTCCTCTAGTATTTGCAAAGAGGAAAAG

ATGCCCAGAGCAGGCAGCCTGGAGAGTGATGGCTGTCCAAAAGAACCCGC

CAAGACCCAGCCTATGGTGGCAGCCGCTGCAACTACCACCACAACCACAA

CTACCACAGTGGCCGAAAAATACAAGCATCGCGGCGAGGGCGAACGAAAG

GACATTGTGTCAAGCTCCATGCCCAGACCTAACCGGGAGGAACCAGTCGA

TAGTAGGACACCCGTGACTGAGAGAGTCTCATGA

MS2-HP1A-*krab* (SEQ ID NO: 59), MS2 (SEQ ID NO: 56), HP1A (SEQ ID NO: 60),*krab* (SEQ ID NO: 57)
CCACCATGGGACCTAAGAAAAAGAGGAAGGTGGCGGCCGCTGACTACAAG

GATGACGACGATAAATCTAGAATGGCTTCTAACTTTACTCAGTTCGTTCT

CGTCGACAATGGCGGAACTGGCGACGTGACTGTCGCCCCAAGCAACTTCG

CTAACGGGATCGCTGAATGGATCAGCTCTAACTCGCGTTCACAGGCTTAC

AAAGTAACCTGTAGCGTTCGTCAGAGCTCTGCGCAGAATCGCAAATACAC

CATCAAAGTCGAGGTGCCTAAAGGCGCCTGGCGTTCGTACTTAAATATGG

AACTAACCATTCCAATTTTCGCCACGAATTCCGACTGCGAGCTTATTGTT

AAGGCAATGCAAGGTCTCCTAAAAGATGGAAACCCGATTCCCTCAGCAAT

-continued
CGCAGCAAACTCCGGCATCTACGAGGCCAGCCCCAAGAAGAAGAGGAAGG

TGAGTGGTGGAGGAAGTGGCGGGTCAGGGTCGTCCAGCCCAAGAAAAAA

CGGAAAGTGGAGGCATCAATGAAGGAGGGAGAAAACAACAAACCCAGGGA

GAAAAGTGAAGGGAATAAGAGAAAAAGCTCCTTCTCTAACAGTGCAGACG

ATATCAAGTCCAAGAAAAAGCGGGAGCAGTCTAATGACATTGCTAGGGGC

TTCGAGAGAGGACTGGAGCCAGAAAAAATCATTGGGGCAACCGACAGCTG

CGGCGATCTGATGTTTCTCATGAAATGGAAGGACACAGATGAGGCCGACC

TGGTGCTCGCCAAAGAAGCTAACGTGAAGTGTCCCCAGATCGTCATTGCT

TTTTACGAGGAAAGGCTCACCTGGCACGCATATCCTGAGGATGCCGAAAA

CAAGGAGAAGGAATCAGCTAAGAGCCTCGGGAGGTGGTTCGGGTGGCTCT

GGATCAATGGACGCGAAATCACTTACGGCATGGTCGAGAACACTGGTTAC

*GTTCAAGGACGTGTTTGTGGACTTTACACGTGAGGAGTGGAAATTGCTGG*

*ATACTGCGCAACAAATTGTGTATCGAAATGTCATGCTTGAGAATTACAAG*

*AACCTCGTCAGTCTCGGATACCAGTTGACGAAACCGGATGTGATCCTTAG*

*GCTCGAAAAGGGGGAAGAACCTTGGCTGGTATGA*

MS2-Mecp2-*krab*-MBD2B (SEQ ID NO: 61), MS2 (SEQ ID NO: 56), Mecp2 (SEQ ID NO: 58), *krab* (SEQ ID NO: 57), MBD2B (SEQ DI NO: 62)
CCACCATGGGACCTAAGAAAAAGAGGAAGGTGGCGGCCGCTGACTACAAG

GATGACGACGATAAATCTAGAATGGCTTCTAACTTTACTCAGTTCGTTCT

CGTCGACAATGGCGGAACTGGCGACGTGACTGTCGCCCCAAGCAACTTCG

CTAACGGGATCGCTGAATGGATCAGCTCTAACTCGCGTTCACAGGCTTAC

AAAGTAACCTGTAGCGTTCGTCAGAGCTCTGCGCAGAATCGCAAATACAC

CATCAAAGTCGAGGTGCCTAAAGGCGCCTGGCGTTCGTACTTAAATATGG

AACTAACCATTCCAATTTTCGCCACGAATTCCGACTGCGAGCTTATTGTT

AAGGCAATGCAAGGTCTCCTAAAAGATGGAAACCCGATTCCCTCAGCAAT

CGCAGCAAACTCCGGCATCTACGAGGCCAGCCCCAAGAAGAAGAGGAAGG

TGAGTGGTGGAGGAAGTGGCGGGTCAGGGTCGTCCAGCCCAAAGAAGAAA

CGGAAGGTGGAAGCCTCAGTGCAGGTGAAAAGGGTGCTGGAAAAATCCCC

CGGCAAACTCCTCGTGAAGATGCCCTTCCAGGCTTCCCCTGGCGGAAAAG

GTGAAGGGGTGGCGCAACCACATCTGCCCAGGTCATGGTCATCAAGCGA

CCTGGAAGGAAAAGAAAGGCCGAGGCTGACCCTCAGGCCATTCCAAAGAA

ACGGGGACGCAAGCCAGGGTCCGTGGTCGCAGCTGCAGCAGCTGAGGCTA

AGAAAAGGCAGTGAAGGAAAGCTCCATCCGCAGTGTGCAGGAGACTGTC

CTGCCCATCAAGAAGAGGAAGACTAGGGAGACCGTGTCCATCGAGGTCAA

AGAAGTGGTCAAGCCCCTGCTCGTGTCCACCCTGGGCGAAAAATCTGGAA

AGGGGCTCAAAACATGCAAGTCACCTGGACGGAAAAGCAAGGAGTCTAGT

CCAAAGGGGCGCTCAAGCTCCGCTTCTAGTCCCCCTAAAAAGGAACACCA

TCACCATCACCATCACGCCGAGTCTCCTAAGGCTCCTATGCCACTGCTCC

CACCACCTCCACCACCTGAGCCACAGTCAAGCGAAGACCCCATCAGCCCA

CCCGAGCCTCAGGATCTGTCCTCTAGTATTTGCAAAGAGGAAAAGATGCC

CAGAGCAGGCAGCCTGGAGAGTGATGGCTGTCCAAAAGAACCCGCCAAGA

CCCAGCCTATGGTGGCAGCCGCTGCAACTACCACCACAACCACAACTACC

ACAGTGGCCGAAAAATACAAGCATCGCGGCGAGGGCGAACGAAAGGACAT

TGTGTCAAGCTCCATGCCCAGACCTAACCGGGAGGAACCAGTCGATAGTA

GGACACCCGTGACTGAGAGAGTCTCATCGGGAGGTGGTTCGGGTGGCTCT

GGATCAATGGACGCGAAATCACTTACGGCATGGTCGAGAACACTGGTTAC

GTTCAAGGACGTGTTTGTGGACTTTACACGTGAGGAGTGGAAATTGCTGG

ATACTGCGCAACAAATTGTGTATCGAAATGTCATGCTTGAGAATTACAAG

AACCTCGTCAGTCTCGGATACCAGTTGACGAAACCGGATGTGATCCTTAG

GCTCGAAAAGGGGGAAGAACCTTGGCTGGTATCGGGAGGTGGTTCGGGTG

GCTCTGGATCATCCCCCAAAAAGAAACGCAAGGTAGGCATCTGCTCGCT

ATCTCGGTAACACTGTCGATCTGTCATCATTCGATTTCCGCACTGGCAAG

ATGATGCCTTCTAAACTGCAGAAGAACAAACAGAGGCTGAGAAATGACCC

ACTCAACCAGAATAAGGGAAAACCCGATCTGAACACCACACTCCCTATCC

GGCAGACAGCTAGTATTTTCAAGCAGCCTGTGACTAAAGTCACCAACCAC

CCATCCAATAAGGTGAAATCTGACCCACAGAGGATGAATGAGCAGCCCAG

ACAGCTGTTTTGGGAAAAGCGCCTGCAGGGTCTCTCTGCAAGTGATGTGA

CAGAGCAGATCATTAAGACTATGGAACTGCCAAAAGGACTCCAGGGAGTG

GGACCTGGGTCTAACGACGAGACTCTGCTCTCAGCTGTCGCAAGCGCACT

GCATACCAGCTCCGCACCCATCACAGGACAGGTGAGTGCCGCTGTCGAGA

AGAACCCAGCCGTGTGGCTGAATACTTCACAGCCCCTCTGCAAGGCTTTC

ATCGTCACCGACGAGGATATTCGGAAGCAGGAGGAACGCGTGCAGCAGGT

CCGAAAAATCCTGGAAGACGCTCTCATGGCAGATATTCTGAGCAGAGCAG

CCGACACCGAGGAAATGGATATTGAGATGGACTCCGGGGATGAAGCCTGA

A

MS2-*MBD2B*-HP1A (SEQ ID NO: 63), MS2 (SEQ ID NO: 56), *MBD2B* (SEQ ID NO: 62), HP1A (SEQ ID NO: 60)

CCACCATGGGACCTAAGAAAAAGAGGAAGGTGGCGGCCGCTGACTACAAG

GATGACGACGATAAATCTAGAATGGCTTCTAACTTTACTCAGTTCGTTCT

CGTCGACAATGGCGGAACTGGCGACGTGACTGTCGCCCCAAGCAACTTCG

CTAACGGGATCGCTGAATGGATCAGCTCTAACTCGCGTTCACAGGCTTAC

AAAGTAACCTGTAGCGTTCGTCAGAGCTCTGCGCAGAATCGCAAATACAC

CATCAAAGTCGAGGTGCCTAAAGGCGCCTGGCGTTCGTACTTAAATATGG

AACTAACCATTCCAATTTTCGCCACGAATTCCGACTGCGAGCTTATTGTT

AAGGCAATGCAAGGTCTCCTAAAAGATGGAAACCCGATTCCCTCAGCAAT

CGCAGCAAACTCCGGCATCTACGAGGCCAGCCCCAAGAAGAAGAGGAAGG

TGAGTGGTGGAGGAAGTGGCGGGTCAGGGTCGTCCTCCCCCAAAAAGAAA

CGCAAGGTGGAGGCATCTGCTCGCTATCTCGGTAACACTGTCGATCTGTC

ATCATTCGATTTCCGCACTGGCAAGATGATGCCTTCTAAACTGCAGAAGA

ACAAACAGAGGCTGAGAAATGACCCACTCAACCAGAATAAGGGAAAACCC

GATCTGAACACCACACTCCCTATCCGGCAGACAGCTAGTATTTTCAAGCA

GCCTGTGACTAAAGTCACCAACCACCCATCCAATAAGGTGAAATCTGACC

CACAGAGGATGAATGAGCAGCCCAGACAGCTGTTTTGGGAAAAGCGCCTG

CAGGGTCTCTCTGCAAGTGATGTGACAGAGCAGATCATTAAGACTATGGA

ACTGCCAAAAGGACTCCAGGGAGTGGGACCTGGGTCTAACGACGAGACTC

TGCTCTCAGCTGTCGCAAGCGCACTGCATACCAGCTCCGCACCCATCACA

GGACAGGTGAGTGCCGCTGTCGAGAAGAACCCAGCCGTGTGGCTGAATAC

TTCACAGCCCCTCTGCAAGGCTTTCATCGTCACCGACGAGGATATTCGGA

AGCAGGAGGAACGCGTGCAGCAGGTCCGAAAAATCCTGGAAGACGCTCTC

ATGGCAGATATTCTGAGCAGAGCAGCCGACACCGAGGAAATGGATATTGA

GATGGACTCCGGGGATGAAGCCTCGGGAGGTGGTTCGGGTGGCTCTGGAT

CAGCCCCAAGAAAAAACGGAAAGTGGAGGCATCAATGAAGGAGGGAGAA

AACAACAAACCCAGGGAGAAAAGTGAAGGGAATAAGAGAAAAAGCTCCTT

CTCTAACAGTGCAGACGATATCAAGTCCAAGAAAAAGCGGGAGCAGTCTA

ATGACATTGCTAGGGGCTTCGAGAGAGGACTGGAGCCAGAAAAAATCATT

GGGGCAACCGACAGCTGCGGCGATCTGATGTTTCTCATGAAATGGAAGGA

CACAGATGAGGCCGACCTGGTGCTCGCCAAAGAAGCTAACGTGAAGTGTC

CCCAGATCGTCATTGCTTTTTACGAGGAAAGGCTCACCTGGCACGCATAT

CCTGAGGATGCCGAAAACAAGGAGAAGGAATCAGCTAAGAGCTGA

We claim:

1. A synthetic repression system for repressing myeloid differentiation primary response 88 (MyD88) expression in vivo comprising:
   (a) a nucleotide sequence encoding a guide RNA (gRNA) comprising
      (i) a nucleic acid encoding a guide sequence comprising a sequence complementary to a portion of MyD88 and
      (ii) an MS2 aptamer target site specific for an RNA binding bacteriophage MS2 coat protein;

(b) a nucleotide sequence encoding the RNA binding bacteriophage MS2 coat protein fused to a repression domain and comprising a sequence selected from the group consisting of SEQ ID NOs: 55, 59, 61, and 63; and (c) a nucleotide sequence encoding a multifunctional Cas nuclease;

wherein the nucleotide sequences are packaged in at least one vector for viral delivery.

2. The synthetic repression system of claim 1, wherein the gRNA guide sequence is 15 or fewer nucleotides in length.

3. The synthetic repression system of claim 1, wherein the gRNA guide sequence targets within 100 base pairs (bp) upstream of TATA box region of MyD88.

4. The synthetic repression system of claim 1, wherein gRNA guide sequence is selected from the group consisting of SEQ ID NOs:1-4.

5. The synthetic repression system of claim 1, wherein the repression domain is selected from the group consisting of a Kruppel associated box (KRAB) domain, methyl-CpG (mCpG) binding domain 2 (meCP2), Switch independent 3 transcription regulator family member A (SIN3A), histone deacetylase HDT1 (HDT1), n-terminal truncation of methyl-CpG-binding domain containing protein 2 (MBD2B), nuclear inhibitor of protein phosphatase-1 (NIPP1), and heterochromatin protein 1 (HP1A).

6. The synthetic repression system of claim 1, wherein the multifunctional Cas nuclease fused to the repression domain.

7. The synthetic repression system of claim 1, wherein the Cas nuclease is a *Staphylococcus aureus* Cas9 nuclease or a *Streptococcus pyogenes* Cas9 nuclease.

8. The synthetic repression system of claim 1, wherein the vector is an AAV2/1 delivery vector.

9. A pharmaceutical composition comprising the synthetic repression system of claim 1 and a pharmaceutically acceptable delivery vehicle.

10. The synthetic repression system of claim 1, wherein the nucleotide sequences comprise three cassettes, wherein the first cassette comprises the nucleotide sequence of (a), wherein the second cassette comprises the nucleotide sequence of (b), and wherein the third cassette comprises the nucleotide sequence of (c).

11. The synthetic repression system of claim 6, wherein the nucleotide sequences comprise two cassettes, wherein the first cassette comprises the nucleotide sequence of (a), and wherein the second cassette comprises the nucleotide sequences of (b) and (c).

* * * * *